US008741861B2

(12) United States Patent
Mann

(10) Patent No.: US 8,741,861 B2
(45) Date of Patent: Jun. 3, 2014

(54) METHODS OF NOVEL THERAPEUTIC CANDIDATE IDENTIFICATION THROUGH GENE EXPRESSION ANALYSIS IN VASCULAR-RELATED DISEASES

(75) Inventor: David M. Mann, San Diego, CA (US)

(73) Assignee: Vascular Biosciences, San Diego, CA (US)

( * ) Notice: Subject to any disclaimer, the term of this patent is extended or adjusted under 35 U.S.C. 154(b) by 177 days.

(21) Appl. No.: 12/934,950

(22) PCT Filed: Mar. 27, 2009

(86) PCT No.: PCT/US2009/038685
§ 371 (c)(1),
(2), (4) Date: Dec. 21, 2010

(87) PCT Pub. No.: WO2009/121031
PCT Pub. Date: Oct. 1, 2009

(65) Prior Publication Data
US 2011/0091421 A1 Apr. 21, 2011

Related U.S. Application Data

(60) Provisional application No. 61/040,065, filed on Mar. 27, 2008.

(51) Int. Cl.
C12N 15/11 (2006.01)
A61K 38/00 (2006.01)
G01N 1/00 (2006.01)

(52) U.S. Cl.
CPC ...................................... G01N 1/00 (2013.01)
USPC ....................................... 514/44 A; 514/15.7

(58) Field of Classification Search
None
See application file for complete search history.

(56) References Cited

U.S. PATENT DOCUMENTS

| 5,406,959 | A | * | 4/1995 | Mann | 600/566 |
|---|---|---|---|---|---|
| 2005/0037366 | A1 | | 2/2005 | Gut et al. | |
| 2005/0037946 | A1 | | 2/2005 | Stagliano et al. | |
| 2006/0019272 | A1 | | 1/2006 | Geraci et al. | |
| 2006/0185027 | A1 | * | 8/2006 | Bartel et al. | 800/14 |
| 2007/0172856 | A1 | | 7/2007 | Hogaboam et al. | |
| 2008/0171715 | A1 | * | 7/2008 | Brown et al. | 514/44 |

FOREIGN PATENT DOCUMENTS

WO WO 2008073922 A2 * 6/2008

OTHER PUBLICATIONS de la Torre, Is Alzheimer's disease a neurodegenerative or a vascular disorder? , Mar. 2004, Lancet Neurology, vol. 3, 3: 184-190.*
Dictionary of Science and Technology, 1992, Academic Press, online edition.*
McLaughlin et al, Pulmonary arterial hypertension, 2006, Circulation, 114:1417-1431).*
Vidal et al, Making sense of antisense, 2005, European Journal of Cancer, 41:2812-18.*
Barst et al, Diagnosis and Differential Assessment of pulmonary arterial hypertension, 2004, Journal of the American College of Cardiology, vol. 43, No. 12, Supplement S, p. 40S-47S.*
Esau et al, WO 2005/013901 A2, only pp. 1-250 are included.*
Chan and Loscalzo, "Pathogenic Mechanisms of Pulmonary Arterial Hypertension," (2007) Journal of Molecular and Cellular Cardiology 44:14-30.
Geraci et al., "Gene Expression Patterns in the Lungs of Patients with Primary Pulmonary Hypertension: A Gene Microarray Analysis," (2001) Circulation Research 88:555-562.
Giaid and Saleh, "Reduced Expression of Endothelial Nitric Oxide Synthase in the Lungs of Patients with Pulmonary Hypertension," (1995) New England Journal of Medicine 333:214-221.
Hoshikawa et al., "Hypoxia Induces Different Genes in the Lungs of Rats Compared with Mice," (2003) Physiological Genomics 12:209-219.
Kwapiszewska et al., "Expression Profiling of Laser-Microdissected Intrapulmonary Arteries in Hypoxia-Induced Pulmonary Hypertension," (2005) Respiratory Research 6:109-124.
McMurtry et al., "Gene Therapy Targeting Survivin Selectively Induces Pulmonary Vascular Apoptosis and Reverse Pulmonary Arterial Hypertension," (2005) Journal of Clinical Investigation 115(6):1479-1491.
Mittal et al., "Hypoxia-Dependent Regulation of Nonphagocytic NADPH Oxidase Subunit NOX4 in the Pulmonary Vasculature," (2007) Circulation Research 101:258-267.
Motte et al., "Endothelin Receptor Antagonists," (2006) Pharmacology & Therapeutics 110:386-414.
Ji et al., "MicroRNA Expression Signature and Antisense-Mediated Depletion Reveal an Essential Role of MicroRNA Vascular Neointimal Lesion Formation," (2007) Circulation Research 100:1579-1588.
Schermuly et al., "Phosphodiesterase 1 Upregulation in Pulmonary Arterial Hypertension: Target for Reverse-Remodeling Therapy," (2007) Circulation 115:2331-2339.
Thistlethwaite et al., "Human angiopoietin gene expression is a marker for severity of pulmonary hypertension in patients undergoing pulmonary thromboendarterectomy." J Thoracic Cardiovascular Surgery (Jul. 2001) 122 (1):65-73.

(Continued)

Primary Examiner — Tracy Vivlemore
Assistant Examiner — Kate Poliakova-Georgantas
(74) Attorney, Agent, or Firm — Lewis Kohn & Fitzwilliam LLP; David M. Kohn; Kari Moyer-Henry

(57) ABSTRACT

The present invention discloses multiple treatment regimens for vascular-related diseases and disorders. The present invention provides for methods of treating vascular-related disorders based on gene expression studies from samples collected from individuals having symptoms of vascular-related disorders. Additionally, methods are disclosed involving diagnostic techniques to focus treatment regimens. Finally, methods of treating vascular-related disorder involving targeting microRNAs are also disclosed.

11 Claims, 1 Drawing Sheet

(56) References Cited

OTHER PUBLICATIONS

Rothman et al., "Increased expression of endoarterial vascular cell adhesion molecule-1 mRNA in an experimental model of lung transplant rejection: diagnosis by pulmonary aterial biopsy." Transplantation (Apr. 2003) 75(7): 1-6.

Fartoukh et al., "Chemokine macrophage inflammatory protein-1 alpha mRNA expression in lung biopsy specimens of primary pulmonary hypertension." Chest (Jul. 1998) 114(1): 50S-51S.

\* cited by examiner

METHODS OF NOVEL THERAPEUTIC CANDIDATE IDENTIFICATION THROUGH GENE EXPRESSION ANALYSIS IN VASCULAR-RELATED DISEASES

CROSS-REFERENCES

This application claims the benefit of priority of U.S. Provisional Application Ser. No. 61/040,065, filed on Mar. 27, 2008, the disclosure of which is hereby incorporated by referenced in its entirety.

FIELD OF THE INVENTION

The present invention relates to assessment and identification of expression of genes related to vascular-related diseases. The present invention also includes methods of comparing gene expression patterns with respect to various disease states.

BACKGROUND OF THE INVENTION

Pulmonary arterial hypertension (PAH) is an occlusive disease of the pulmonary arteries leading to serious hemodynamic abnormality, right heart failure, and premature death. The molecular mechanisms behind PAH are still unclear. Without a more complete understanding of PAH and how its complex vascular dysfunctions relate to one another, patients will suffer from imprecise diagnosis and drug therapy that may be less than optimal. Despite recent advances and introduction of new clinically approved drugs, the 5-year survival from pulmonary hypertension remains an estimated 50% (Archer and Rich, 2000). Consequently, treatment for PAH, while recently improved, still offers significant and long-lasting improvement in only a minority of patients. A methodology to elucidate the molecular pathways associated with PAH could guide the development of new therapies for this disease.

Though platelets and other cells may have a role in PAH, pulmonary endothelial cells and pulmonary smooth muscle cells appear to be the primary sites of disease progression (Humbert et al 2004). Molecular pathways that show abnormality in pulmonary endothelial cells and pulmonary smooth muscle cells during PAH include endothelin-1 (Giaid et al 1993), serotonin & serotonin transporter (Marcos et al 2003), thromboxane (Walmrath et al 1997), nitric oxide synthase (Kobs and Chesler 2006), prostacyclins (Gailes, et al 2001), potassium channels (Mandegar et al 2002), BMP signaling (Eddahibi et al 2002), and survivin (McMurtry et al 2005). PAH impairs normal signaling and growth in both pulmonary endothelial and pulmonary smooth muscle cells, yet the cellular abnormalities seem to shift over time in unpredictable patterns that has thus far escaped concise definition (Michelakis, 2006).

PAH may be understood as proceeding in phases. In early PAH, endothelial apoptosis occurs, probably resulting in pulmonary arteriole plugging and an increase in pulmonary vascular pressure (Michelakis, 2006). In late PAH, chronic exposure to elevated pulmonary artery pressure together with dysfunctional endothelial signaling initiates hyperproliferation of smooth muscle cells (McMurtry et al 2005). Increased concentric pulmonary smooth muscle cell proliferation leads to ever increasing pulmonary artery pressure, right ventricular failure, and death.

Lung pathology in all PAH patients show thickening throughout the arterial wall of the pulmonary vascular bed. In some forms of the disease, the pulmonary vascular lesions are reversible (e.g. in newborns with congenital heart defects). In other patients, such as those with the idiopathic form, the lesions are irreversible. It is unknown how these variations in PAH relate to one another on a molecular basis (Pearl et al 2002).

Current therapies for PAH patients primarily target vascular tone. Treatments that aim at correcting potassium channel dysfunction (Machado et al 2001), nitric oxide impairment (Humbert et al 2004), prostacyclin impairment (Tuder et al 1999, Christman et al 1992), and endothelin-1 expression (Giaid et al 1993) have all been clinically available for several years. These therapies offer some relief from hemodynamic symptoms, but most patients show only a transient response. The proliferative disease continues to progress in most PAH patients, resulting in a five year mortality rate that remains at around 50% (Newman et al 2004).

Currently, there are no clinically available routine means to obtain endothelial and smooth muscle samples from the pulmonary arteries of pulmonary hypertension patients for diagnosis, disease staging or drug discovery. Applicant's earlier invention, described in U.S. Pat. No. 5,406,959, describes an endoarterial biopsy catheter that has demonstrated its safety and effectiveness in normal canines (Rothman, Mann et al., 1996), canines with experimentally-induced pulmonary hypertension (Rothman, Mann et al., 1998), and canines with single-sided lung transplant rejection (Rothman, Mann et al., 2003). Preliminary studies have also demonstrated the safety and efficacy of a catheter-based method to obtain endovascular samples from a porcine model of PAH.

Percutaneously-obtained pulmonary endoarterial biopsy samples were found to be of sufficient quantity and quality for porcine whole genome mRNA microarray analysis and microRNA analysis. Whole genome microarray analysis revealed time-sensitive variations in gene expression values as PAH progressed in the subject animal model. Genes previously shown to be associated with PAH displayed changes characteristic of the disease, and genes previously unassociated with PAH also displayed expression level dysregulation. These findings raise the possibility that the endoarterial biopsy catheter combined with microarray analysis may provide a valuable platform for the discovery of novel drug and biomarker targets in pulmonary hypertension and a platform to deliver individualized pharmacotranscriptomics.

MicroRNA analysis revealed pressure sensitive changes in microRNA expression. As our surgical shunt model of pulmonary hypertension progressed from a high flow low pressure (HFLP) manifestation to a high flow high pressure (HFHP) manifestation, different microRNAs became dysregulated either increasing or decreasing in expression relative to our baseline normal values.

Most new therapies promise to focus on arresting either the endothelial apoptosis that characterizes early PAH (angiopoetin-1 & endothelial nitric oxide synthase cell-base gene transfer (Zhao et al 2003; 2005), caspase inhibitors (Taraseviciene-Stewart at al 2001)) or the smooth muscle cell proliferation typical of late PAH (dichloroacetate (McMurtry et al 2004), simvastatin (Nishimura et al 2003), sidenafil (Wharton et al 2005), imatinib (Schermuly et al 2005), anti-survivin (McMurtry et al 2005), K+ channel replacement gene therapy (Pozeg et al 2003)).

Before administering therapies, however, it would be extremely valuable to determine which genes are dysregulated in each PAH patient at any stage of their individual disease progression. Without knowing what genes are aberrant during any point in the patient's disease course, targeted therapies may miss the mark in some patients. Life threatening side effects may emerge if the wrong cells, at the wrong time, are encouraged to die or proliferate in patients with compromised pulmonary vascular health.

A powerful method for determining the gene expression levels of thousands of genes simultaneously are DNA microarrays. Initially used for the classification of cancers that were difficult to discriminate histologically (Golub et al 1999, Bhattacharjee et al 2001, and Ramaswamy et al 2001), microarrays have been more recently applied to PAH (Geraci et al 2001). PAH microarray studies have been performed on whole lung homogenates in humans (Fantozzi et al 2005) and rats (Hoshikawa et al 2003), surgically-dissected pulmonary arteries in pigs (Medhora et al 2002), laser-microdissected pulmonary arteries in rats (Kwapiszewska et al 2005), and mononuclear peripheral blood in humans (Bull et al 2004). These studies have been performed to discover potentially novel PAH disease pathways, biomarkers, therapeutic targets and patient classification gene expression profiles.

To advance PAH microarray studies into practical clinical use, tissue procurement methodologies are required that do not require surgical explant or postmortem procurement, and peripheral blood has thus far proven to be inadequate to discriminate gene expression signatures between subgroups of PAH patients (Bull et al 2004; Bull et al 2007). To take advantage of the full power of microarray technologies in PAH patients, a safe and effective minimally invasive means for the repeat procurement of endovascular samples from living PAH patients is required.

The present invention provides for the use of a novel interventional catheter, an endoarterial biopsy catheter, to obtain serial biopsy specimens from hypertensive pulmonary vessels for analysis. The ability to procure endothelial and smooth muscle samples in a minimally invasive manner will allow physicians to use microarray profiling and other techniques to classify patients upon initial presentation according to their gene expression signatures, prescribe therapies that target genes empirically found to be dysregulated in each individual patient, and monitor and adjust PAH patient therapy according to subsequent biopsy findings. A greater understanding of the complex molecular pathways underlying each patient's PAH should enable more precise diagnosis and the delivery of more effective therapies. Also of importance is the ability to discover new uses for existing drugs as well as discovering new drug targets.

Individualized pharmacotranscriptomics based on endoarterial biopsy and microarray analysis represents a reasonable choice for researchers struggling with the complexities and contradictions of PAH and other vascular diseases. The huge literature generated from in vitro and animal studies falls short, at times, in addressing the actual facts of patient health. Many commentators describe this dilemma as the "bench-to-bedside gap", where in vitro and animal laboratory data fails to model human disease circumstances (Aird, 2004). Bridging that gap through catheter-based access to the vasculature in a model that recapitulates the clinical and histopathological manifestations of a form of human pulmonary hypertension will likely enable closer correlations between animal studies and patient care, and serve as a model for other vascular-based diseases such as atherosclerosis, congestive heart failure, sickle cell disease, organ transplant rejection, connective tissue diseases, chronic obstructive pulmonary disease, pulmonary embolism, asthma, systemic inflammatory response, battlefield trauma, cancer, sepsis and acute respiratory distress syndrome. There is a need in the art to provide data from gene expression analyses in order to target novel candidates for use in treating or preventing PAH.

SUMMARY OF THE INVENTION

One aspect of the present invention provides for methods of treating an individual suffering from a vascular-related disease comprising the steps of:
  a) obtaining a biopsy sample from the individual's pulmonary artery;
  b) analyzing gene expression levels of the biopsy sample from the pulmonary artery of the individual and a non-diseased control;
  c) comparing the gene expression levels between the biopsy sample from the pulmonary artery of the individual and the non-diseased control;
  d) identifying at least one gene from step c) that is upregulated or downregulated in the biopsy sample based on the non-diseased control;
  e) obtaining gene products from the genes identified in step c); and
  f) selecting pharmaceutical agents which are known inhibitors of the gene products from the at least one upregulated gene or known promoters of the gene products from the at least one downregulated gene. An additional aspect to the present invention provides for the pharmaceutical agents selected for administration to the individual suffering from the vascular-related disease. In yet another aspect, the individual is categorized based on progression of the vascular-related disease, with the treatment being based on the timing of the disease.

Another aspect of the present invention provides for a means of comparing varying levels of gene expression based on an animal model for pulmonary arterial hypertension. In a preferred embodiment, the genes expressed in the animal model are genes found to be either upregulated or downregulated. In a more preferred embodiment, the upregulated or downregulated genes are time-dependent based on the time after exposure to the PAH.

Another aspect of the present invention provides for methods of identifying genes involved in the pathway of PAH based on differential gene expression studies in a time-dependent animal model for PAH. In one embodiment, the genes are compared to other known genes which are upregulated or downregulated in the known PAH pathway.

Yet another aspect of the present invention provides for methods of diagnosing a vascular-related disease in an individual comprising the steps of:
  a) identifying at least one gene that is upregulated or downregulated in the vascular-related disease comprising the steps of:
    1) obtaining a biopsy sample from the individual's pulmonary artery during progression of the vascular-related disease;
    2) obtaining a pulmonary artery sample from a non-diseased control;
    3) extracting RNA from the samples in steps 1) and 2);
    4) obtaining gene products from the RNA extracted in step 3); and
    5) comparing gene expression levels from the biopsy sample with the non-diseased control, and
  b) associating the genes upregulated in the biopsy sample with an inhibitor of the gene products for administration to the individual and genes downregulated in the biopsy sample with a promoter of the gene products for administration to the individual.

Another aspect of the present invention provides for methods of treating an individual having a vascular-related disease by targeting microRNAs comprising the following steps:

a) assessing a stage of the vascular-related disease in the individual;

b) identifying whether microRNAs are upregulated or downregulated;

c) selecting the microRNAs to target based on the stage of the vascular-related disease and whether the microRNAs are upregulated or downregulated; and d) administering an agent known to inhibit an upregulated microRNA or an agent known to promote a downregulated microRNA to the individual. A variation of this embodiment provides for the stage of the vascular-related disease being based on flow rates and blood pressure within an artery of the individual.

Another aspect of the present invention provides for methods of therapeutically targeting microRNA dysregulated in PAH comprising the steps of:

(a) obtaining a biopsy sample from the pulmonary artery during the progression of PAN;

(b) obtaining a pulmonary artery sample from a non-diseased control;

(c) extracting RNA from the artery samples;

(d) converting the RNA to cDNA;

(e) comparing levels of microRNA expression at the two differing times;

(f) identifying microRNA dysregulated in PAH relative to baseline; and (g) inhibiting upregulated microRNA or promoting downregulated microRNA identified in PAH biopsies.

DETAILED DESCRIPTION OF THE INVENTION

Figure 3:
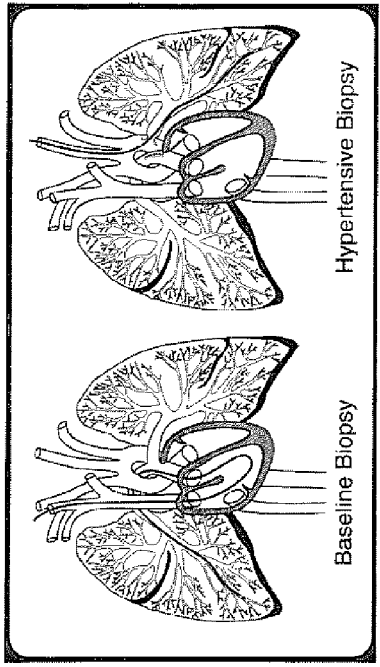
FIG. 3 depicts biopsies: normal vessels at baseline, hypertensive LPA at 7, 21, 60 and 180 days post shunt.
Figure 4:
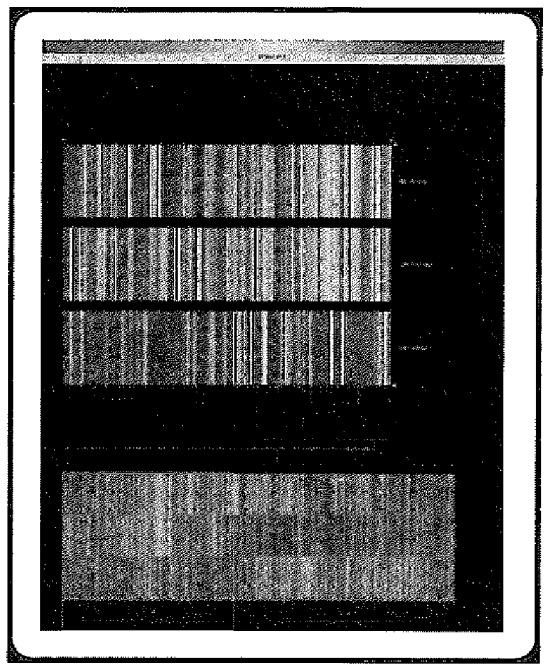
FIG. 4 depicts GeneSpring downstream analysis of microarray data.

The model described in the present invention is surgically-induced PAH in pigs. Our model mimics human Eisenmenger syndrome (a form of PAH related to congenital heart malformation) in both symptoms and pathology (Corno et al 2003). The size of the animals makes the pulmonary vessels available to the catheter, providing a ready transition to human clinical use. And finally, the commercial availability of whole genome porcine microarrays (Bai et al 2003) makes the species ideal for our purposes in the study, and renders the use of cross species microarrays unnecessary (Medhora et al 2002).

By obtaining pulmonary endovascular samples at early, intermediate and late time points in PAH progression, and analyzing these samples using porcine whole genome microarrays, a time-sensitive microarray based map of the underlying molecular biology of PAH may be obtained. Improved knowledge of the molecular mechanisms underlying PAH progression can lead to the identification of stage-specific biomarkers, new therapeutic targets for drug intervention, and novel signaling pathways involved in the pathogenesis of PAH. These novel target genes can then be validated using quantitative PCR and immunohistochemical stains on porcine endoarterial biopsy samples procured concurrently. At the same time, the combination of minimally invasive endoarterial biopsy and whole genome microarray analysis can serve as an animal model for subsequent studies in PAH patients.

The following examples provided in this disclosure provide a profile gene expression in pulmonary hypertensive pigs by surgical anastomosis of the left pulmonary artery to the descending aorta. Endoarterial biopsy samples are collected from animals with a surgical shunt model of pulmonary hypertension at multiple time points over a 6-month time course. Gene expression analysis of the biopsy samples was performed on porcine microarrays. Microarray analysis was performed to detect dysregulated genes previously unassociated with PAH, discover novel biomarkers of pulmonary hypertension and novel targets for therapeutic intervention and advance knowledge of the molecular mechanisms of pulmonary hypertension. These studies will also help validate a new platform for PAH diagnosis and drug discovery, endoarterial biopsy and microarray analysis, for eventual clinical practice.

EXAMPLES

Example I

Construction of a Microarray-Based Map of Changes in Gene Expression During the Progression of PAH and the Identification of Novel Therapeutic Candidates In an animal model of PAH created by Antonio Corno and colleagues, pigs undergo surgery that redirects systemic circulation into the left pulmonary artery mimicking pulmonary hypertension secondary to congenital heart disease. The surgery elevates PA pressure and creates the same hemodynamic conditions that PAH patients experience. The present study investigates how the elevated pressure remodels the pulmonary vasculature. In Corno's studies, histology on necropsy confirmed intimal hyperplasia in the pulmonary arteries, evidence that the surgical shunt surgery described will cause endovascular remodeling (Corno et al 2003).

Biopsy Extraction and Surgery Protocol 20-30 kg Yucatan Micropigs (*Sus scrofa*, Yucatan micro breed) underwent surgical anastomosis of the left pulmonary artery to the descending aorta, resulting in left pulmonary arterial hypertension of at least ½ systemic levels. Animals are penned in the laboratory for no less than one week prior to surgery and fed normal chow. On surgery day, animals were premedicated with 20 mg/kg intramuscular ketamine and 0.1 mg/kg intramuscular midazolam. After 0.25 mg of intramuscular atropine, anesthesia was induced with 1 mg/kg intravenous midazolam and 0.1 mg/kg intravenous fentanyl and maintained with 0.1 mg/kg/hr intravenous pancuronium bromide. Pigs were ventilated with an inspired oxygen fraction (FiO2) of 0.4, a tidal volume of 15 ml/kg, and a respiratory rate of 12 breaths/minute. One gram of intravenous cefazolin was given before and 2 hours after the surgical procedure. Surgical and catheter procedures were performed under general anesthesia with endo-tracheal intubation. Sedation medications and anesthetics were administered by an anesthesiologist. Intra-cardiac and intravascular pressures, EKG, and blood oxygen saturations were monitored continuously.

Figure 1:
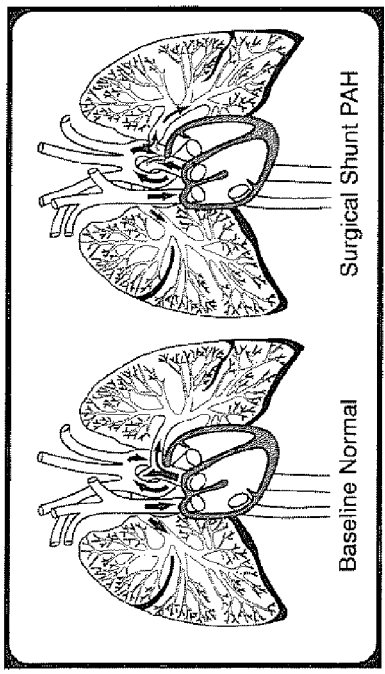
FIG. 1 depicts a surgical shunt model of PAH and its association with congenital heart disease (CHD).

Under sterile conditions (the thoracic area was shaved and prepared with betadine, a left thoracotomy was performed through the fourth intercostal space, about 5 centimeters, to expose the great arteries. The main pulmonary artery (MPA) and its branches were identified and freed from surrounding tissue. Two clamps were placed on the proximal left pulmonary artery (LPA). The proximal LPA was sutured closed, using prolene, and the distal LPA was sutured end to side in a clamped region in the descending aorta (FIG. 1), using cardiovascular prolene. Pieces of LPA endoarterial tissue were taken for histology. The clamps were removed and an IV dose of 1 mg/kg Furosemide immediately given. Hemostasis was obtained with sutures and cautery. Direct needle blood pressures were recorded in the main pulmonary artery and in the newly anastomosed left pulmonary artery. The chest was closed with sutures, both subcutaneous and cutaneous layers, using prolene and surgical wire. The animals then were weaned from anesthesia and mechanical ventilation. Postoperative analgesia was provided with morphine four times a day and a 1-2 mg/kg dose from 0.25% solution of IV Bupivacaine, a local anesthetic. A circulating warming blanket was used during surgery and recovery.

Figure 2:
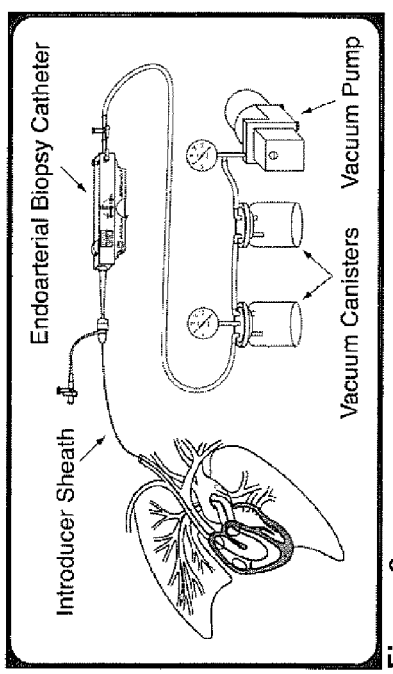
FIG. 2 depicts the endoarterial biopsy procedural configuration.

Endoarterial biopsies were performed at baseline prior to surgery to obtain unaffected tissue, and at post-shunt timepoints to obtain hypertensive biopsy samples (FIG. 2). Follow up endoarterial biopsy procedures were scheduled 7, 21, 60 and 180 days after surgery. On each catheterization day, animals were premedicated with 10 mg/kg of IV propofol, were intubated and ventilated at a rate of 12 breaths/min and were maintained under anesthesia with 1.5% halpthane. A femoral artery line was placed for monitoring. To obtain biopsies from the hypertensive left lung, an 8F introducer is placed in a carotid artery, and a 7F endhole catheter is advanced into the aorta. An angiogram is performed to visualize the LPA-aortic anastomosis. The 7F endhole catheter is then threaded through the anastomosis with X-ray fluroscopic guidance. An angiogram of the hypertensive left pulmonary vascular tree is then performed, and the catheter is advanced to the distal pulmonary artery selected for biopsy. A 0.038 in, 260 cm extra stiff Amplatz exchange guide wire will then be passed through the end-hole catheter. The end-hole catheter was exchanged for a long flexible 8F introducer sheath that is adapted with a radio opaque band at the distal end and shaped to conform to the vascular pathway. A 7F angiographic catheter was advanced through the sheath in to a 2.5 mm to 3.0 mm distal pulmonary artery branch, where an angiogram was obtained. The angiographic catheter will serve as a guide to advance the stiff sheath into a small vessel targeted for biopsy and will then be exchanged for the endoarterial biopsy catheter.

The endoarterial biopsy catheter has an external diameter of 2.5 mm and is composed of two flexible polymeric tubes that slide relative to each other. The inner tube has a stainless steel distal end with a beveled opening that is designed to accommodate arterial tissue. A vacuum is coupled to the inner tube and channeled to the beveled opening. The outer tube terminates in a stainless steel cutting tube. The proximal ends of the two tubes are with a spring powered operating mechanism. To obtain the biopsy sample a vacuum is transmitted to the beveled opening of the inner tube, causing a tissue sample to be drawn in. The outer tube is then advanced over the inner tube, severing the tissue sample. With this design, the area of artery contacted by the outer periphery of the beveled opening is larger than the inner aperture connected to the vacuum, this maintaining the tissue sample with its orientation preserved. After each biopsy, the catheter was removed and the tissue sample was placed in the appropriate solution for further processing and analysis. After the biopsy procedures were completed, repeated angiograms were obtained to assess the degree of vascular injury. At the end of the procedure, the biopsy catheter and introducer sheath were removed and hemostasis was obtained by surgical repair of the carotid artery. The animals will then be weaned from anesthesia and mechanical ventilation. Postoperative analgesia was provided with morphine four times a day and or fentanyl patches and non-steroidal anti-inflammatory drugs four times a day.

Tissue Processing

For microarray analysis, biopsy samples are placed in a test tube containing RNAlater (Qiagen), flash frozen in dry ice, and kept frozen until RNA extraction. Additional samples are preserved in formalin, OCT freezing solution, or Bouin's solution for subsequent immunohistochemical and quantitative PCR analysis.

Porcine Genome Arrays

The Affymetrix GeneChip® Porcine Genome Array provides comprehensive coverage of the Sus scrofa transcriptome. The array contains 23,937 probe sets that interrogate approximately 23,256 transcripts from 20,201 Sus scrofa genes.

The sequence information for this array was selected from public data sources including UniGene Build 28 (August 2004), GenBane mRNAs up to Aug. 24, 2004, and GenBank® porcine mitochondrial and rRNA sequences. Probe sets consist of up to eleven probe pairs. The array format consists of eleven micron features synthesized on the 100 format.

RNA Extraction from Endoarterial Biopsy Samples

RNA was prepared from fresh frozen endoarterial biopsy samples in a segregated laboratory, specially prepared and cleaned regularly to destroy nucleases. Specimens were homogenized using QIAshredder columns (Qiagen, Valencia, Calif.) utilized in a FastPrep FP120 Homogenizer (Thermo Electron Corporation, Waltham, Mass.). RNA was isolated using RNeasy Mini columns (Qiagen, Valencia, Calif.) as per manufacturer's protocol. All total RNA was eluted in nuclease free water, and quantity was established by UV spectrophotometer. Final RNA integrity was evaluated by capillary electrophoresis on the Agilent 2100 Bioanalyzer (Agilent, Palo Alto, Calif.).

Gene Expression

Before target production, the quality and quantity of each RNA sample was assessed using a 2100 BioAnalyzer (Agilent). Target was prepared and hybridized according to the "Affymetrix Technical Manual". Total RNA (ug) was converted into cDNA using Reverse Transcriptase (Invitrogen) and a modified oligo (dT)24 primer that contains T7 promoter sequences (GenSet). After first strand synthesis, residual RNA was degraded by the addition of RNaseH and a double-stranded cDNA molecule was generated using DNA Polymerase I and DNA Ligase. The cDNA will then be purified and concentrated using a phenol:chloroform extraction followed by ethanol precipitation. The cDNA products will then be incubated with T7 RNA Polymerase and biotinylated ribonucleotides using an In Vitro Transcription kit (Enzo Diagnostics). One-half of the cRNA product was purified using an RNeasy column (Qiagen) and quantified with a spectrophotometer. The cRNA target (20 ug) was incubated at 94° C. for 35 minutes in fragmentation buffer (Tris, MgOAc, KOAc). The fragmented cRNA was diluted in hybridization buffer (MES, NaCl, EDTA, Tween 20, Herring Sperm DNA, Acetylated BSA) containing biotin-labeled OligoB2 and Eukaryotic Hybridization Controls (Affymetrix). The hybridization cocktail was denatured at 99° C. for 5 minutes, incubated at 45° C. for 5 minutes and then injected into a GeneChip® cartridge. The GeneChip® array was incubated at 42° C. for at least 16 hours in a rotating oven at 60 rpm, GeneChips® were washed with a series of nonstringent (25° C.) and stringent (50° C.) solutions containing variable amounts of MES, Tween20 and SSPE. The microarrays will then be stained with Streptavidin Phycoerythrin and the fluorescent signal was amplified using a biotinylated antibody solution. Fluorescent images were detected in a GeneChip® Scanner 3000 and expression data was extracted using the GeneChip® Operating System v 1.1 (Affymetrix). All GeneChips® were scaled to a median intensity setting of 500. Gene expression levels were compared between biopsy samples taken from the control distal pulmonary vasculature (baseline LPA and RPA) and PAH distal pulmonary arteries (surgical shunt LPA).

Gene Expression Analysis

After RNA preparation, array hybridization and scanning of the Porcine GeneChips® exactly as recommended by Affymetrix, the data produced are processed using the Affymetrix tools in the R-Eioconductor package called /Affy/. This tool set allows for various probe level analyses of the data as well as probe level quality control. The MASS algorithm was used, taking into account both the MM and PM probe data, and generating "Present" or "Absent" calls for each gene on each chip. If boxplots of the porcine probe level data reveal that any of the hybridizations are of low quality, the data from these chips was removed from any downstream analysis. MASS with the non-linear Quantiles normalization (Affy package/normalize.quantiles)/ was used with this data set to produce data almost free of artificial correlations. The Present/Absent calls are also used to remove from the analysis the genes that were never expressed in any of the samples examined (this is analogous to using a P-value for gauging a gene's data quality on a chip, and then filtering).

Based on the first dozen chips processed, after normalization and quality control ~19,000 genes were moved on to the next stage of the analysis. The commercial package GeneSpring was used to assess differential gene expression and perform tests using clustering algorithms. Thus far, hierarchical clustering has revealed that the time-point replicates have the greatest similarity to one another.

Gene expression fold changes for 7, 21 60 and 180 days post-surgery relative to baseline were then loaded into GSEA (gene set enrichment analysis) or specially written PERL scripts which carry out KS (Kolmogorov-Smirnov) statistical analysis in order to identify novel therapeutic candidates.

Novel Therapeutic Identification

During PAH the best therapeutic targets are those which are upregulated as the disease state progresses. Thus drugs which are known to counter the action of any upregulated genes and their products would be of the greatest potential therapeutic value. Therefore, lists of upregulated genes were then matched to drugs which target their gene products.

In addition, many drugs interact with multiple targets in the body's tissues. Lists of the targets (called genesets) for each of ~2000 characterized drugs were obtained from the literature and online databases. These genesets were then used to search for drugs which would be most likely to have therapeutic value in PAH.

This was done by using KS statistics which computes the Kolmogorov-Smirnov score for a geneset for a particular drug within an ordered list. The KSscore task is used to examine the enrichment of a set of genes at the top of an ordered list. The KS score is high when the tags appear early (i.e. near the top) of the ordered list. The significance of the KS score for a particular test may be examined by computing KS scores for multiple sets of X query genes selected at random from the dataset (note that the KS score is not independent of the number of members of the query gene set). Using this approach we were able to identify in our messenger RNA expression dataset drugs which are currently used as therapeutics for PAH (see FIG. 1A). Importantly, using the same approach we were also able to identify additional potential therapeutics, within the existing pool of characterized drugs. This process identified existing drugs as novel therapeutics for PAH.

Example II

Gene Expression Analysis from Porcine Animal Model Data

Gene Expression Analysis

The porcine studies indicate that single endoarterial biopsy samples obtained in the porcine model of surgical shunt PAH contain sufficient RNA for microarray analysis, as we were able to analyze the mRNAs in whole genome porcine microarrays. We obtained endoarterial biopsies and measured pulmonary arterial pressure (PAP) at baseline prior to surgery, and at approximately 7, 21, 60 and 180 days post-PAH surgery from several animals. Porcine whole genome expression values were obtained for biological replicates with 2 samples from each time point. These replicates produced 5 sets of high quality replicated expression data (baseline, day 7, day 21, day 60 and day 180; see Table 1 for PAP data). Downstream data analysis was carried out using commercial (Ingenuity; GeneSpring) and free/open source software (R; Bioconductor; GSEA). Mean expression values were obtained for each gene by averaging the gene expression values of the two biopsies at each timepoint. The resulting gene expression mean values were used to calculate fold changes between day 7, 21, 60 and day 180 gene expression relative to baseline.

Validity of the model was confirmed by examining the gene expression changes for selected genes previously found to be dysregulated in PAH (Table 2). Endothelin 1 and protein-tyrosine kinase Tie2 both displayed upregulation in accordance with explanted tissue from IPAH transplant recipients (Dewatcher et al 2006), and platelet-derived growth factor receptor alpha, serotonin receptors 2B and 1D, calmodulin, transcription factor STAT5b, voltage-dependent anion channels 1, 2 and 3, and RAS p21 protein activator 1 also increased in our model while tumor necrosis factor and plasminogen activator inhibitor-1 were found to be downregulated in our model in a similar fashion with IPAH explant tissue results (Fantozzi et al 2005). Survivin was upregulated in our model in a similar fashion to published findings (McMurtry et al 2005), and FYN and VAV-1 oncogenes, requiem homolog, inward rectifier K+ channel, and chloride channel 1 also increased while DEAD/H box polypeptide 3 and angiopoetin 1 displayed decreased expression in agreement with patient findings (Geraci et al 2001). We also observed decreased expression of peroxisome proliferator-activated receptor gamma (Ameshima et al 2003), and downregulated vascular endothelial growth factor B (Louzier et al 2003) in correspondence with previous results. The concordance between genes previously found to be aberrant in published PAH studies and altered gene expression in our model attest to the validity and potential usefulness of gene expression data derived from endoarterial biopsies. The time dependent nature of gene expression dysregulation found in our model further demonstrates the utility of obtaining endoarterial biopsies at multiple time points in PAH progression.

While several of these genes have been previously associated with PAH (for example, KCBN1, CASP3, TLR4, IL1B, IL6, HMGCR, TOF1, FYN, PRKCA, EDNRB, PDGFRA, and HRT2B), several have not (for example, HSPE, YES1, CFTR, MAOA, MAOB, and CACND21), raising the intriguing possibility that known existing drugs that target upregulated genes previously unassociated with PAH may be effective in treatment of the disease.

Example III

Identification of Dysregulated microRNA During the Progression of PAH

Endoarterial biopsy samples percutaneously obtained during the progression of PAH were analyzed to correlate changes in microRNA expression to disease progression.
microRNA Expression Data Analysis Data analysis was done in three stages. First, expression intensities were calculated for each miRNA probed on the array for all hybridizations (12 in total) using illumine's Beadstudio Version 3.0 software. Second, intensity values were quality controlled and normalized: quality control was carried out by using the illumina Beadstudio detection P-value set to <0.05 as a cutoff. This removed miRNAs which were effectively absent from the arrays (that is, were never detected). After this step, the initial 1145 miRNAs were reduced to 1094. All the arrays were then normalized using the normalize.quantiles routine from the Affy package in Bioconductor. This procedure accounted for any variation in hybridization intensity between the individual arrays Finally, these normalized data were imported into GeneSpring and analysed for differentially expressed miRNAs. The groups of biological replicates were described to the software and significantly differentially expressed genes determined on the basis of Welch t-tests and fold difference changes in expression level. The determination of miRNA targets genes was done using a publicly available database of miRNA target sequences and a specially written PERL programming script.
miRNA Pressure Related Analysis The data was also looked at to reflect the stages of the disease (based on blood pressure and flow rates), as opposed to the time point or the individual pigs. Three groups were defined (1) Normal (baseline); (2) High Flow Low Pressure 'HFLP' and (3) High Flow High Pressure 'HFHP' (see Table 11). The groups were compared back to the baseline and the statistically significantly differentially regulated miRNAs determined (Tables 12, 13, 14 & 15).

Using illumina microRNA expression microarrays, fluctuations in the level of expression of ~1200 microRNAs were determined during the onset and progression of PAH. Porcine and Homo sapiens miRNA sequences are very often highly conserved. Expression comparisons were done on a timepoint basis, taking in account the available replicates and the statistical significance of the expression changes. The data was also looked at to reflect the stages of the disease (based on blood pressure and flow rates), as opposed to the time point or the individual pigs. Three groups were defined (1) Normal (baseline); (2) High Flow Low Pressure 'HELP' and (3) High Flow High Pressure 'HFHP'. The groups were compared back to the baseline and the statistically significantly differentially regulated miRNAs determined.
Finding Micro RNAs with Potential as Therapeutic Targets The messenger RNA expression data set was analysed looking for expression changes in sets of genes with known target sites for particular miRNAs. miRNAs are known to negatively regulate gene expression at the level of translation by binding to upstream regions of mRNA and blocking events required for translation of the mRNA into protein. This was again done using Gene Set Enrichment Analysis (GSEA) and the publicly available miRNA genesets. "Cross-talk" is seen between the messenger RNA gene expression changes and the microRNA expression changes. The messenger RNA expression analysis directly revealed the differential expression of groups of genes competent to be regulated by these miRNA.

Example IV

Personalizing Therapeutic Regimens for Vascular-Based Diseases

The use of gene expression data to shape individual drug therapies has been postulated as the next phase in personalized medicine. The bioinformatic processing of an individual's gene expression data can be used to generate a ranked list of therapies suitable for that individual. PAH disease pathology varies greatly over time, and is also likely to be specific for particular individuals. The analysis of the RNA in the PAH biopsy samples allows therapies to be tailored to the individual at that particular stage of the diseases progression.

The genes and biochemical pathways changing the most at the level of gene expression can be determined by comparing the PAH biopsy samples to a baseline control of normal healthy vasculature tissue. Observations show time-dependent extensive changes in gene expression with the progression of PAH. Known targets for approved PAH therapeutics can be seen Up-regulated in the diseased state.

Drug therapies can be ranked by using the known targets of drugs as genesets. These drug signature lists can then be used in a process such as Gene Set Enrichment Analysis, or KS statistics. KS Statistics returns a score for how well ranked a particular drug would be for a particular patient.

A drug is represented as the set of its known target genes; this can be in the dozens for some bioactive compounds. Genesets for ~2000 drugs were assembled. KS Statistics yields a value ('KS score') representing the positional distribution of the set of query genes (here, the drug targets) within an ordered list of genes (genes induced in PAH). The ordered list is produced by looking at the fold change in a mRNAs expression between time X and the baseline, and sorting on this value. The gene with the greatest fold change is ranked as #1, second greatest fold change is ranked as #2, etc. KS score is computed in accordance with the Kolmogorov-Smirnov non-parametric rank statistic where X is the number of genes in the query gene set, Z is the number of genes in the ordered list, and $Y=Z-X$. A suitable baseline is generated using gene expression from artery samples from non-diseased controls. These samples can be obtained surgically, percutaneously or post-mortem.

This process can be repeated for all the PAH time points and the resulting table of KS scores for each drug hierarchically clustered. This reveals which drugs are potentially of the greatest therapeutic value for a patient.

This supports the idea of achieving personalized treatments for vascular-based diseases by generating individualized drug prescriptions based on the bioinformatic processing of gene expression data from endoarterial biopsy samples obtained from diseased arteries. Similarly, this enables personalized treatments for vascular-based diseases by generating lists of dysregulated microRNA from the bioinformatic processing of microRNA expression data from endoarterial biopsy samples from diseased arteries.

TABLE 1

Pulmonary arterial pressures obtained during endoarterial biopsy catheterization for biopsy samples used in microarray analysis.

| Biopsy Sample | Pulmonary Arterial Pressure mmHg | | |
|---|---|---|---|
| | Systolic | Diastolic | Mean |
| Baseline Pig #9 | 22 | 11 | 17 |
| Baseline Pig #10 | 25 | 16 | 18 |
| Day 21 Pig #2 | 95 | 66 | 82 |
| Day 21 Pig #6 | 41 | 26 | 33 |
| Day 60 Pig #6 | 87 | 59 | 74 |
| Day 60 Pig #5 | 49 | 27 | 38 |

TABLE 2

Selected genes previously associated with PAH similarly dysregulated in the porcine model.

| Gene Symbol | Name | Baseline | Day 7 | Day 21 | Day 60 | Day 180 | Fold Change Day 7/Base | Fold Change Day 21/Base | Fold Change Day 60/Base | Fold Change Day 180/Base |
|---|---|---|---|---|---|---|---|---|---|---|
| VAV1 | vav 1 oncogene | 32.56 | 21.65 | 237.16 | 138.29 | 15.39 | −1.50 | 7.28 | 4.25 | −2.12 |
| RASA1 | RAS p21 protein activator 1 | 73.23 | 388.68 | 280.27 | 704.56 | 361.25 | 5.31 | 3.83 | 9.62 | 4.93 |
| TIE2 | protein-tyrosine kinase Tie2 | 20.92 | 2.59 | 32.46 | 702.68 | 218.34 | −8.08 | 1.55 | 33.59 | 10.44 |
| FYN | fyn proto-oncogene | 43.33 | 180.38 | 404.77 | 531.03 | 166.17 | 4.16 | 9.34 | 12.26 | 3.83 |
| VDAC1 | voltage-dependent anion channel 1 | 1176.57 | 2350.33 | 6629.76 | 3144.14 | 2277.10 | 2.00 | 5.63 | 2.67 | 1.94 |
| PDGFRA | platelet-derived growth factor receptor alpha | 69.46 | 152.75 | 10.45 | 611.81 | 18.80 | 2.20 | −6.64 | 8.81 | −3.69 |
| 5-HT2B | serotonin 2B receptor | 49.96 | 19.03 | 166.45 | 142.91 | 488.77 | −2.63 | 3.33 | 2.86 | 9.78 |
| KCNJ2 | inwardly rectifying potassium channel KIR6.1 | 389.66 | 83.23 | 1059.11 | 212.29 | 84.28 | −4.68 | 2.72 | −1.84 | −4.62 |
| 5-HT1D | serotonin 1D receptor | 14.17 | 42.48 | 8.32 | 61.48 | 4.95 | 3.00 | −1.70 | 4.34 | −2.86 |
| DPF2 | requiem, apoptosis response zinc finger gene | 140.95 | 123.89 | 140.90 | 195.55 | 93.92 | −1.14 | −1.00 | 1.39 | −1.50 |
| VDAC2 | Voltage-dependent anion channel 2 | 5683.09 | 2665.62 | 1620.37 | 4940.32 | 3643.38 | −2.13 | −3.51 | −1.15 | −1.56 |
| STAT5B | signal transducer and activator of transcription 5b | 469.40 | 571.47 | 1327.53 | 808.09 | 626.07 | 1.22 | 2.83 | 1.72 | 1.33 |
| AGPT | angiopoietin 1 | 17.825026 | 50.240685 | 11.806807 | 70.12715 | 3.4479218 | 2.82 | −1.51 | 3.93 | −5.17 |
| BIRC5 | apoptosis inhibitor survivin | 169.33 | 751.37 | 140.45 | 31.26 | 44.69 | 4.44 | −1.21 | −5.42 | −3.79 |
| VDAC3 | voltage-dependent anion channel 3 | 4092.99 | 750.86 | 5013.26 | 959.72 | 2018.55 | −5.45 | 1.22 | −4.26 | −2.03 |
| PLANH1 | plasminogen activator inhibitor I | 27760.742 | 43007.71 | 23685.375 | 28771.838 | 36086.305 | 1.55 | −1.17 | 1.04 | 1.30 |
| PPARG | peroxisome proliferator-activated receptor gamma 2 | 177.80 | 12.86 | 18.96 | 194.20 | 62.40 | −13.83 | −9.38 | 1.09 | −2.85 |
| CALM1 | Calmodulin | 3092.78 | 2436.23 | 867.25 | 1401.38 | 2252.81 | −1.27 | −3.57 | −2.21 | −1.37 |
| APOE | apolipoprotein E | 358.91 | 206.34 | 94.35 | 129.60 | 288.79 | −1.74 | −3.80 | −2.77 | −1.24 |

TABLE 3

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| Ssc.11018.1.A1_at | Mitogen-activated protein kinase 14 | 19.80 | −5.02 | −17.27 | −20.43 | MAPK14 | SCIO-469, RO-3201195 |
| Ssc.15986.1.S1_at | Insulin receptor | 29.28 | −16.85 | −17.70 | −19.01 | INSR | insulin, insulin aspart, insulin glulisine, insulin lispro, insulin glargine |
| Ssc.873.1.S1_at | Cell division control protein 2 | 27.38 | −2.37 | −4.66 | −7.76 | CDC2 | flavopiridol |
| Ssc.29928.1.A1_at | Histone deacetylase 11 (HD11) | 21.56 | −3.17 | −2.91 | −10.50 | HDAC11 | tributyrin, FXD101, pyroxamide, vorinostat, FR901228 |
| Ssc.100.1.S1_at | Tumor necrosis factor precursor (TNF-alpha) | 18.41 | −1.70 | −9.62 | −3.15 | TNF | adalimumab, etanercept, infliximab, CDF870, golimumab, thalidomide |
| Ssc.19672.1.S1_at | RAC-alpha serine/threonine-protein kinase | 17.77 | 1.25 | −19.62 | −2.11 | AKT1 | enzastaurin |
| Ssc.14475.3.S1_a_at | Peroxisome proliferator activated receptor gamma (PPAR-gamma) | 13.83 | −9.38 | 1.09 | −2.85 | PPARG | rosiglitatone, GI262570, pioglitozone, tesaglitazar, troglitazone |
| Ssc.14326.1.A1_at | Mitogen-activated protein kinase 13 | 12.63 | 1.56 | −1.80 | −7.24 | MAPK13 | SCIO-469 |
| Ssc.25843.1.S1_at | Chloride channel protein 2 (ClC-2) | 11.77 | −17.04 | −21.97 | −9.92 | CLCN2 | lubiprostone |
| Ssc.16201.1.A1_at | Metabotropic glutamate receptor | 10.79 | −35.68 | −33.34 | −47.92 | GRM7 | fasoracetam |
| Ssc.11381.1.S1_at | Interferon-alpha/beta receptor alpha chain | 10.45 | 8.08 | 2.61 | −1.30 | IFNAR1 | interferon beta-1a, interferon alfa-2b, interferon alfacon-1, PEG-interferon alfa-2a, interferon alfa-2a/ribavirin, pegintron, interferon beta-1b, IFNA2A |
| Ssc.5371.1.S1_a_at | DNA polymerase epsilon subunit B (DNA polymerase II subunit B) | 10.16 | 1.68 | −1.37 | −3.14 | POLE2 | gemcitabine |
| Ssc.14471.1.S1_at | B-lymphocyte antigen CD19 | 9.54 | 3.30 | −10.32 | 3.04 | CD19 | combotox, HD37-dgRTA, MT103 |
| Ssc.24856.1.A1_at | phosphodiesterase 11A; cyclic nucleotide phosphodiesterase 11A1 | 9.36 | −2.70 | −3.68 | −2.68 | PDE11A | dyphylline, nitroglycerin, aminophylline, dipyridamole, tolbutamide, tadalafil, theophylline, pentoxifylline |
| Ssc.189.1.S1_at | Diacylglycerol O-acyltransferase 1 | 9.16 | −4.21 | −36.07 | −24.06 | DGAT1 | omacor |
| Ssc.16186.1.S1_at | T-cell surface glycoprotein CD3 epsilon | 9.00 | 3.12 | 2.12 | −5.66 | CD3E | visilizumab, MT103, muromonab-CD3 |
| Ssc.15601.1.A1_s_at | Interleukin-1 beta precursor (IL-1 beta) | 8.18 | 4.65 | −14.71 | −2.84 | IL1B | IL-1 trap |
| Ssc.5538.1.S1_at | Carbonic anhydrase II (Carbonate dehydratase II) (CA-II) (Carbonic anhydrase C)] | 8.09 | 1.39 | −2.25 | −1.35 | CA2 | methazolamide, hydrochlorothiazide, acetazolamide, trichloromethiazide, dorzolamide, chlorothiazide, dorzolamide/timolol, brinzolamide, chlorthalidone, benzthiazide, sulfacetamide, topiramate |
| Ssc.113.1.S1_at | Interleukin-1 alpha (IL-1 alpha) | 8.01 | −2.65 | −1.59 | −7.73 | IL1A | IL-1 trap |
| Ssc.2895.1.S1_at | Serine/threonine-protein kinase | 7.48 | −2.02 | −2.45 | −1.81 | AURKB | AZD-1152 |
| Ssc.8219.1.A1_at | Histone deacetylase 8 (HD8) | 7.21 | −2.18 | −12.09 | −29.63 | HDAC8 | tributyrin, PXD101, pyroxamide, vorinostat, FR 901228 |
| Ssc.13473.1.A1_at | Ceramide glucosyltransferase | 7.13 | −2.88 | −4.17 | −6.14 | UGCG | N-butyldeoxygalactonojirimycin, N-butyldeoxynojirimycin |
| Ssc.14129.1.A1_at | 4-aminobutyrate aminotransferase, mitochondrial (GABA transaminase) | 6.91 | 2.56 | −21.17 | −3.35 | ABAT | valproic acid |
| Ssc.15379.1.S1_at | diacylglycerol O-acyltransferase homolog 2; GS1999full | 6.60 | −1.51 | −3.49 | −2.13 | DGAT2 | omacor |
| Ssc.15830.1.A1_at | Retinoic acid receptor beta | 6.60 | −3.28 | −1.83 | −1.10 | RARB | etretinate, adapalene, 13-cis-retinoic acid, tazarotene, acitretin, retinoic acid, 9-cis-retinoic acid, fenretinide |
| Ssc.17928.1.A1_at | helicase (DNA) B; helicase B | 6.40 | −2.65 | −4.38 | −1.06 | HELB | epirubicin |

TABLE 3-continued

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| Ssc.19673.1.S1_at | T-cell surface glycoprotein CD3 delta | 6.40 | 2.70 | 2.03 | −11.77 | CD3D | visilizumab, MT103 |
| Ssc.17222.1.A1_at | mucin 1, transmembrane; | 6.31 | −6.10 | −5.94 | −13.48 | MUC1 | HuHMFG1 |
| Ssc.55.1.S1_at | Epidermal growth factor receptor | 6.09 | −5.46 | −4.68 | −4.52 | EGFR | cetuximab, AEE 788, panitumumab, BMS-599626, ARRY-334543, XL647, canertinib, gefitinib, HKI-272, PD 153035, lapatinib, vandetanib, erlotinib |
| Ssc.19059.1.A1_at | Type-1 angiotensin II receptor (AT1) (AT1AR | 5.57 | −2.57 | 1.50 | −11.08 | AGTR1 | amlodipine/olmesartan medoxomil, losartan/hydrochlorothiazide, valsartan/hydrochlorothiazide, candesartan cilexetil, olmesartan medoxomil, irbesartan, losartan potassium, telmisartan, eprosartan, candesartan cilexetil/hydrochlorothiazide, hydrochlorothiazide/irbesartan, eprosartan/hydrochlorothiazide, hydrochlorothiazide/telmisartan, hydrochlorothiazide/olmesartan medoxomil, valsartan |
| Ssc.16162.1.S1_at | 4-hydroxyphenylpyruvate dioxygenase | 5.43 | −8.93 | −8.65 | −3.84 | HPD | nitisinone |
| Ssc.27603.1.S1_at | Endothelin B receptor | 5.30 | −3.27 | 15.99 | 1.23 | EDNRB | bosentan, sitaxsentan, atrasentan |
| Ssc.16333.1.A1_at | Multidrug resistance protein 1 | 4.94 | −2.99 | −3.50 | −22.89 | ABCB1 | XR9576, OC 144-093, valspodar |
| Ssc.12769.1.A1_at | Amiloride-sensitive cation channel 1, neuronal | 4.82 | −13.74 | −9.59 | −10.72 | ACCN1 | amiloride, amiloride/hydrochlorothiazide |
| Ssc.17155.1.At_at | heparanase; heparanase-1 | 4.81 | 5.38 | 2.98 | −1.83 | HPSE | heparanase inhibitor PI-88 |
| Ssc.15933.1.S1_s_at | Cytotoxic T-lymphocyte protein 4 (Cytotoxic T-lymphocyte-associated antigen 4) (CTLA-4) (CD152 antigen) | 4.76 | −5.14 | −6.63 | −26.39 | CTLA4 | ipilimumab, ticilimumab |
| Ssc.15965.1.S1_at | Inward rectifier potassium channel 2 (IRK1) | 4.68 | 2.72 | −1.84 | −4.62 | KCNJ2 | nicorandil, amiodarone |
| Ssc.26351.1.S1_at | cAMP-specific 3',5'-cyclic phosphodiesterase 4D | 4.67 | 4.99 | 3.61 | −1.15 | PDE4D | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.15990.1.A1_at | Retinoic acid receptor RXR-alpha | 4.42 | −4.18 | −18.45 | −24.58 | RXRA | bexarotene, retinoic acid, 9-cis-retinoic acid |
| Ssc.2605.1.A1_at | Protein farnesyltransferase beta | 4.39 | −2.62 | −7.00 | −2.74 | FNTB | lonafarnib, tipifarnib |
| Ssc.30373.1.A1_at | cGMP-specific 3',5'-cyclic phosphodiesterase | 4.27 | 1.52 | 2.34 | 4.09 | PDE5A | dyphylline, nitroglycerin, DA-8159, aminophylline, sildenafil, dipyridamole, aspirin/dipyridamole, vardenafil, tolbutamide, tadalafil, theophylline, pentoxifylline |
| Ssc.19233.1.S1_at | Collagen alpha 2(IX) chain | 4.23 | −1.14 | −22.83 | −2.12 | COL9A2 | collagenase |
| Ssc.1147.1.A1_at | Lipoprotein lipase | 4.05 | −5.49 | 3.78 | −8.08 | LPL | nicotinic acid, lovastatin/niacin |
| Ssc.13160.1.A1_at | Voltage-dependent L-type calcium channel alpha-1F subunit | 4.03 | −4.75 | −1.11 | −2.77 | CACNA1F | MEM-1003, mibefradil, bepridil, nisoldipine, isradipine, nicardipine |
| Ssc.12748.1.A1_at | Catechol O-methyltransferase, membrane-bound form | 4.03 | −3.20 | −5.82 | −21.93 | COMT | carbidopa/entacapone/levodopa, BIA-3-202, tolcapone, entacapone |
| Ssc.24986.1.S1_at | Aldehyde dehydrogenase 1A1 | 4.00 | −3.76 | −2.17 | −9.20 | ALDH1A1 | disulfiram, chlorpropamide |
| Ssc.15972.1.S1_at | Peroxisome proliferator activated receptor delta (PPAR-delta) | 3.83 | −1.07 | −2.73 | −1.60 | PPARD | GW501516 |
| Ssc.24509.1.A1_at | Gamma-aminobutyric-acid receptor pi subunit | 3.76 | −1.28 | −1.98 | −1.23 | GABRP | alphadolone, sevoflurane, isoflurane, isoniazid, |

TABLE 3-continued

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| | | | | | | | felbamate, etomidate, halothane, fluoxetine/olanzapine, eszopiclone, zolpidem, lorazepam, olanzapine, zaleplon, secobarbital, phenobarbital, pentobarbital, desflurane, methoxyflurane, enflurane |
| Ssc.7176.1.A1_at | C—X—C chemokine receptor type 4 (CXC-R4) ( | 3.74 | 10.91 | 8.15 | 1.68 | CXCR4 | JM 3100 |
| Ssc.6570.1.S1_at | Delta-aminolevulinic acid dehydratase] | 3.71 | −3.43 | −3.05 | −1.66 | ALAD | delta-aminolevulinic acid |
| Ssc.17485.1.S1_at | Guanylate cyclase soluble, alpha-2 chain | 3.57 | −38.82 | −1.77 | −7.04 | GUCY1A2 | nitroglycerin, isosorbide-5-mononitrate, isosorbide dinitrate, nitroprusside, isosorbide dinitrate/hydralazine |
| Ssc.26200.1.S1_at | Thyroid hormone receptor beta-1 | 3.49 | −1.56 | 7.96 | 2.52 | THRB | 3,5-diiodothyropropionic acid, amiodarone, thyroxine, L-triiodothyronine |
| Ssc.9595.1.S1_at | Beta platelet-derived growth factor receptor | 3.48 | −3.60 | 1.40 | 1.65 | PDGFRB | dasatinib, sunitinib, axitinib, KRN-951, imatinib, sorafenib, becaplermin |
| Ssc.108.1.S1_at | Oxytocin receptor (OT-R) | 3.44 | −8.53 | −16.69 | −4.47 | OXTR | TT-235 |
| Ssc.15801.1.A1_at | Protein kinase C, beta | 3.36 | 6.36 | 3.53 | −4.98 | PRKCB1 | enzastaurin, ruboxistaurin |
| Ssc.27928.1.S1_at | Opioid growth factor receptor (OGFr) | 3.34 | −3.33 | −2.89 | −3.51 | OGFR | enkephalin, methionine |
| Ssc.12791.1.A1_at | 3-hydroxy-3-methylglutaryl-coenzyme A reductase (HMG-CoA reductase | 3.27 | 2.77 | 1.77 | −2.56 | HMGCR | aspirin/pravastatin, lovastatin/niacin, ezetimibe/simvastatin, amlodipine/atorvastatin, fluvastatin, cerivastatin, atorvastatin, pravastatin, simvastatin, lovastatin, rosuvastatin |
| Ssc.7933.1.A1_at | Cell division protein kinase 8 | 3.26 | −1.63 | −1.78 | −3.05 | CDK8 | flavopiridol |
| Ssc.11147.1.S1_at | Aldehyde dehydrogenase, mitochondrial (ALDH class 2) (ALDHI) (ALDH-E2) | 3.18 | 1.13 | 2.00 | −1.68 | ALDH2 | disulfiram, chlorpropamide |
| Ssc.19608.1.S1_at | Retinoic acid receptor RXR-gamma | 3.15 | −1.39 | −1.73 | −3.19 | RXRG | bexarotene, retinoic acid, 9-cis-retinoic acid |
| Ssc.29260.1.A1_at | Granulocyte colony stimulating factor receptor (G-CSF-R) (CD114 antigen)] | 3.15 | −2.50 | −4.36 | −4.68 | CSF3R | pegfilgrastim, filgrastim |
| Ssc.22797.1.S1_at | DNA topoisomerase II, beta isozyme | 3.15 | −1.87 | 1.02 | −2.91 | TOP2B | novobiocin, etoposide, CPI-0004Na, pixantrone, becatecarin, elsamitrucin, AQ4N, BN 80927, tafluposide, mitoxantrone, norfloxacin, dexrazoxane, tirapazamine, TAS-103, XK469, gatifloxacin, valrubicin, gemifloxacin, moxifloxacin, nemorubicin, nalidixic acid, epirubicin, doxorubicin, daunorubicin |
| Ssc.16121.1.A1_at | Corticotropin releasing factor receptor 1 | 3.03 | −4.50 | −17.00 | −4.36 | CRHR1 | Crh, CRA0165, CRA1001, SSR125543A |
| Ssc.12630.1.A1_at | Sodium/potassium-transporting ATPase alpha-1 chain | 2.97 | 2.81 | −7.30 | −2.03 | ATP1A1 | digoxin, omepratole, ethacrynic acid, perphenazine |
| Ssc.13254.1.A1_at | Metabotropic glutamate receptor 8 | 2.95 | −15.40 | −9.66 | −3.57 | GRM8 | fasoracetam |
| Ssc.30888.1.S1_at | Voltage-dependent L-type calcium channel alpha-1D | 2.92 | −2.72 | 1.90 | −7.82 | CACNA1D | MEM-1003, mibefradil, bepridil, nisoldipine, isradipine, nicardipine |
| Ssc.9565.1.S1_at | Interferon-gamma receptor alpha | 2.92 | 1.63 | 1.41 | −1.23 | IFNGR1 | interferon gamma-1b |
| Ssc.15880.1.S1_at | Cysteinyl leukotriene receptor 2 (CysLTR2) | 2.86 | 1.14 | −2.12 | −3.42 | CYSLTR2 | montelukast, zafirlukast |
| Ssc.2753.1.S1_at | Serine/threonine-protein kinase PLK1 | 2.77 | −4.42 | −7.50 | −4.52 | PLK1 | BI 2536 |
| Ssc.16123.1.A1_at | cAMP-specific 3′,5′-cyclic phosphodiesterase 4A | 2.75 | −3.97 | −3.49 | −1.46 | PDE4A | arofylline, tetomilast, LB69298, anagrelide, cilomilast, |

TABLE 3-continued

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| | | | | | | | milrinone, rolipram, L-826,141, amrinone, roflumilast, pentoxifylline, caffeine |
| Ssc.11383.1.A1_at | Glutamate receptor 3 | 2.61 | 1.85 | −1.87 | −2.43 | GRIA3 | talampanel, Org 24448, LY451395, tezampanel |
| Ssc.14403.1.S1_at | Sodium/potassium-transporting ATPase alpha-2 chain | 2.61 | −1.95 | −8.51 | −6.43 | ATP1A2 | digoxin, omeprazole, ethacrynic acid, perphenazine |
| Ssc.21754.1.A1_at | Collagen alpha 1(VI) chain | 2.57 | −47.00 | −5.79 | −4.37 | COL6A1 | collagenase |
| Ssc.6498.1.A1_at | Mitogen-activated protein kinase 12 (Mitogen-activated protein kinase p38 gamma) | 2.41 | −10.79 | −5.78 | −3.26 | MAPK12 | SCIO-469 |
| Ssc.16167.1.S1_at | Rho-associated protein kinase 1 | 2.40 | 2.32 | 2.83 | 3.00 | ROCK1 | fasudil, Y-27632 |
| Ssc.12781.1.A1_at | Toll-like receptor 4 | 2.39 | 1.83 | −1.52 | −6.10 | TLR4 | TAK-242 |
| Ssc.29366.1.A1_at | DNA topoisomerase I | 2.37 | −2.30 | −2.87 | −10.72 | TOP1 | elsamitrucin, T 0128, CT-2106, BN 80927, tafluposide, TAS-103, beta-lapachone, irinotecan, topotecan, 9-amino-20-camptothecin, rubitecan, gimatecan, karenitecin |
| Ssc.14485.1.S1_at | Parathyroid hormone/parathyroid hormone-related peptide receptor | 2.28 | −1.62 | −3.40 | −6.83 | PTHR1 | teriparatide |
| Ssc.12238.1.A1_at | Cysteinyl leukotriene receptor 1 (CysLTR1) | 2.28 | −1.73 | −1.34 | −6.96 | CYSLTR1 | zeneca ZD 3523, montelukast, zafirlukast |
| Ssc.3607.1.S1_at | Interferon-alpha/beta receptor beta chain | 2.28 | 4.65 | 1.11 | −1.56 | IFNAR2 | interferon beta-1a, interferon alfa-2b, interferon alfacon-1, PEG-interferon alfa-2a, interferon alfa-2a/ribavirin, pegintron, interferon beta-1b, IFNA2A |
| Ssc.2548.1.S1_at | DNA polymerase epsilon p17] | 2.27 | 1.93 | −1.67 | −1.21 | POLE3 | gemcitabine |
| Ssc.19706.1.A1_at | Mitogen-activated protein kinase 8 | 2.25 | −4.27 | −2.31 | −4.98 | MAPK8 | aplidine |
| Ssc.15382.1.S1_at | Cannabinoid receptor 2 (CB2) (CB-2) (CX5) | 2.22 | 3.48 | −1.37 | −4.69 | CNR2 | BAY 38-7271, delta-9-tetrahydrocannabinol |
| Ssc.4756.1.A1_at | Adenosine A3 receptor | 2.15 | 2.10 | 1.88 | −1.81 | ADORA3 | adenosine, dyphylline, aminophylline, clofarabine, theophylline, caffeine |
| Ssc.23261.1.A1_at | Trifunctional purine biosynthetic protein adenosine-3 | 2.15 | −3.54 | −3.66 | −5.67 | GART | LY231514 |
| Ssc.27293.1.A1_at | Hypoxanthine-guanine phosphoribosyltransferase | 2.15 | −1.16 | 1.63 | −7.14 | HPRT1 | 6-mercaptopurine, thioguanine, azathioprine |
| Ssc.14476.1.S1_at | Interleukin-2 receptor alpha | 2.07 | −8.52 | −8.73 | −5.00 | IL2RA | LMB-2, daclizumab, basiliximab, aldesleukin, denileukin diftitox |
| Ssc.27232.1.S1_at | Succinate semialdehyde dehydrogenase, mitochondrial | 2.06 | 1.12 | −2.84 | −5.73 | ALDH5A1 | valproic acid |
| Ssc.10142.1.A1_at | Dihydropyrimidine dehydrogenase [NADP+] | 2.06 | 2.17 | 1.13 | −2.68 | DPYD | eniluracil |
| Ssc.1908.1.S1_at | FKBP-rapamycin associated protein (FRAP) | 1.99 | 1.13 | −1.88 | −1.46 | FRAP1 | AP23573, temsirolimus, tacrolimus, everolimus |
| Ssc.204.1.S1_at | Cytochrome P450 3A4 | 1.97 | −3.35 | 2.16 | −1.42 | CYP3A4 | ketoconazole |
| Ssc.18459.1.S1_at | Amiloride-sensitive sodium channel alpha- | 1.97 | −2.41 | 1.43 | −1.93 | SCNN1A | triamterene/hydrochlorothiazide, amiloride, amiloride/hydrochlorothiazide, triamterene |
| Ssc.24889.1.S1_at | Arachidonate 12-lipoxygenase, 12S-type | 1.97 | 2.83 | −1.18 | −2.78 | ALOX12 | sulfasalazine, balsalazide, 5-aminosalicylic acid, masoprocol, verteporfin |
| Ssc.15748.2.S2_at | T lymphocyte activation antigen CD80 | 1.95 | −1.24 | 1.54 | −3.12 | CD80 | abatacept |
| Ssc.5826.1.A1_at | Macrophage colony stimulating factor I receptor (CD115 antigen) | 1.93 | −4.97 | −13.18 | 1.61 | CSF1R | sunitinib |
| Ssc.15822.1.S1_at | Coagulation factor V | 1.92 | 3.76 | 1.89 | −1.75 | F5 | drotrecogin alfa |
| Ssc.9262.1.A1_at | Histamine H1 receptor | 1.91 | −4.10 | −3.91 | −1.86 | HRH1 | nitisinone |
| Ssc.62.2.S1_a_at | Interleukin-6 (IL-6) ( | 1.89 | −6.32 | 2.77 | −1.04 | IL6 | tocilizumab |
| Ssc.14258.1.S1_at | Amyloid beta A4 protein | 1.87 | 3.33 | 1.34 | −1.02 | APP | AAB-001 |
| Ssc.15878.1.S1_at | Serine/threonine protein phosphatase 2B | 1.85 | 3.22 | 3.62 | −1.49 | PPP3CA | ISAtx-247, tacrolimus, pimecrolimus, cyclosporin A |

TABLE 3-continued

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| Ssc.19379.1.A1_at | Voltage-dependent L-type calcium channel alpha-1C subunit | 1.83 | −1.34 | 1.07 | −3.27 | CACNA1C | clevidipine, MEM-1003, amlodipine/olmesartan medoxomil, amlodipine/benazepril, diltiazem, verapamil, mibefradil, bepridil, enalapril/felodipine, amlodipine/atorvastatin, nisoldipine, isradipine, felodipine, nimodipine, nitrendipine, amlodipine, nicardipine, nifedipine, trandolapril/verapamil, diltiazem/enalapril |
| Ssc.10215.1.A1_at | High-affinity cAMP-specific and IBMX-insensitive 3',5'-cyclic phosphodiesterase 8A | 1.83 | 1.12 | −8.48 | −15.51 | PDE8A | dyphylline, nitroglycerin, aminophylline, anagrelide, milrinone, dipyridamole, tolbutamide, theophylline, pentoxifylline |
| Ssc.20944.1.S1_at | Carbonic anhydrase XIV | 1.82 | −3.49 | −5.34 | −12.64 | CA14 | methazolamide, hydrochlorothiazide, acetazolamide, trichloromethiazide, chlorothiazide, chlorthalidone, benzthiazide, sulfacetamide, topiramate |
| Ssc.4125.1.A1_at | Histone deacetylase 5 (HD5) | 1.82 | −4.64 | −4.18 | −2.74 | HDAC5 | tributyrin, PXD101, pyroxamide, vorinostat, FR 901228 |
| Ssc.9272.1.S1_at | Tumor-associated calcium signal transducer 1 (EPCAM antigen) | 1.81 | 3.94 | 176.50 | 2.07 | TACSTD1 | tucotuzumab celmoleukin |
| Ssc.6301.1.S1_at | Aromatic-L-amino-acid decarboxylase | 1.76 | 1.80 | −4.91 | −1.88 | DDC | carbidopa/entacapone/levodopa, carbidopa/levodopa, S(−)-carbidopa, L-dopa |
| Ssc.15995.1.S1_at | Potassium voltage-gated channel subfamily E member 1 | 1.74 | −26.30 | −13.45 | −2.79 | KCNE1 | nicorandil, amiodarone, azimilide |
| Ssc.7581.1.A1_at | FL cytokine receptor precursor | 1.69 | 1.04 | −1.81 | 1.01 | FLT3 | CHIR-258, sorafenib, lestaurtinib, CGP 41251 |
| Ssc.26325.1.S1_at | Cystic fibrosis transmembrane conductance regulator (CFTR) | 1.60 | −5.71 | 4.77 | −8.99 | CFTR | SP 303 |
| Ssc.19691.1.S1_at | Platelet-activating factor acetylhydrolase | 1.59 | 1.16 | 3.01 | 1.47 | PLA2G7 | darapladib |
| Ssc.24714.1.A1_at | Excitatory amino acid transporter 2 (Sodium-dependent glutamate/aspartate transporter 2) | 1.58 | −2.29 | −7.61 | −3.45 | SLC1A2 | riluzole |
| Ssc.22477.1.S1_at | Collagen alpha 1(IV) chain | 1.58 | −5.08 | −1.78 | 1.04 | COL4A1 | collagenase |
| Ssc.227.1.S1_at | Potassium-transporting ATPase beta | 1.56 | −5.89 | −51.53 | −15.60 | ATP4B | ilaprazole, TAK-390MR, tenatoprazole, AGN 201904, AR-H047108, esomeprazole magnesium, omeprazole, lansoprazole, amoxicillin/clarithromycin/lansoprazole, rabeprazole, pantoprazole |
| Ssc.30147.1.A1_at | Fibroblast growth factor receptor 2 | 1.56 | 1.13 | −1.05 | −1.18 | FGFR2 | palifermin |
| Ssc.9523.1.A1_at | Methylated-DNA--protein-cysteine methyltransferase | 1.55 | −1.17 | 3.35 | 1.47 | MGMT | O6-benzylguanine |
| Ssc.26466.1.A1_at | Integrin beta-3 (CD61 antigen | 1.55 | −1.49 | −4.11 | −2.73 | ITGB3 | TP 9201, EMD121974, tirofiban |
| Ssc.5592.1.S1_at | Protein farnesyltransferase/geranylgeranyltraneferase type I alpha | 1.49 | −3.49 | −2.81 | −3.68 | FNTA | lonafarnib, tipifarnib |
| Ssc.17986.1.A1_at | Poly [ADP-ribose] polymerase-1 | 1.47 | −6.14 | −4.64 | −5.80 | PARP1 | INO-1001 |
| Ssc.11051.1.S1_at | Cell division protein kinase 4 | 1.44 | −7.67 | −4.96 | 23.75 | CDK4 | PD-0332991, flavopiridol |
| Ssc.20818.1.S1_at | Interleukin-2 receptor beta chain | 1.43 | 6.35 | −1.17 | −5.23 | IL2RB | humanized MiK-Beta-1, aldesleukin, denileukin diftitox |
| Ssc.16489.1.S1_at | Interleukin-7 receptor alpha chain | 1.42 | 2.34 | 1.86 | −6.31 | IL7R | recombinant human interleukin-7 |
| Ssc.10287.1.A1_at | Transforming growth factor beta 2 | 1.41 | −4.54 | 1.43 | 1.67 | TGFB2 | AP-12009 |

TABLE 3-continued

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| Ssc.14375.1.A1_at | ribonucleotide reductase M2 B | 1.40 | −2.19 | −5.17 | −2.28 | RRM2B | triapine, hydroxyurea |
| Ssc.16823.1.S1_at | P2Y purinoceptor 12 (P2Y12) (P2Y12 platelet ADP receptor) (P2Y(ADP)) | 1.38 | 1.19 | 1.41 | 1.11 | P2RY12 | prasugrel, AZD 6140 (Ticagrelor), clopidogrel |
| Ssc.11164.1.A1_at | DNA polymerase gamma subunit 1 | 1.37 | −1.33 | −3.67 | −3.60 | POLG | stavudine, vidarabine, zalcitabine |
| Ssc.10219.1.A1_at | Excitatory amino acid transporter 4 | 1.36 | 1.24 | −3.38 | −1.03 | SLC1A6 | riluzole |
| Ssc.3815.1.S1_at | RAC-beta serine/threonine-protein kinase | 1.35 | −3.13 | −3.28 | −3.19 | AKT2 | enzastaurin |
| Ssc.19619.1.S1_at | Proto-oncogene tyrosine-protein kinase LCK | 1.35 | −1.51 | −3.32 | −2.41 | LCK | dasatinib |
| Ssc.2926.1.S1_at | Heme oxygenase 2 | 1.34 | −1.43 | −4.13 | −1.81 | HMOX2 | tin mesoporphyrin |
| Ssc.11171.1.A1_at | Adenosine deaminase | 1.32 | −2.04 | −3.23 | 1.12 | ADA | pentostatin, vidarabine |
| Ssc.16621.1.A1_at | Excitatory amino acid transporter 3 | 1.27 | −7.18 | −3.04 | −8.29 | SLC1A1 | riluzole |
| Ssc.11549.1.A1_at | Dual specificity mitogen-activated protein kinase 1 | 1.25 | −33.67 | −11.33 | −6.48 | MAP2K1 | PD 0325901 |
| Ssc.6356.1.S1_at | Ornithine decarboxylase | 1.24 | −1.36 | −1.74 | −1.84 | ODC1 | tazarotene, eflornithine |
| Ssc.15999.1.A1_at | Vascular endothelial growth factor receptor 2 (VEGFR-2) | 1.24 | 1.24 | 18.52 | −11.02 | KDR | AEE 788, sunitinib, AZD 2171, pasopanib, XL647, CEP 7055, BMS-582664, KRN-951, vatalanib, sorafenib, vandetanib, pegaptanib |
| Ssc.9669.1.S1_at | Cell division protein kinase 5 | 1.21 | −2.68 | −17.06 | −1.65 | CDK5 | flavopiridol |
| Ssc.115.1.S1_s_at | Heme oxygenase 1 | 1.18 | −2.09 | −3.40 | −3.55 | HMOX1 | tin mesoporphyrin |
| Ssc.17224.1.S1_at | Toll-like receptor 8 | 1.17 | 6.49 | 3.13 | −1.52 | TLR8 | resiquimod |
| Ssc.8046.1.A1_at | peptidylprolyl, isomerase A isoform 1 | 1.16 | −1.08 | 1.39 | 1.26 | PPIA | M-methyl-4-Ile-cyclosporin |
| Ssc.7297.1.S1_at | Amine oxidase [flavin-containing] B (MAO-B) | 1.16 | 6.42 | 7.02 | −1.13 | MAOB | safinamide, ladostigil, rasagiline, selegiline, dextroamphetamine, procainamide, tranylcypromine, phenelzine, isocarboxazid, benzphetamine |
| Ssc.28329.1.S1_at | DNA polymerase beta | 1.14 | 1.19 | 1.07 | 5.25 | POLB | nelarabine, clofarabine, stavudine, trifluridine, vidarabine, ralcitabine, entecavir |
| Ssc.12202.2.S1_at | Farnesyl pyrophosphate synthetase | 1.12 | −1.26 | −2.68 | −1.13 | FDPS | YM 529, alendronic acid, pamidronic acid |
| Ssc.19700.1.S1_at | Serine/threonine protein phosphatase 2B catalytic subunit, beta | 1.11 | 1.13 | 1.34 | 1.09 | PPP3CB | ISAtx-247, tacrolimus, pimecrolimus, cyclosporin A |
| Ssc.8549.1.A1_at | Guanylate cyclase soluble, alpha-3 chain | 1.11 | 1.84 | −2.00 | −2.59 | GUCY1A3 | nitroglycerin, isosorbide-5-mononitrate, isosorbide dinitrate, nitroprusside, isosorbide dinitrate/hydralazine |
| Ssc.15374.1.S1_at | COL14A1 protein | 1.10 | −17.71 | 3.79 | 2.24 | COL14A1 | collagenase |
| Ssc.15901.1.S1_at | cGMP-inhibited 3′,5′-cyclic phosphodiesterase A | 1.10 | −13.33 | −3.16 | −1.41 | PDE3A | dyphylline, nitroglycerin, medorinone, aminophylline, cilostazol, dipyridamole, amrinone, tolbutamide, theophylline, pentoxifylline |
| Ssc.16000.1.A1_at | Vascular endothelial growth factor receptor 1 | 1.08 | −3.40 | 3.34 | 1.72 | FLT1 | sunitinib, axitinib, CEP 7055 |
| Ssc.20987.1.S1_at | Thrombopoietin receptor 1 | 1.06 | −1.58 | −3.97 | −5.87 | MPL | SB-497115 |
| Ssc.11149.1.A1_at | Carbonic anhydrase IX | 1.04 | −1.91 | −1.33 | −1.26 | CA9 | cG250, I 131 chimeric G250, Y 90 chimeric G250, methazolamide, hydrochlorothiazide, acetazolamide, trichloromethiazide, chlorothiazide, chlorthalidone, benzthiazide, sulfacetamide, topiramate |
| Ssc.8726.1.A1_at | Amidophosphoribosyltransferase | 1.03 | 1.24 | 4.16 | −1.11 | PPAT | 6-mercaptopurine, thioguanine, azathioprine |
| Ssc.11406.1.A1_a_at | Interleukin-1 receptor, type I | 1.03 | 2.70 | −2.44 | 1.42 | IL1R1 | anakinra |
| Ssc.14506.1.S1_at | DNA topoisomerase II, alpha | 1.01 | 3.80 | −1.18 | −14.30 | TOP2A | novobiocin, etoposide, CPI-0004Na, pixantrone, |

TABLE 3-continued

Day 7 prescription.

| Probe ID | Name | Fold Change D 7/ Base | Fold Change D 21/ Base | Fold Change D 60/ Base | Fold Change D 180/ Base | Gene Symbol | DRUGS |
|---|---|---|---|---|---|---|---|
| | | | | | | | becatecarin, elsamitrucin, AQ4N, EN 80927, tafluposide, mitoxantrone, norfloxacin, dexrazoxane, tirapazamine, TAS-103, gatifloxacin, valrubicin, gemifloxacin, moxifloxacin, nemorubicin, nalidixic acid, epirubicin, doxorubicin, daunorubicin |

TABLE 4

Day 21 prescription.

| Probe ID | Name | Fold Change D7/ Base | Fold Change D21/ Base | Fold Change D60/ Base | Fold Change D180/ Base | Gene Symbol | Drugs |
|---|---|---|---|---|---|---|---|
| Ssc.23793.1.S1_at | T-cell surface antigen CD2 | −3.27 | 79.25 | 93.34 | 5.20 | CD2 | alefacept, siplizumab |
| SscAffx.20.1.S1_at | T-cell surface glycoprotein CD3 gamma chain | −2.19 | 14.07 | 10.96 | 3.62 | CD3G | visilizumab, MT103 |
| Ssc.19532.1.S1_at | Guanylate cyclase soluble, beta-1 chain | −4.28 | 12.74 | 3.04 | 2.13 | GUCY1B3 | nitroglycerin, isosorbide-5-mononitrate, isosorbide dinitrate, nitroprusside, isosorbide dinitrate/hydralazine |
| Ssc.7176.1.A1_at | C—X—C chemokine receptor type 4 (CXC-R4) (CXCR-4) (CD184 antigen). | 3.74 | 10.91 | 8.15 | 1.68 | CXCR4 | JM 3100 |
| Ssc.2714.1.S1_a_at | Proto-oncogene tyrosine-protein kinase FYN | −4.26 | 9.56 | 12.54 | 3.93 | FYN | dasatinib |
| Ssc.15739.1.S1_at | Cytokine receptor common gamma chain (Interleukin-2 receptor gamma chain) (IL-2R gamma chain) (CD132 antigen) | −1.12 | 9.42 | 1.90 | −1.28 | IL2RG | aldesleukin, denileukin diftitox |
| Ssc.11381.1.S1_at | Interferon-alpha/beta receptor alpha chain | 10.45 | 8.08 | 2.61 | −1.30 | IFNAR1 | interferon beta-1a, interferon alfa-2b, interferon alfacon-1, PEG-interferon alfa-2a, interferon alfa-2a/ribavirin, pegintron, interferon beta-1b, IFNA2A |
| Ssc.10256.1.A1_at | cAMP-specific 3',5'-cyclic phosphodiesterase 4B | −1.89 | 6.74 | 2.20 | 2.44 | PDE4B | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.17224.1.S1_at | Toll-like receptor 8 | 1.17 | 6.49 | 3.13 | −1.52 | TLR8 | resiquimod |
| Ssc.7297.1.S1_at | Amine oxidase [flavin-containing] B (Monoamine oxidase) (MAO-B). | 1.16 | 6.42 | 7.02 | −1.13 | NAOB | safinamide, ladostigil, rasagiline, selegiline, dextroamphetamine, procainamide, tranylcypromine, phenelzine, isocarboxazid, benephetamine |
| Ssc.15801.1.A1_at | Protein kinase C, beta | 3.36 | 6.36 | 3.53 | −4.98 | PRKCB1 | enzastaurin, ruboxistaurin |
| Ssc.20818.1.S1_at | Interleukin-2 receptor beta chain (IL-2 receptor) | 1.43 | 6.35 | −1.17 | −5.23 | IL2RB | humanized MiK-Beta-1, aldesleukin, denileukin diftitox |
| Ssc.12937.1.S1_at | Presenilin 1 (PS-1) (S182 protein). | −14.09 | 6.21 | 2.48 | 3.79 | PSEN1 | (R)-flurbiprofen |
| Ssc.15932.1.S1_at | Integrin alpha-V | −6.15 | 5.79 | 2.94 | 3.14 | ITGAV | abciximab, CNTO 95, EMD121974 |
| Ssc.26328.1.S1_at | C-C chemokine receptor type 5 (CCR5) (CD195 antigen). | −2.53 | 5.61 | 3.25 | 1.29 | CCR5 | maraviroc, vicriviroc, SCH 351125 |

TABLE 4-continued

| | | Day 21 prescription. | | | | | |
|---|---|---|---|---|---|---|---|
| Probe ID | Name | Fold Change D7/ Base | Fold Change D21/ Base | Fold Change D60/ Base | Fold Change D180/ Base | Gene Symbol | Drugs |
| Ssc.12845.1.S1_at | Cell division protein kinase 6 | −6.56 | 5.40 | 4.77 | 5.13 | CDK6 | PD-0332991, flavopiridol |
| Ssc.17155.1.A1_at | heparanase; heparanase-1 | 4.81 | 5.38 | 2.98 | −1.83 | HPSE | heparanase inhibitor PI-88 |
| Ssc.13460.1.A1_at | Histone deacetylase 9 (HD9) (HD7B) (HD7) | −6.40 | 5.13 | −1.79 | 5.72 | HDAC9 | tributyrin, PXD101, pyroxamide, vorinostat, FR 901228 |
| Ssc.24528.1.S1_at | Angiotensin-converting enzyme | −1.61 | 5.01 | 2.33 | 4.76 | ACE | pentopril, perindoprilat, amlodipine/benazepril, lisinopril/hydrochlorothiazide, benazepril, enalapril, perindopril, captopril, enalapril/felodipine, hydrochlorothiazide/moexipril, benazepril/hydrochlorothiazide, hydrochlorothiazide/quinapril, fosinopril/hydrochlorothiazide, captopril/hydrochlorothiazide, enalapril/hydrochlorothiazide, ramipril, moexipril, quinapril, lisinopril, enalaprilat, trandolapril, trandolapril/verapamil, diltiazem/enalapril, fosinopril |
| Ssc.26351.1.S1_at | cAMP-specific 3',5'-cyclic phosphodiesterase 4D | 4.67 | 4.99 | 3.61 | −1.15 | PDE4D | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.15601.1.A1_s_at | Interleukin-1 beta precursor, (IL-1 beta) | 8.18 | 4.65 | −14.71 | −2.84 | IL1B | IL-1 trap |
| Ssc.3607.1.S1_at | Interferon-alpha/beta receptor beta chain | 2.28 | 4.65 | 1.11 | −1.56 | IFNAR2 | interferon beta-1a, interferon alfa-2b, interferon alfacon-1, PEG-interferon alfa-2a, interferon alfa-2a/ribavirin, pegintron, interferon beta-1b, IFNA2A |
| Ssc.20841.1.S1_at | Proto-oncogene tyrosine-protein kinase Src | −1.13 | 4.37 | −2.59 | −1.93 | SRC | dasatinib, AZM-475271 |
| Ssc.11200.1.S1_a_at | Proto-oncogene tyrosine-protein kinase ABL1 | −1.15 | 4.28 | −3.41 | −1.18 | ABL1 | imatinib, temozolomide |
| Ssc.22974.1.A1_at | Metabotropic glutamate receptor 1 | −1.05 | 4.28 | −2.05 | −5.66 | GRM1 | fasoracetam |
| Ssc.7111.1.A1_at | Ribonucleoside-diphosphate reductase M2 chain (Ribonucleotide reductase small chain) | −13.13 | 4.08 | 1.37 | 1.67 | RRM2 | gemcitabine, triapine, hydroxyurea, fludarabine phosphate |
| Ssc.9272.1.S1_at | Tumor-associated calcium signal transducer 1 (EPCAM antigen) | 1.81 | 3.94 | 176.50 | 2.07 | TACSTD1 | tucotuzumab celmoleukin |
| Ssc.16160.1.S1_at | T lymphocyte activation antigen CD86 | −1.55 | 3.88 | −1.37 | 1.18 | CD86 | abatacept |
| Ssc.14506.1.S1_at | DNA topoisomerase II, alpha isozyme | 1.01 | 3.80 | −1.18 | −14.30 | TOP2A | novobiocin, etoposide, CPI-0004Na, pixantrone, becatecarin, elsamitrucin, AQ4N, BN 80927, tafluposide, mitoxantrone, norfloxacin, dexrazoxane, tirapazamine, TAS-103, gatifloxacin, valrubicin, gemifloxacin, moxifloxacin, nemorubicin, nalidixic acid, epirubicin, doxorubicin, daunorubicin |
| Ssc.15822.1.S1_at | Coagulation factor V (Activated protein C cofactor). | 1.92 | 3.76 | 1.89 | −1.75 | F5 | drotrecogin alfa |
| Ssc.9034.1.A1_at | Proteinase activated receptor 1 precursor (PAR-1) (Thrombin receptor) | −1.29 | 3.75 | −1.40 | 1.37 | F2R | chrysalin, argatroban, bivalirudin |
| Ssc.15886.1.S1_at | Apopain precursor (Caspase-3) (CASP-3) | −3.02 | 3.64 | 2.31 | 2.29 | CASP3 | IDN-6556 |

TABLE 4-continued

Day 21 prescription.

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.17518.1.S1_at | Adenosine A1 receptor | −3.16 | 3.44 | −1.56 | 1.58 | ADORA1 | adenosine, dyphylline, aminophylline, clofarabine, theophylline, caffeine, tecadenoson |
| Ssc.14258.1.S1_at | Amyloid beta A4 protein precursor (APP) (ABPP) | 1.87 | 3.33 | 1.34 | −1.02 | APP | AAB-001 |
| Ssc.14471.1.S1_at | B-lymphocyte antigen CD19 precursor (Differentiation antigen CD19 | 9.54 | 3.30 | −10.32 | 3.04 | CD19 | combotox, HD37-dgRTA, MT103 |
| Ssc.15878.1.S1_at | Serine/threonine protein phosphatase 2B catalytic subunit, alpha | 1.85 | 3.22 | 3.62 | −1.49 | PPP3CA | ISAtx-247, tacrolimus, pimecrolimus, cyclosporin A |
| Ssc.21108.1.S1_at | Complement C5 | −17.35 | 3.21 | 618.80 | 9.28 | C5 | eculizumab |
| Ssc.16186.1.S1_at | T-cell surface glycoprotein CD3 epsilon chain (T-cell surface antigen T3/Leu-4 epsilon chain) | 9.00 | 3.12 | 2.12 | −5.66 | CD3E | visilizumab, MT103, muromonab-CD3 |
| Ssc.24966.1.S1_at | Purine nucleoside phosphorylase (Inosine phosphorylase) (PNP). | −3.34 | 3.12 | 3.46 | −1.14 | NP | forodesine, 9-deaza-9-(3-thienylmethyl)guanine |
| Ssc.19873.1.S1_at | Collagen alpha 1(XVII) chain (Bullous pemphigoid antigen 2) | −2.37 | 3.02 | −1.55 | 2.18 | COL17A1 | collagenase |
| Ssc.20904.1.A1_at | RAC-gamma serine/threonine-protein kinase (RAC-PK-gamma) (Protein kinase Akt-3) (Protein kinase B, gamma) (PKB gamma) (STK-2) | −1.34 | 3.01 | −2.18 | 1.23 | AKT3 | enzastaurin |
| Ssc.26646.1.S1_at | Glutamate receptor 1 | −1.10 | 2.91 | −5.42 | −3.43 | GRIA1 | talampanel, Org 24448, LY451395, tezampanel |
| Ssc.15312.1.S1_at | Histone deacetylase 4 (HD4) | −1.93 | 2.85 | −2.41 | 1.20 | HDAC4 | tributyrin, PXD101, pyroxamide, vorinostat, FR 901228 |
| Ssc.24889.1.S1_at | Arachidonate 12-lipoxygenase, 12S-type | 1.97 | 2.83 | −1.18 | −2.78 | ALOX12 | sulfasalazine, balsalazide, 5-aminosalicylic acid, masoprocol, verteportin |
| Ssc.12630.1.A1_at | Sodium/potassium-transporting ATPase alpha-1 chain | 2.97 | 2.81 | −7.30 | −2.03 | ATP1A1 | digoxin, omeprazole, ethacrynic acid, perphenazine |
| Ssc.3040.1.S1_at | Histone deacetylase 2 (HD2) | −3.24 | 2.79 | 4.94 | 4.72 | HDAC2 | tributyrin, PXD101, pyroxamide, vorinostat, FR901228 |
| Ssc.12791.1.A1_at | 3-hydroxy-3-methylglutaryl-coenzyme A reductase (HMG-CoA reductase) | 3.27 | 2.77 | 1.77 | −2.56 | HMGCR | aspirin/pravastatin, lovastatin/niacin, ezetimibe/simvastatin, amlodipine/atorvastatin, fluvastatin, cerivastatin, atorvastatin, pravastatin, simvastatin, lovastatin, rosuvastatin |
| Ssc.20685.1.S1_at | Apoptosis regulator Bcl-2 | −2.22 | 2.77 | 2.58 | 3.25 | BCL2 | oblimersen, (−)-gossypol |
| Ssc.15965.1.S1_at | Inward rectifier potassium channel 2 (Potassium channel, inwardly rectifying, subfamily J, member 2) (Inward rectifier K+ channel Kir2.1) (Cardiac inward rectifier potassium channel) (IRK1). | 4.68 | 2.72 | −1.84 | −4.62 | KCNJ2 | nicorandil, amiodarone |
| Ssc.19673.1.S1_at | T-cell surface glycoprotein CD3 delta chain precursor (T-cell receptor T3 delta chain) | 6.40 | 2.70 | 2.03 | −11.77 | CD3D | visilizumab, MT103 |
| Ssc.16127.1.S1_at | Adrenocorticotropic hormone receptor (ACTH receptor) (ACTH-R) | −1.67 | 2.70 | −2.51 | −1.10 | MC2R | cosyntropin, ACTH |
| Ssc.11406.1.A1_a_at | Interleukin-1 receptor, type I precursor (IL-1R-1) (IL-1R-alpha) (P80) (Antigen CD121a) | 1.03 | 2.70 | −2.44 | 1.42 | IL1R1 | anakinra |
| Ssc.19937.1.S1_at | Inosine-5′-monophosphate dehydrogenase 2 (IMP dehydrogenase 2) | 1.00 | 2.69 | −1.47 | 3.65 | IMPDH2 | thioguanine, VX-944, interferon alfa-2a/ribavirin, mycophenolic acid, ribavirin |
| Ssc.818.1.S1_at | RAF proto-oncogene serine/threonine-protein kinase | −1.40 | 2.56 | 1.58 | 1.98 | RAF1 | sorafenib |

TABLE 4-continued

Day 21 prescription.

| Probe ID | Name | Fold Change D7/ Base | Fold Change D21/ Base | Fold Change D60/ Base | Fold Change D180/ Base | Gene Symbol | Drugs |
|---|---|---|---|---|---|---|---|
| Ssc.14129.1.A1_at | 4-aminobutyrate aminotransferase, mitochondrial precursor (Gamma-amino-N-butyrate transaminase) (GABA transaminase) | 6.91 | 2.56 | −21.17 | −3.35 | ABAT | valproic acid |
| Ssc.13186.1.S1_at | Cell division protein kinase 7 | −1.08 | 2.38 | 4.34 | 1.24 | CDK7 | BMS-387032, flavopiridol |
| Ssc.16167.1.S1_at | Rho-associated protein kinase 1 | 2.40 | 2.32 | 2.83 | 3.00 | ROCK1 | fasudil, Y-27632 |
| Ssc.6418.1.S1_at | Farnesyl-diphosphate farnesyltransferase | −1.25 | 2.31 | 1.33 | 1.08 | FDFT1 | TAK-475, zoledronic acid |
| Ssc.15829.1.S1_at | Retinoic acid receptor alpha | −1.73 | 2.23 | −1.33 | −1.16 | RARA | etretinate, adapalene, arsenic trioxide, 13-cis-retinoic acid, tazarotene, acitretin, retinoic acid, 9-cis-retinoic acid |
| Ssc.10142.1.A1_at | Dihydropyrimidine dehydrogenase [NADP+] (DPD) (DHPDHase) (Dihydrouracil dehydrogenase) (Dihydrothymine dehydrogenase). | 2.06 | 2.17 | 1.13 | −2.68 | DPYD | eniluracil |
| Ssc.23505.1.S1_at | Amine oxidase [flavin-containing] A (Monoamine oxidase) (MAO-A) | −1.86 | 2.17 | 1.08 | 1.20 | MAOA | ladostigil, 1-ethylphenoxathiin 10,10-dioxide, dextroamphetamine, procainamide, tranylcypromine, phenelzine, isocarboxazid, benzphetamine, N-(2-indanyl)glycinamide |
| Ssc.20438.1.S1_at | Prostaglandin F2-alpha receptor (Prostanoid FP receptor) (PGF receptor) (PGF2 alpha receptor). | −3.20 | 2.13 | 5.28 | −38.97 | PTGFR | tafluprost, travoprost, isopropyl unoprostone, bimatoprost, latanoprost |
| Ssc.4756.1.A1_at | Adenosine A3 receptor | 2.15 | 2.10 | 1.88 | −1.81 | ADORA3 | adenosine, dyphylline, aminophylline, clofarabine, theophylline, caffeine |
| Ssc.11302.1.S1_at | Collagen alpha 1(III) chain | −1.80 | 2.02 | 2.06 | 1.26 | COL3A1 | collagenase |
| Ssc.19400.2.A1_at | Presenilin 2 (PS-2) (STM-2) (E5-1) (AD3LP) (AD5) | −2.32 | 1.99 | −5.30 | −3.44 | PSEN2 | (R)-flurbiprofen |
| Ssc.3059.1.S1_at | Aldose reductase (AR) (Aldehyde reductase). | −1.74 | 1.98 | −1.66 | 2.49 | AKR1B1 | sorbinil, Zopolrestat (Alond, Pfizer), zenarestat (Fujisawa, Parke-Davis) |
| Ssc.18051.1.S1_at | cGMP-inhibited 3',5'-cyclic phosphodiesterase B (Cyclic GMP inhibited phosphodiesterase B) (CGI-PDE B) (CGIPDE1) (CGIP1) | −3.16 | 1.96 | 3.41 | 2.32 | PDE3B | dyphylline, nitroglycerin, medorinone, aminophylline, cilostazol, dipyridamole, amrinone, tolbutamide, theophylline, pentoxifylline |
| Ssc.2548.1.S1_at | DNA polymerase epsilon p17 subunit (DNA polymerase epsilon subunit 3) (Chromatin accessibility complex 17) (HuCHRAC17) (CHRAC-17). | 2.27 | 1.93 | −1.67 | −1.21 | POLE3 | gemcitabine |
| Ssc.11383.1.A1_at | Glutamate receptor 3 precursor (GluR-3) (GluR-C) (GluR-K3) (Glutamate receptor ionotropic, AMPA 3) | 2.61 | 1.85 | −1.87 | −2.43 | GRIA3 | talampanel, Org 24448, LY451395, tezampanel |
| Ssc.8549.1.A1_at | Guanylate cyclase soluble, alpha-3 chain (GCS-alpha-3) (Soluble guanylate cyclase large subunit) (GCS-alpha-1). | 1.11 | 1.84 | −2.00 | −2.59 | GUCY1A3 | nitroglycerin, isosorbide-5-mononitrate, isosorbide dinitrate, nitroprusside, isosorbide dinitrate/hydralazine |
| Ssc.12781.1.A1_at | Toll-like receptor 4 | 2.39 | 1.83 | −1.52 | −6.10 | TLR4 | TAK-242 |
| Ssc.6301.1.S1_at | Aromatic-L-amino-acid decarboxylase (AADC) (DOPA decarboxylase) | 1.76 | 1.80 | −4.91 | −1.88 | DDC | carbidopa/entacapone/levodopa, carbidopa/levodopa, S(−)-carbidopa, L-dopa |
| Ssc.6801.1.S1_at | Proto-oncogene tyrosine-protein kinase YES | −1.06 | 1.69 | 2.36 | −1.82 | YES1 | dasatinib |
| Ssc.5371.1.S1_a_at | DNA polymerase epsilon subunit B (DNA polymerase II subunit B). | 10.16 | 1.68 | −1.37 | −3.14 | POLE2 | gemcitabine |
| Ssc.11572.1.A1_at | Histone deacetylase 3 (HD3) (RPD3-2) (SMAP45) | −1.65 | 1.67 | −1.55 | 2.36 | HDAC3 | tributyrin, PXD101, pyroxamide, MGCD0103, vorinostat, FR 901228 |
| Ssc.23234.1.S1_at | collagen, type XXIV, alpha 1 | −1.43 | 1.66 | 1.16 | 1.76 | COL24A1 | collagenase |

TABLE 4-continued

Day 21 prescription.

| Probe ID | Name | Fold Change D7/ Base | Fold Change D21/ Base | Fold Change D60/ Base | Fold Change D180/ Base | Gene Symbol | Drugs |
|---|---|---|---|---|---|---|---|
| Ssc.9565.1.S1_at | Interferon-gamma receptor alpha chain precursor (IFN-gamma-R1) (CD119 antigen) | 2.92 | 1.63 | 1.41 | −1.23 | IFNGR1 | interferon gamma-1b |
| Ssc.5021.1.S1_at | Glutamate decarboxylase, 65 kDa isoform (GAD-65) (65 kDa glutamic acid decarboxylase) | −29.44 | 1.62 | −10.79 | −5.61 | GAD2 | valproic acid |
| Ssc.14326.1.A1_at | Mitogen-activated protein kinase 13 (Stress-activated protein kinase-4) (Mitogen-activated protein kinase p38 delta) (MAP kinase p38 delta) | 12.63 | 1.56 | −1.80 | −7.24 | MAPK13 | SCIO-469 |
| Ssc.10591.1.A1_at | Metabotropic glutamate receptor 5 precursor (mGluR5) | −7.83 | 1.54 | −1.31 | 1.40 | GRM5 | fasoracetam |
| Ssc.30373.1.A1_at | cGMP-specific 3',5'-cyclic phosphodiesterase | 4.27 | 1.52 | 2.34 | 4.09 | PDE5A | dyphylline, nitroglycerin, DA-8159, aminophylline, sildenafil, dipyridamole, aspirin/dipyridamole, vardenafil, tolbutamide, tadalafil, theophylline, pentoxifylline |
| Ssc.6710.1.A1_at | Ribonucleoside-diphosphate reductase M1 chain (Ribonucleotide reductase large chain) | −1.90 | 1.44 | 2.01 | −1.01 | RRM1 | gemcitabine, clofarabine, fludarabine phosphate |
| Ssc.7139.1.S1_at | Dihydrofolate reductase | −1.13 | 1.41 | −1.12 | 2.06 | DHFR | pyrimethamine, trimethoprim, iclaprim, methotrexate, sulfisoxazole, triamterene, folic acid, trimetrexate, LY231514, PT 523 |
| Ssc.5538.1.S1_at | Carbonic anhydrase II (Carbonate dehydratase II) (CA-II) (Carbonic anhydrase C) | 8.09 | 1.39 | −2.25 | −1.35 | CA2 | methazolamide, hydrochlorothiazide, acetazolamide, trichloromethiazide, dorzolamide, chlorothiazide, dorzolamide/timolol, brinzolamide, chlorthalidone, benzthiazide, sulfacetamide, topiramate |
| Ssc.5569.1.S1_at | Thyroid hormone receptor alpha (C-erbA-alpha) (c-erbA-1) (EAR-7) (EAR7) | −10.22 | 1.26 | 1.26 | 6.49 | THRA | 3,5-diiodothyropropionic acid, amiodarone, thyroxine, L-triiodothyronine |
| Ssc.10360.1.S1_at | B-Raf proto-oncogene serine/threonine-protein kinase | −2.15 | 1.26 | 3.09 | 1.36 | BRAF | sorafenib |
| Ssc.19672.1.S1_at | RAC-alpha serine/threonine-protein kinase (RAC-PK-alpha) (Protein kinase B) (PKB) (C-AKT) | 17.77 | 1.25 | −19.82 | −2.11 | AKT1 | enzastaurin |
| Ssc.21011.1.S1_at | Collagen alpha 2(I) chain | −2.70 | 1.24 | 3.12 | −1.01 | COL1A2 | collagenase |
| Ssc.5045.1.S1_at | 3-beta-hydroxysteroid-delta(8),delta(7)-isomerase (Cholestenol delta-isomerase) (Delta8-delta7 sterol isomerase) (D8-D7 sterol isomerase) (Emopamil-binding protein) | −1.55 | 1.24 | 2.19 | 2.08 | EBP | SR 31747 |
| Ssc.8726.1.A1_at | Amidophosphoribosyltransferase precursor (Glutamine phosphoribosylpyrophosphate amidotransferase) (ATASE) (GPAT) | 1.03 | 1.24 | 4.16 | −1.11 | PPAT | 6-mercaptopurine, thioguanine, azathioprine |
| Ssc.10219.1.A1_at | Excitatory amino acid transporter 4 (Sodium-dependent glutamate/aspartate transporter) | 1.36 | 1.24 | −3.38 | −1.03 | SLC1A6 | riluzole |
| Ssc.15999.1.A1_at | Vascular endothelial growth factor receptor 2 precursor (VEGFR-2) (Kinase insert domain receptor) (Protein-tyrosine kinase receptor Flk-1) | 1.24 | 1.24 | 18.52 | −11.02 | KDR | AEE 788, sunitinib, AZD 2171, pazopanib, XL647, CEP 7055, BMS-582664, KRN-951, vatalanib, sorafenib, vandetanib, pegaptanib |

TABLE 4-continued

Day 21 prescription.

| Probe ID | Name | Fold Change D7/ Base | Fold Change D21/ Base | Fold Change D60/ Base | Fold Change D180/ Base | Gene Symbol | Drugs |
|---|---|---|---|---|---|---|---|
| Ssc.9348.1.S1_at | Peroxisome proliferator activated receptor alpha (PPAR-alpha) | −1.05 | 1.22 | −3.05 | −1.52 | PPARA | NS-220, tesaglitazar, clofibrate, fenofibrate, docosahexaenoic acid, gemfibrozil |
| Ssc.1498.1.S1_at | Proteasome subunit beta type 5 precursor (Proteasome epsilon chain) (Macropain epsilon chain) (Multicatalytic endopeptidase complex epsilon chain) (Proteasome subunit X) (Proteasome chain 6) (Proteasome subunit MB1) | −1.81 | 1.19 | 1.38 | 5.94 | PSMB5 | bortezomib |
| Ssc.6934.1.A1_at | Thymidylate synthase (EC 2.1.1.45) (TS) (TSase) (OK/SW-cl.29) | −1.13 | 1.19 | −1.11 | −2.81 | TYMS | flucytosine, 5-fluorouracil, plevitrexed, nolatrexed, capecitabine, trifluridine, floxuridine, LY231514 |
| Ssc.28329.1.S1_at | DNA polymerase beta | 1.14 | 1.19 | 1.07 | 5.25 | PCLB | nelarabine, clofarabine, stavudine, trifluridine, vidarabine, zalcitabine, entecavir |
| Ssc.16823.1.S1_at | P2Y purinoceptor 12 (P2Y12) (P2Y12 platelet ADP receptor) (P2Y(ADP)) (ADP-glucose receptor) (ADPG-R) (P2Y(AC)) (P2Y(cyc)) (P2T(AC)) (SP1999 | 1.38 | 1.19 | 1.41 | 1.11 | P2RY12 | prasugrel, AZD 6140 (Ticagrelor), clopidogrel |
| Ssc.19691.1.S1_at | Platelet-activating factor acetylhydrolase precursor (EC 3.1.1.47) (PAF acetylhydrolase) (PAF 2-acylhydrolase) (LDL-associated phospholipase A2) (LDL-PLA(2)) (2-acetyl-1-alkylglycerophosphocholine esterase) (1-alkyl-2-acetylglycerophosphocholine esterase) | 1.59 | 1.16 | 3.01 | 1.47 | PLA2G7 | darapladib |
| Ssc.15880.1.S1_at | Cysteinyl leukotriene receptor 2 (CysLTR2) (PSEC0146) (HG57) (HPN321) (hGPCR21) | 2.86 | 1.14 | −2.12 | −3.42 | CYSLTR2 | montelukast, zafirlukast |
| Ssc.11147.1.S1_at | Aldehyde dehydrogenase, mitochondrial precursor (EC 1.2.1.3) (ALDH class 2) (ALDHI) (ALDH-E2) | 3.18 | 1.13 | 2.00 | −1.68 | ALDH2 | disulfiram, chlorpropamide |
| Ssc.1908.1.S1_at | FKBP-rapamycin associated protein (FRAP) (Rapamycin target protein) | 1.99 | 1.13 | −1.88 | −1.46 | FRAP1 | AP23573, temsirolimus, tacrolimus, everolimus |
| Ssc.19700.1.S1_at | Serine/threonine protein phosphatase 2B catalytic subunit, beta | 1.11 | 1.13 | 1.34 | 1.09 | PPP3CB | ISAtx-247, tacrolimus, pimecrolimus, cyclosporin A |
| Ssc.30147.1.A1_at | Fibroblast growth factor receptor 2 precursor (FGFR-2) (Keratinocyte growth factor receptor 2) | 1.56 | 1.13 | −1.05 | −1.18 | FGFR2 | palifermin |
| Ssc.27232.1.S1_at | Succinate semialdehyde dehydrogenase, mitochondrial precursor (NAD(+)-dependent succinic semialdehyde dehydrogenase) | 2.06 | 1.12 | −2.84 | −5.73 | ALDH5A1 | valproic acid |
| Ssc.10215.1.A1_at | High-affinity cAMP-specific and IBMX-insensitive 3',5'-cyclic phosphodiesterase 8A | 1.83 | 1.12 | −8.48 | −15.51 | PDE8A | dyphylline, nitroglycerin, aminophylline, anagrelide, milrinone, dipyridamole, tolbutamide, theophylline, pentoxifylline |
| Ssc.2767.2.S1_a_at | Prostaglandin E2 receptor, EP3 subtype (Prostanoid EP3 receptor) (PGE receptor, EP3 subtype) | 2.30 | 1.12 | −1.59 | −6.78 | PTGER3 | prostaglandin E1 |
| Ssc.15955.1.S1_at | Antithrombin-III precursor (ATIII) (PRO0309) | −1.89 | 1.12 | −2.06 | −2.42 | SERPINC1 | enoxaparin, SR-123781A, fondaparinux |
| Ssc.25040.1.S1_at | Serine/threonine-protein kinase Chk1 | −3.75 | 1.11 | 1.06 | −2.45 | CHEK1 | UCN-01 (7-hydroxystaurosporine) |

TABLE 4-continued

Day 21 prescription.

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.14488.1.S1_at | Glutamate carboxypeptidase II (Membrane glutamate carboxypeptidase) | −1.04 | 1.10 | 1.02 | 1.69 | FOLH1 | capromab pendetide |
| Ssc.1.1.S1_at | 3-oxo-5-alpha-steroid 4-dehydrogenase 2 (Steroid 5-alpha-reductase 2) (SR type 2) (5 alpha-SR2) | −1.77 | 1.05 | −4.11 | −1.09 | SRD5A2 | finasteride, dutasteride |
| Ssc.7581.1.A1_at | FL cytokine receptor precursor (Tyrosine-protein kinase receptor FLT3) (Stem cell tyrosine kinase 1) (STK-1) (CD135 antigen) | 1.69 | 1.04 | −1.81 | 1.01 | FLT3 | CHIR-258, sorafenib, lestaurtinib, CGP 41251 |

TABLE 5

Day 60 prescription.

| Probe ID | Name | Fold Change D7/Base | Fold Change D21/Base | Fold Change D60/Base | Fold Change D180/Base | Gene Symbol | DRUGS |
|---|---|---|---|---|---|---|---|
| Ssc.21108.1.S1_at | Complement C5 | −17.35 | 3.21 | 618.80 | 9.28 | C5 | eculizumab |
| Ssc.9272.1.S1_at | Tumor-associated calcium signal transducer 1 (EPCAM antigen) | 1.81 | 3.94 | 176.50 | 2.07 | TACSTD1 | tucotuzumab celmoleukin |
| Ssc.23793.1.S1_at | T-cell surface antigen CD2 | −3.27 | 79.25 | 93.34 | 5.20 | CD2 | alefacept, siplizumab |
| Ssc.17245.1.S1_at | Interleukin-13 receptor alpha-1 chain | −1.99 | 23.04 | 21.92 | 7.16 | IL13RA1 | cintredekin besudotox |
| Ssc.15999.1.A1_at | Vascular endothelial growth factor receptor 2 | 1.24 | 1.24 | 18.52 | −11.02 | KDR | AEE 788, sunitinib, AZD 2171, pazopanib, XL647, CEP 7055, BMS-582664, KRN-951, vatalanib, sorafenib, vandetanib, pegaptanib |
| Ssc.27603.1.S1_at | Endothelin B receptor precursor (ET-B) (Endothelin receptor Non-selective type) | 5.30 | −3.27 | 15.99 | 1.23 | EDNRB | bosentan, sitaxsentan, atrasentan |
| Ssc.2714.1.S1_a_at | Proto-oncogene tyrosine-protein kinase FYN | −4.26 | 9.56 | 12.54 | 3.93 | FYN | dasatinib |
| SscAffx.20.1.S1_at | T-cell surface glycoprotein CD3 gamma chain | −2.19 | 14.07 | 10.96 | 3.62 | CD3G | visilizumab, MT103 |
| Ssc.7176.1.A1_at | C—X—C chemokine receptor type 4 (CXC-R4) (CXCR-4) | 3.74 | 10.91 | 8.15 | 1.68 | CXCR4 | JM 3100 |
| Ssc.26200.1.S1_at | Thyroid hormone receptor beta-1 | 3.49 | −1.56 | 7.96 | 2.52 | THRB | 3,5-diiodothyropropionic acid, amiodarone, thyroxine, L-triiodothyronine |
| Ssc.7297.1.S1_at | Amine oxidase [flavin-containing] B(Monoamine oxidase) (MAO-B). | 1.16 | 6.42 | 7.02 | −1.13 | MAOB | safinamide, ladostigil, rasagiline, selegiline, dextroamphetamine, procainamide, tranylcypromine, phenelzine, isocarboxazid, benzphetamine |
| Ssc.9019.1.A1_at | Atrial natriuretic peptide clearance receptor precursor (ANP-C) (ANPRC) | −1.09 | −1.69 | 5.31 | 1.18 | NPR3 | nesiritide |
| Ssc.20438.1.S1_at | Prostaglandin F2-alpha receptor | −3.20 | 2.13 | 5.28 | −38.97 | PTGFR | tafluprost, travoprost, isopropyl unoprostone, bimatoprost, latanoprost |
| Ssc.3040.1.S1_at | Histone deacetylase 2 (HD2) | −3.24 | 2.79 | 4.94 | 4.72 | HDAC2 | tributyrin, PXD101, pyroxamide, vorinostat, FR 901228 |
| Ssc.26325.1.S1_at | Cystic fibrosis transmembrane conductance regulator (CFTR) | 1.60 | −5.71 | 4.77 | −8.99 | CFTR | SP 303 |
| Ssc.12845.1.S1_at | Cell division protein kinase 6 | −6.56 | 5.40 | 4.77 | 5.13 | CDK6 | PD-0332991, flavopiridol |
| Ssc.13186.1.S1_at | Cell division protein kinase 7 | −1.08 | 2.38 | 4.34 | 1.24 | CDK7 | BMS-387032, flavopiridol |
| Ssc.8726.1.A1_at | Amidophosphoribosyltransferase | 1.03 | 1.24 | 4.16 | −1.11 | PPAT | 6-mercaptopurine, thioguanine, azathioprine |
| Ssc.15374.1.S1_at | COL14A1 protein | 1.10 | −17.71 | 3.79 | 2.24 | COL14A1 | collagenase |
| Ssc.1147.1.A1_at | Lipoprotein lipase | 4.05 | −5.49 | 3.78 | −8.08 | LPL | nicotinic acid, lovastatin/niacin |
| Ssc.15878.1.S1_at | Serine/threonine protein phosphatase 2B catalytic subunit, alpha | 1.85 | 3.22 | 3.62 | −1.49 | PPP3CA | ISAtx-247, tacrolimus, pimecrolimus, cyclosporin A |

TABLE 5-continued

Day 60 prescription.

| Probe ID | Name | Fold Change D7/ Base | Fold Change D21/ Base | Fold Change D60/ Base | Fold Change D180/ Base | Gene Symbol | DRUGS |
|---|---|---|---|---|---|---|---|
| Ssc.26351.1.S1_at | cAMP-specific 3',5'-cyclic phosphodiesterase 4D | 4.67 | 4.99 | 3.61 | −1.15 | PDE4D | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.15801.1.A1_at | Protein kinase C, beta | 3.36 | 6.36 | 3.53 | −4.98 | PRKCB1 | enzastaurin, ruboxistaurin |
| Ssc.10055.1.A1_at | Alpha platelet-derived growth factor receptor | −2.14 | −1.46 | 3.52 | −1.14 | PDGFRA | sunitinib, axitinib, imatinib, becaplermin |
| Ssc.24966.1.S1_at | Purine nucleoside phosphorylase | −3.34 | 3.12 | 3.46 | −1.14 | NP | forodesine, 9-deaza-9-(3-thienylmethyl)guanine |
| Ssc.18051.1.S1_at | cGMP-inhibited 3',5'-cyclic phosphodiesterase B | −3.16 | 1.96 | 3.41 | 2.32 | PDE3B | dyphylline, nitroglycerin, medorinone, aminophylline, cilostazol, dipyridamole, amrinone, tolbutamide, theophylline, pentoxifylline |
| Ssc.9523.1.A1_at | Methylated-DNA--protein-cysteine methyltransferase | 1.55 | −1.17 | 3.35 | 1.47 | MGMT | O6-benzylguanine |
| Ssc.16000.1.A1_at | Vascular endothelial growth factor receptor 1 | 1.08 | −3.40 | 3.34 | 1.72 | FLT1 | sunitinib, axitinib, CEP 7055 |
| Ssc.26328.1.S1_at | C-C chemokine receptor type 5 (CCR5) (CD195 antigen). | −2.53 | 5.61 | 3.25 | 1.29 | CCR5 | maraviroc, vicriviroc, SCH 351125 |
| Ssc.17224.1.S1_at | Toll-like receptor 8 | 1.17 | 6.49 | 3.13 | −1.52 | TLR8 | resiquimod |
| Ssc.21011.1.S1_at | Collagen alpha 2(I) chain | −2.70 | 1.24 | 3.12 | −1.01 | COL1A2 | collagenase |
| Ssc.10360.1.A1_at | B-Raf proto-oncogene serine/threonine-protein kinase | −2.15 | 1.26 | 3.09 | 1.36 | BRAF | sorafenib |
| Ssc.19532.1.S1_at | Guanylate cyclase soluble, beta-1 chain | −4.28 | 12.74 | 3.04 | 2.13 | GUCY1B3 | nitroglycerin, isosorbide-5-mononitrate, isosorbide dinitrate, nitroprusside, isosorbide dinitrate/hydralazine |
| Ssc.19691.1.S1_at | Platelet-activating factor acetylhydrolase precursor | 1.59 | 1.16 | 3.01 | 1.47 | PLA2G7 | darapladib |
| Ssc.17155.1.A1_at | heparanase; heparanase-1 | 4.81 | 5.38 | 2.98 | −1.83 | HPSE | heparanase inhibitor PI-88 |
| Ssc.15932.1.S1_at | Integrin alpha-V precursor | −6.15 | 5.79 | 2.94 | 3.14 | ITGAV | abciximab, CNTO 95, EMD121974 |
| Ssc.16167.1.S1_at | Rho-associated protein kinase 1 | 2.40 | 2.32 | 2.83 | 3.00 | ROCK1 | fasudil, Y-27632 |
| Ssc.62.2.S1_a_at | Interleukin-6 (IL-6) | 1.89 | −6.32 | 2.77 | −1.04 | IL6 | tocilizumab |
| Ssc.11246.1.A1_at | Protein kinase C, alpha | −5.96 | −4.78 | 2.68 | 2.46 | PRKCA | L-threo-safingol |
| Ssc.11381.1.S1_at | Interferon-alpha/beta receptor alpha | 10.45 | 8.08 | 2.61 | −1.30 | IFNAR1 | interferon beta-1a, interferon alfa-2b, interferon alfacon-1, PEG-interferon alfa-2a, interferon alfa-2a/ribavirin, pegintron, interferon beta-1b, IFNA2A |
| Ssc.20685.1.S1_at | Apoptosis regulator Bcl-2 | −2.22 | 2.77 | 2.58 | 3.25 | BCL2 | oblimersen, (—)-gossypol |
| Ssc.12937.1.S1_at | Presenilin 1 (PS-1) (S182 protein) | −14.09 | 6.21 | 2.48 | 3.79 | PSEN1 | (R)-flurbiprofen |
| Ssc.8500.1.A1_at | Glutamate receptor 4 precursor (GluR-4) (GluR4) (GluR-D) (Glutamate receptor ionotropic, AMPA 4) | −1.04 | −1.13 | 2.39 | −7.80 | GRIA4 | talampanel, Org 24448, LY451395, tezampanel |
| Ssc.6801.1.S1_at | Proto-oncogene tyrosine-protein kinase YES | −1.06 | 1.69 | 2.36 | −1.82 | YES1 | dasatinib |
| Ssc.30373.1.A1_at | cGMP-specific 3',5'-cyclic phosphodiesterase | 4.27 | 1.52 | 2.34 | 4.09 | PDE5A | dyphylline, nitroglycerin, DA-8159, aminophylline, sildenafil, dipyridamole, aspirin/dipyridamole, vardenafil, tolbutamide, tadalafil, theophylline, pentoxifylline |
| Ssc.15886.1.S1_at | Apopain precursor (Caspase-3) (CASP-3) | −3.02 | 3.64 | 2.31 | 2.29 | CASP3 | IDN-6556 |
| Ssc.16114.1.S1_at | Dihydropyridine-sensitive L-type, calcium channel alpha-2/delta subunits | −1.96 | −4.18 | 2.24 | 3.65 | CACNA2D1 | bepridil, amlodipine, pregabalin |
| Ssc.10256.1.A1_at | cAMP-specific 3',5'-cyclic phosphodiesterase 4B (EC 3.1.4.17) (DPDE4) (PDE32) | −1.89 | 6.74 | 2.20 | 2.44 | PDE4B | dyphylline, nitroglycerin, arofylline, tetomilast, L 869298, aminophylline, anagrelide, cilomilast, milrinone, rolipram, |

TABLE 5-continued

| | | Day 60 prescription. | | | | | |
|---|---|---|---|---|---|---|---|
| Probe ID | Name | Fold Change D7/ Base | Fold Change D21/ Base | Fold Change D60/ Base | Fold Change D180/ Base | Gene Symbol | DRUGS |
| Ssc.5045.1.S1_at | 3-beta-hydroxysteroid-delta(8), delta(7)-isomerase (Emopamil-binding protein) | −1.55 | 1.24 | 2.19 | 2.08 | EBP | dipyridamole, L-826,141, roflumilast, tolbutamide, theophylline, pentoxifylline, caffeine SR 31747 |
| Ssc.204.1.S1_at | Cytochrome P450 3A4 | 1.97 | −3.35 | 2.16 | −1.42 | CYP3A4 | ketoconazole |
| Ssc.16186.1.S1_at | T-cell surface glycoprotein CD3 epsilon chain | 9.00 | 3.12 | 2.12 | −5.66 | CD3E | visilizumab, MT103, muromonab-CD3 |
| Ssc.1091.1.S1_at | Collagen alpha 1(I) chain | −3.27 | −17.59 | 2.07 | 1.03 | COL1A1 | collagenase |
| Ssc.11302.1.S1_at | Collagen alpha 1(III) chain | −1.80 | 2.02 | 2.06 | 1.26 | COL3A1 | collagenase |
| Ssc.19673.1.S1_at | T-cell surface glycoprotein CD3 delta chain | 6.40 | 2.70 | 2.03 | −11.77 | CD3D | visilizumab, MT103 |
| Ssc.6710.1.A1_at | Ribonucleoside-diphosphate reductase M1 chain (Ribonucleotide reductase large chain) | −1.90 | 1.44 | 2.01 | −1.01 | RRM1 | gemcitabine, clofarabine, fludarabine phosphate |
| Ssc.11147.1.S1_at | Aldehyde dehydrogenase, mitochondrial precursor ((ALDHI) | 3.18 | 1.13 | 2.00 | −1.68 | ALDH2 | disulfiram, chlorpropamide |
| Ssc.1520.1.A1_at | Proto-oncogene tyrosine-protein kinase receptor ret | −1.05 | −1.88 | 2.00 | 2.39 | RET | sunitinib |
| Ssc.30888.1.S1_at | Voltage-dependent L-type calcium channel alpha-1D subunit | 2.92 | −2.72 | 1.90 | −7.82 | CACNA1D | MEM-1003, mibefradil, bepridil, nisoldipine, isradipine, nicardipine |
| Ssc.15739.1.S1_at | Cytokine receptor common gamma chain (IL-2R gamma chain) CD132 antigen) | −1.12 | 9.42 | 1.90 | −1.28 | IL2RG | aldesleukin, denileukin diftitox |
| Ssc.15822.1.S1_at | Coagulation factor V (Activated protein C cofactor) | 1.92 | 3.76 | 1.89 | −1.75 | F5 | drotrecogin alfa |
| Ssc.4756.1.A1_at | Adenosine A3 receptor. | 2.15 | 2.10 | 1.88 | −1.81 | ADORA3 | adenosine, dyphylline, aminophylline, clofarabine, theophylline, caffeine |
| Ssc.12791.1.A1_at | 3-hydroxy-3-methylglutaryl-coenzyme A reductase (HMG-CoA reductase) | 3.27 | 2.77 | 1.77 | −2.56 | HMGCR | aspirin/pravastatin, lovastatin/niacin, ezetimibe/simvastatin, amlodipine/atorvastatin, fluvastatin, cerivastatin, atorvastatin, pravastatin, simvastatin, lovastatin, rosuvastatin |
| Ssc.27293.1.A1_at | Hypoxanthine-guanine phosphoribosyltransferase (HGPRT) | 2.15 | −1.16 | 1.63 | −7.14 | HPRT1 | 6-mercaptopurine, thioguanine, azathioprine |
| Ssc.16189.1.S1_at | Endothelin-1 receptor (Endothelin A receptor) (ET-A) | −1.11 | −2.54 | 1.58 | −2.91 | EDNRA | bosentan, avosentan, clazosentan, ambrisentan, sitaxsentan, ZD4054, SB 234551, TBC 3214, BSF 302146, PD 180988, atrasentan |
| Ssc.818.1.S1_at | RAF proto-oncogene serine/threonine-protein kinase | −1.40 | 2.56 | 1.58 | 1.98 | RAF1 | sorafenib |
| Ssc.15748.2.S2_at | T lymphocyte activation antigen CD80 | 1.95 | −1.24 | 1.54 | −3.12 | CD80 | abatacept |
| Ssc.19059.1.A1_at | Type-1 angiotensin II receptor (AT1) (AT1AR) | 5.57 | −2.57 | 1.50 | −11.08 | AGTR1 | amlodipine/olmesartan medoxomil, losartan/hydrochlorothiazide, valsartan/hydrochlorothiazide, candesartan cilexetil, olmesartan medoxomil, irbesartan, losartan potassium, telmisartan, eprosartan, candesartan cilexetil/hydrochlorothiazide, hydrochlorothiazide/irbesartan, eprosartan/hydrochlorothiazide, hydrochlorothiazide/telmisartan, hydrochlorothiazide/olmesartan medoxomil, valsartan |
| Ssc.18459.1.S1_at | Amiloride-sensitive sodium channel alpha-subunit | 1.97 | −2.41 | 1.43 | −1.93 | SCNN1A | triamterene/hydrochlorothiazide, amiloride, amiloride/hydrochlorothiazide, triamterene |

TABLE 5-continued

Day 60 prescription.

| Probe ID | Name | Fold Change D7/ Base | Fold Change D21/ Base | Fold Change D60/ Base | Fold Change D180/ Base | Gene Symbol | DRUGS |
|---|---|---|---|---|---|---|---|
| Ssc.10287.1.A1_at | Transforming growth factor beta 2 precursor (TGF-beta 2) | 1.41 | −4.54 | 1.43 | 1.67 | TGFB2 | AP-12009 |
| Ssc.16823.1.S1_at | P2Y purinoceptor 12 (P2Y12) (P2Y12 platelet ADP receptor) (P2Y(ADP)) | 1.38 | 1.19 | 1.41 | 1.11 | P2RY12 | prasugrel, AZD 6140, clopidogrel |
| Ssc.9565.1.S1_at | Interferon-gamma receptor alpha chain | 2.92 | 1.63 | 1.41 | −1.23 | IFNGR1 | interferon gamma-1b |
| Ssc.9595.1.S1_at | Beta platelet-derived growth factor receptor | 3.48 | −3.60 | 1.40 | 1.65 | PDGFRB | dasatinib, sunitinib, axitinib, KRN-951, imatinib, sorafenib, becaplermin |
| Ssc.8046.1.A1_at | peptidylprolyl isomerase A isoform 1; cyclophilin A; | 1.16 | −1.08 | 1.39 | 1.26 | PPIA | N-methyl-4-Ile-cyclosporin |
| Ssc.1498.1.S1_at | Proteasome subunit beta type 5 | −1.81 | 1.19 | 1.38 | 5.94 | PSMB5 | bortezomib |
| Ssc.7111.1.A1_at | Ribonucleoside-diphosphate reductase M2 chain (Ribonucleotide reductase small chain) | −13.13 | 4.08 | 1.37 | 1.67 | RRM2 | gemcitabine, triapine, hydroxyurea, fludarabine phosphate |
| Ssc.19700.1.S1_at | Serine/threonine protein phosphatase 2B catalytic subunit, beta | 1.11 | 1.13 | 1.34 | 1.09 | PPP3CB | ISAtx-247, tacrolimus, pimecrolimus, cyclosporin A |
| Ssc.14258.1.S1_at | Amyloid beta A4 protein precursor (APP) (ABPP) | 1.87 | 3.33 | 1.34 | −1.02 | APP | AAB-001 |
| Ssc.6418.1.S1_at | Farnesyl-diphosphate farnesyltransferase | −1.25 | 2.31 | 1.33 | 1.08 | FDFT1 | TAK-475, zoledronic acid |
| Ssc.16096.2.S1_a_at | Mast/stem cell growth factor receptor | −1.28 | −2.63 | 1.30 | −4.71 | KIT | dasatinib, sunitinib, KRN-951, imatinib, sorafenib |
| Ssc.29149.1.A1_at | Mineralocorticoid receptor (MR) | −2.18 | −2.78 | 1.28 | −11.66 | NR3C2 | hydrochlorothiazide/spironolactone, fludrocortisone acetate, drospirenone, spironolactone, eplerenone |
| Ssc.5569.1.S1_at | Thyroid hormone receptor alpha | −10.22 | 1.26 | 1.26 | 6.49 | THRA | 3,5-diiodothyropropionic acid, amiodarone, thyroxine, L-triiodothyronine |
| Ssc.26215.1.S1_at | DNA polymerase epsilon p12 subunit (DNA polymerase epsilon subunit 4) | −1.23 | −2.71 | 1.19 | −1.04 | POLE4 | gemcitabine |
| Ssc.23234.1.S1_at | collagen, type XXIV, alpha 1 | −1.43 | 1.66 | 1.16 | 1.76 | COL24A1 | collagenase |
| Ssc.10142.1.A1_at | Dihydropyrimidine dehydrogenase [NADP+] | 2.06 | 2.17 | 1.13 | −2.68 | DPYD | eniluracil |
| Ssc.3607.1.S1_at | Interferon-alpha/beta receptor beta | 2.28 | 4.65 | 1.11 | −1.56 | IFNAR2 | interferon beta-1a, interferon alfa-2b, interferon alfacon-1, PEG-interferon alfa-2a, interferon alfa-2a/ribavirin, pegintron, interferon beta-1b, IFNA2A |
| Ssc.14475.3.S1_a_at | Peroxisome proliferator activated receptor gamma (PPAR-gamma) | 13.83 | −9.38 | 1.09 | −2.85 | PPARG | rosiglitazone, GI262570, pioglitazone, tesaglitazar, troglitazone |
| Ssc.5000.1.A1_at | Receptor protein-tyrosine kinase erbB-2 | −1.04 | −4.15 | 1.08 | 2.25 | ERBB2 | trastuzumab, BMS-599626, ARRY-334543, XL647, CP-724,714, HKI-272, lapatinib, erlotinib |
| Ssc.23505.1.S1_at | Amine oxidase [flavin-containing] A (Monoamine oxidase) (MAO-A) | −1.86 | 2.17 | 1.08 | 1.20 | MAOA | ladostigil, 1-ethylphenoxathiin 10,10-dioxide, dextroamphetamine, procainamide, tranylcypromine, phenelzine, isocarboxazid, benzphetamine, N-(2-indanyl)glycinamide |
| Ssc.19379.1.A1_at | Voltage-dependent L-type calcium channel alpha-1C | 1.83 | −1.34 | 1.07 | −3.27 | CACNA1C | clevidipine, MEM-1003, amlodipine/olmesartan medoxomil, amlodipine/benazepril, diltiazem, verapamil, mibefradil, bepridil, enalapril/felodipine, amlodipine/atorvastatin, nisoldipine, isradipine, felodipine, nimodipine, nitrendipine, amlodipine, nicardipine, nifedipine, trandolapril/verapamil, diltiazem/enalapril |
| Ssc.6713.1.S1_at | Androgen receptor (Dihydrotestosterone receptor) | −1.47 | −11.56 | 1.07 | −2.36 | AR | estradiol valerate/testosterone enanthate, estradiol cypionate/testosterone cypionate, bicalutamide, flutamide, |

TABLE 5-continued

Day 60 prescription.

| Probe ID | Name | Fold Change D7/ Base | Fold Change D21/ Base | Fold Change D60/ Base | Fold Change D180/ Base | Gene Symbol | DRUGS |
|---|---|---|---|---|---|---|---|
| | | | | | | | nandrolone decanoate, testosterone cypionate, medroxyprogesterone acetate, oxandrolone, danazol, stanozolol, spironolactone, testosterone, oxymetholone, testosterone propionate, testosterone enanthate |
| Ssc.28329.1.S1_at | DNA polymerase beta | 1.14 | 1.19 | 1.07 | 5.25 | POLB | nelarabine, clofarabine, stavudine, trifluridine, vidarabine, zalcitabine, entecavir |
| Ssc.25040.1.S1_at | Serine/threonine-protein kinase Chk1 | −3.75 | 1.11 | 1.06 | −2.45 | CHEK1 | UCN-01 (7-hydroxystaurosporine) |
| Ssc.9781.1.S1_at | Plasminogen activator inhibitor-1 (PAI-1) (Endothelial plasminogen activator inhibitor) (PAI) | −1.55 | −1.17 | 1.04 | 1.30 | SERPINE1 | drotrecogin alfa |
| Ssc.16532.1.S1_at | Cell division protein kinase 2 (p33 protein kinase). | −1.83 | −1.51 | 1.04 | 1.35 | CDK2 | BMS-387032, flavopiridol |
| Ssc.22797.1.S1_at | DNA topoisomerase II, beta | 3.15 | −1.87 | 1.02 | −2.91 | TOP2B | novobiocin, etoposide, CPI-0004Na, pixantrone, becatecarin, elsamitrucin, AQ4N, BN 80927, tafluposide, mitoxantrone, norfloxacin, dexrazoxane, tirapazamine, TAS-103, XK469, gatifloxacin, valrubicin, gemifloxacin, moxifloxacin, nemorubicin, nalidixic acid, epirubicin, doxorubicin, daunorubicin |
| Ssc.14488.1.S1_at | Glutamate carboxypeptidase II | −1.04 | 1.10 | 1.02 | 1.69 | FOLH1 | capromab pendetide |

TABLE 6

Day 180 prescription.

| Probe ID | Name | Fold Change D7/ Base | Fold Change D21/ Base | Fold Change D60/ Base | Fold Change D180/ Base | Gene Symbol | DRUGS |
|---|---|---|---|---|---|---|---|
| Ssc.11051.1.S1_at | Cell division protein kinase 4 | 1.44 | −7.67 | −4.96 | 23.75 | CDK4 | PD-0332991, flavopiridol |
| Ssc.28690.1.A1_at | Histone deacetylase 6 (HD6) | −1.92 | −1.57 | −3.58 | 20.60 | HDAC6 | tributyrin, PXD101, pyroxamide, vorinostat, FR 901228 |
| Ssc.21108.1.S1_at | Complement C5 | −17.35 | 3.21 | 618.80 | 9.28 | C5 | eculizumab |
| Ssc.5569.1.S1_at | Thyroid hormone receptor alpha | −10.22 | 1.26 | 1.26 | 6.49 | THRA | 3,5-diiodothyropropionic acid, amiodarone, thyroxine, L-triiodothyronine |
| Ssc.1498.1.S1_at | Proteasome subunit beta type 5 | −1.81 | 1.19 | 1.38 | 5.94 | PSMB5 | bortezomib |
| Ssc.13460.1.A1_at | Histone deacetylase 9 (HD9) (HD7B) (HD7). | −6.40 | 5.13 | −1.79 | 5.72 | HDAC9 | tributyrin, PXD101, pyroxamide, vorinostat, FR 901228 |
| Ssc.28329.1.S1_at | DNA polymerase beta | 1.14 | 1.19 | 1.07 | 5.25 | POLB | nelarabine, clofarabine, stavudine, trifluridine, vidarabine, zalcitabine, entecavir |
| Ssc.23793.1.S1_at | T-cell surface antigen CD2 | −3.27 | 79.25 | 93.34 | 5.20 | CD2 | alefacept, siplizumab |
| Ssc.12845.1.S1_at | Cell division protein kinase 6 | −6.56 | 5.40 | 4.77 | 5.13 | CDK6 | PD-0332991, flavopiridol |
| Ssc.24528.1.S1_at | Angiotensin-converting enzyme | −1.61 | 5.01 | 2.33 | 4.76 | ACE | pentopril, perindoprilat, amlodipine/benazepril, lisinopril/hydrochlorothiazide, benazepril, enalapril, perindopril, captopril, enalapril/felodipine, hydrochlorothiazide/moexipril, benazepril/hydrochlorothiazide, hydrochlorothiazide/quinapril, fosinopril/hydrochlorothiazide, captopril/hydrochlorothiazide, enalapril/hydrochlorothiazide, |

TABLE 6-continued

Day 180 prescription.

| Probe ID | Name | Fold Change D7/Base | Fold Change D21/Base | Fold Change D60/Base | Fold Change D180/Base | Gene Symbol | DRUGS |
|---|---|---|---|---|---|---|---|
| | | | | | | | ramipril, moexipril, quinapril, lisinopril, enalaprilat, trandolapril, trandolapril/verapamil, diltiazem/enalapril, fosinopril |
| Ssc.3040.1.S1_at | Histone deacetylase 2 (HD2) | −3.24 | 2.79 | 4.94 | 4.72 | HDAC2 | tributyrin, PXD101, pyroxamide, vorinostat, FR 901228 |
| Ssc.30373.1.A1_at | cGMP-specific 3',5'-cyclic phosphodiesterase | 4.27 | 1.52 | 2.34 | 4.09 | PDE5A | dyphylline, nitroglycerin, DA-8159, aminophylline, sildenafil, dipyridamole, aspirin/dipyridamole, vardenafil, tolbutamide, tadalafil, theophylline, pentoxifylline |
| Ssc.2714.1.S1_a_at | Proto-oncogene tyrosine-protein kinase FYN | −4.26 | 9.56 | 12.54 | 3.93 | FYN | dasatinib |
| Ssc.12937.1.S1_at | Presenilin 1 (PS-1) (S182 protein). | −14.09 | 6.21 | 2.48 | 3.79 | PSEN1 | (R)-flurbiprofen |
| Ssc.19937.1.S1_at | Inosine-5'-monophosphate dehydrogenase 2 | 1.00 | 2.69 | −1.47 | 3.65 | IMPDH2 | thioguanine, VX-944, interferon alfa-2a/ribavirin, mycophenolic acid, ribavirin |
| Ssc.16114.1.S1_at | Dihydropyridine-sensitive L-type, calcium channel alpha-2/delta | −1.96 | −4.18 | 2.24 | 3.65 | CACNA2D1 | bepridil, amlodipine, pregabalin |
| SscAffx.20.1.S1_at | T-cell surface glycoprotein CD3 gamma chain | −2.19 | 14.07 | 10.96 | 3.62 | CD3G | visilizumab, MT103 |
| Ssc.20685.1.S1_at | Apoptosis regulator Bcl-2 | −2.22 | 2.77 | 2.58 | 3.25 | BCL2 | oblimersen, (−)-gossypol |
| Ssc.11443.1.S1_at | Transcription factor p65 | −1.43 | −2.45 | −3.96 | 3.24 | RELA | NF-kappaB decoy |
| Ssc.26290.1.S1_at | Integrin beta-5 | −1.06 | −1.51 | −5.43 | 3.24 | ITGB5 | EMD121974 |
| Ssc.15932.1.S1_at | Integrin alpha-V | −6.15 | 5.79 | 2.94 | 3.14 | ITGAV | abciximab, CNTO 95, EMD121974 |
| Ssc.14471.1.S1_at | B-lymphocyte antigen CD19 | 9.54 | 3.30 | −10.32 | 3.04 | CD19 | combotox, HD37-dgRTA, MT103 |
| Ssc.16167.1.S1_at | Rho-associated protein kinase 1 | 2.40 | 2.32 | 2.83 | 3.00 | ROCK1 | fasudil, Y-27632 |
| Ssc.26200.1.S1_at | Thyroid hormone receptor beta-1. | 3.49 | −1.56 | 7.96 | 2.52 | THRB | 3,5-diiodothyropropionic acid, amiodarone, thyroxine, L-triiodothyronine |
| Ssc.3059.1.S1_at | Aldose reductase (Aldehyde reductase). | −1.74 | 1.98 | −1.66 | 2.49 | AKR1B1 | sorbinil, Zopolrestat (Alond, Pfizer), zenarestat (Fujisawa, Parke-Davis) |
| Ssc.11246.1.A1_at | Protein kinase C, alpha | −5.96 | −4.78 | 2.68 | 2.46 | PRKCA | L-threo-safingol |
| Ssc.10256.1.A1_at | cAMP-specific 3',5'-cyclic phosphodiesterase 4B | −1.89 | 6.74 | 2.20 | 2.44 | PDE4B | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.1598.1.S1_at | Retinoic acid receptor RXR-beta | −2.21 | −1.13 | −4.20 | 2.42 | RXRB | bexarotene, retinoic acid, 9-cis-retinoic acid |
| Ssc.1520.1.A1_at | Proto-oncogene tyrosine-protein kinase receptor ret | −1.05 | −1.88 | 2.00 | 2.39 | RET | sunitinb |
| Ssc.11572.1.A1_at | Histone deacetylase 3 (HD3) (RPD3-2) (SMAP45). | −1.65 | 1.67 | −1.55 | 2.36 | HDAC3 | tributyrin, PXD101, pyroxamide, MGCD0103, vorinostat, FR 901228 |
| Ssc.18051.1.S1_at | cGMP-inhibited 3',5'-cyclic phosphodiesterase B | −3.16 | 1.96 | 3.41 | 2.32 | PDE3B | dyphylline, nitroglycerin, medorinone, aminophylline, cilostazol, dipyridamole, amrinone, tolbutamide, theophylline, pentoxifylline |
| Ssc.15886.1.S1_at | Apopain precursor (Caspase-3) (CASP-3) | −3.02 | 3.64 | 2.31 | 2.29 | CASP3 | IDN-6556 |
| Ssc.5000.1.A1_at | Receptor protein-tyrosine kinase erbB-2 | −1.04 | −4.15 | 1.08 | 2.25 | ERBB2 | trastuzumab, BMS-599626, ARRY-334543, XL647, CP-724,714, HKI-272, lapatinib, erlotinib |
| Ssc.15374.1.S1_at | COL14A1 protein | 1.10 | −17.71 | 3.79 | 2.24 | COL14A1 | collagenase |
| Ssc.19873.1.S1_at | Collagen alpha 1(XVII) chain | −2.37 | 3.02 | −1.55 | 2.18 | COL17A1 | collagenase |
| Ssc.19532.1.S1_at | Guanylate cyclase soluble, beta-1 chain | −4.28 | 12.74 | 3.04 | 2.13 | GUCY1B3 | nitroglycerin, isosorbide-5-mononitrate, isosorbide dinitrate, nitroprusside, isosorbide dinitrate/hydralazine |

TABLE 6-continued

| | | Day 180 prescription. | | | | | |
|---|---|---|---|---|---|---|---|
| Probe ID | Name | Fold Change D7/Base | Fold Change D21/Base | Fold Change D60/Base | Fold Change D180/Base | Gene Symbol | DRUGS |
| Ssc.5045.1.S1_at | 3-beta-hydroxysteroid-delta(8),delta(7)-isomerase (EC 5.3.3.5) (Cholestenol delta-isomerase) (Emopamil-binding protein). | −1.55 | 1.24 | 2.19 | 2.08 | EBP | SR 31747 |
| Ssc.9272.1.S1_at | Tumor-associated calcium signal transducer 1 (EPCAM antigen) | 1.81 | 3.94 | 176.50 | 2.07 | TACSTD1 | tucotuzumab celmoleukin |
| Ssc.7139.1.S1_at | Dihydrofolate reductase | −1.13 | 1.41 | −1.12 | 2.06 | DHFR | pyrimethamine, trimethoprim, iclaprim, methotrexate, sulfisoxazole, triamterene, folic acid, trimetrexate, LY231514, PT 523 |
| Ssc.818.1.S1_at | RAF proto-oncogene serine/threonine-protein kinase | −1.40 | 2.56 | 1.58 | 1.98 | RAF1 | sorafenib |
| Ssc.25168.1.S1_a_at | Collagen alpha 1(XVI) chain | −7.23 | −3.61 | −4.45 | 1.87 | COL16A1 | collagenase |
| Ssc.3737.1.S1_at | Tubulin gamma-1 chain (Gamma-1 tubulin) ( | −1.24 | −1.88 | −1.29 | 1.82 | TUBG1 | epothilone B, ixabepilone, colchicine/probenecid, XRP9881, E7389, AL 108, EC145, NPI-2358, milataxel, TPI 287, TTI-237, docetaxel, vinflunine, vinorelbine, vincristine, vinblastine, paclitaxel, podophyllotoxin, colchicine |
| Ssc.23234.1.S1_at | collagen, type XXIV, alpha 1 | −1.43 | 1.66 | 1.16 | 1.76 | COL24A1 | collagenase |
| Ssc.16000.1.A1_at | Vascular endothelial growth factor receptor 1 | 1.08 | −3.40 | 3.34 | 1.72 | FLT1 | sunitinib, axitinib, CEP 7055 |
| Ssc.14488.1.S1_at | Glutamate carboxypeptidase II | −1.04 | 1.10 | 1.02 | 1.69 | FOLH1 | capromab pendetide |
| Ssc.7176.1.A1_at | C—X—C chemokine receptor type 4 (CXC-R4) (CXCR-4) | 3.74 | 10.91 | 8.15 | 1.68 | CXCR4 | JM 3100 |
| Ssc.10287.1.A1_at | Transforming growth factor beta 2 | 1.41 | −4.54 | 1.43 | 1.67 | TGFB2 | AP-12009 |
| Ssc.7111.1.A1_at | Ribonucleoside-diphosphate reductase M2 chain | −13.13 | 4.08 | 1.37 | 1.67 | RRM2 | gemcitabine, triapine, hydroxyurea, fludarabine phosphate |
| Ssc.9595.1.S1_at | Beta platelet-derived growth factor receptor | 3.48 | −3.60 | 1.40 | 1.65 | PDGFRB | dasatinib, sunitinib, axitinib, KRN-951, imatinib, sorafenib, becaplermin |
| Ssc.5826.1.A1_at | Macrophage colony stimulating factor I receptor | 1.93 | −4.97 | −13.18 | 1.61 | CSF1R | sunitinib |
| Ssc.17518.1.S1_at | Adenosine A1 receptor | −3.16 | 3.44 | −1.56 | 1.58 | ADORA1 | adenosine, dyphylline, aminophylline, clofarabine, theophylline, caffeine, tecadenoson |
| Ssc.19691.1.S1_at | Platelet-activating factor acetylhydrolase | 1.59 | 1.16 | 3.01 | 1.47 | PLA2G7 | darapladib |
| Ssc.9523.1.A1_at | Methylated-DNA--protein-cysteine methyltransferase | 1.55 | −1.17 | 3.35 | 1.47 | MGMT | O6-benzylguanine |
| Ssc.11406.1.A1_a_at | Interleukin-1 receptor, type I | 1.03 | 2.70 | −2.44 | 1.42 | IL1R1 | anakinra |
| Ssc.11085.1.S1_at | Glucagon-like peptide 2 receptor | −1.08 | −1.17 | −1.26 | 1.40 | GLP2R | teduglutide |
| Ssc.10591.1.A1_at | Metabotropic glutamate receptor 5 | −7.83 | 1.54 | −1.31 | 1.40 | GRM5 | fasoracetam |
| Ssc.9034.1.A1_at | Proteinase activated receptor 1 | −1.29 | 3.75 | −1.40 | 1.37 | F2R | chrysalin, argatroban, bivalirudin |
| Ssc.10360.1.S1_at | B-Raf proto-oncogene serine/threonine-protein kinase | −2.15 | 1.26 | 3.09 | 1.36 | BRAF | sorafenib |
| Ssc.16532.1.S1_at | Cell division protein kinase 2 | −1.83 | −1.51 | 1.04 | 1.35 | CDK2 | BMS-387032, flavopiridol |
| Ssc.9781.1.S1_at | Plasminogen activator inhibitor-1 precursor (PAI-1) (Endothelial plasminogen activator inhibitor) (PAI) | −1.55 | −1.17 | 1.04 | 1.30 | SERPINE1 | drotrecogin alfa |
| Ssc.26328.1.S1_at | C-C chemokine receptor type 5 (CCR5) (CD195 antigen) | −2.53 | 5.61 | 3.25 | 1.29 | CCR5 | maraviroc, vicriviroc, SCH 351125 |
| Ssc.8046.1.A1_at | peptidylprolyl isomerase A isoform 1; cyclophilin A; | 1.16 | −1.08 | 1.39 | 1.26 | PPIA | N-methyl-4-Ile-cyclosporin |
| Ssc.11302.1.S1_at | Collagen alpha 1(III) chain | −1.80 | 2.02 | 2.06 | 1.26 | COL3A1 | collagenase |
| Ssc.13186.1.S1_at | Cell division protein kinase 7 | −1.08 | 2.38 | 4.34 | 1.24 | CDK7 | BMS-387032, flavopiridol |
| Ssc.27603.1.S1_at | Endothelin B receptor | 5.30 | −3.27 | 15.99 | 1.23 | EDNRB | bosentan, sitaxsentan, atrasentan |

TABLE 6-continued

Day 180 prescription.

| Probe ID | Name | Fold Change D7/Base | Fold Change D21/Base | Fold Change D60/Base | Fold Change D180/Base | Gene Symbol | DRUGS |
|---|---|---|---|---|---|---|---|
| Ssc.27093.1.A1_at | cAMP-specific 3',5'-cyclic phosphodiesterase 4C | −6.34 | −2.27 | −7.97 | 1.23 | PDE4C | dyphylline, nitroglycerin, arofylline, tetomilast, L869298, aminophylline, anagrelide, cilomilast, milrinone, rolipram, dipyridamole, L-826,141, roflumilast, tolbutamide, theophylline, pentoxifylline, caffeine |
| Ssc.20904.1.A1_at | RAC-gamma serine/threonine-protein kinase | −1.34 | 3.01 | −2.18 | 1.23 | AKT3 | enzastaurin |
| Ssc.23505.1.S1_at | Amine oxidase [flavin-containing] A (Monoamine oxidase) (MAO-A) | −1.86 | 2.17 | 1.08 | 1.20 | MAOA | ladostigil, 1-ethylphenoxathiin 10,10-dioxide, dextroamphetamine, procainamide, tranylcypromine, phenelzine, isocarboxazid, benzphetamine, N-(2-indanyl)glycinamide |
| Ssc.15312.1.S1_at | Histone deacetylase 4 (HD4) | −1.93 | 2.85 | −2.41 | 1.20 | HDAC4 | tributyrin, PXD101, pyroxamide, vorinostat, FR 901228 |
| Ssc.9019.1.A1_at | Atrial natriuretic peptide clearance receptor | −1.09 | −1.69 | 5.31 | 1.18 | NPR3 | nesiritide |
| Ssc.16160.1.S1_at | T lymphocyte activation antigen CD86 | −1.55 | 3.88 | −1.37 | 1.18 | CD86 | abatacept |
| Ssc.1844.1.S1_at | Atrial natriuretic peptide receptor B | −1.94 | −1.06 | −1.63 | 1.13 | NPR2 | nesiritide |
| Ssc-11171.1.S1_at | Adenosine deaminase | 1.32 | −2.04 | −3.23 | 1.12 | ADA | pentostatin, vidarabine |
| Ssc.16823.1.S1_at | P2Y purinoceptor 12 (P2Y12) (P2Y12 platelet ADP receptor) | 1.38 | 1.19 | 1.41 | 1.11 | P2RY12 | prasugrel, AZD 6140, clopidogrel |
| Ssc.19700.1.S1_at | Serine/threonine protein phosphatase 2B catalytic subunit, beta | 1.11 | 1.13 | 1.34 | 1.09 | PPP3CB | ISAtx-247, tacrolimus, pimecrolimus, cyclosporin A |
| Ssc.26752.1.S1_at | 5-hydroxytryptamine (serotonin) receptor 3B | −3.57 | 1.22 | 1.60 | 1.08 | HTR3B | cisapride, granisetron, ondansetron, fenfluramine, palonosetron, mirtazapine, alosetron, D-tubocurarine, ergotamine, dolasetron |
| Ssc.6418.1.S1_at | Farnesyl-diphosphate farnesyltransferase | −1.25 | 2.31 | 1.33 | 1.08 | FDFT1 | TAK-475, zoledronic acid |
| Ssc.22477.1.S1_at | Collagen alpha 1(IV) chain | 1.58 | −5.08 | −1.78 | 1.04 | COL4A1 | collagenase |
| Ssc.31192.1.S1_at | Collagen alpha 1(XVIII) chain | −1.89 | −1.36 | −19.06 | 1.03 | COL18A1 | collagenase |
| Ssc.1091.1.S1_at | Collagen alpha 1(I) chain | −3.27 | −17.59 | 2.07 | 1.03 | COL1A1 | collagenase |
| Ssc.7581.1.A1_at | FL cytokine receptor | 1.69 | 1.04 | −1.81 | 1.01 | FLT3 | CHIR-258, sorafenib, lestaurtinib, CGP 41251 |

TABLE 7

Upregulated gene targets at all timepoints (Days 7, 21, 60, and 180 relative to baseline) of PAH progression with available drugs

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.28329.1.S1_at | DNA polymerase beta | 1.14 | 1.19 | 1.07 | 5.25 | POLB | nelarabine, clofarabine, stavudine, trifluridine, vidarabine, zalcitabine, entecavir |
| Ssc.9272.1.S1_at | Tumor-associated calcium signal transducer 1 (EPCAM antigen) | 1.81 | 3.94 | 176.50 | 2.07 | TACSTD1 | tucotusumab celmoleukin |
| Ssc.7176.1.A1_at | C—X—C chemokine receptor type 4 (CXC-R4) (CXCR-4) (CD184 antigen) | 3.74 | 10.91 | 8.15 | 1.68 | CXCR4 | JM 3100 (1,1'-(1,4-phenylenebis{methylene})}bis(1,4,8,11-tetraazacyclotetradecane)octahydrochloride dihydrate) |
| Ssc.19691.1.S1_at | Platelet-activating factor acetylhydrolase | 1.59 | 1.16 | 3.01 | 1.47 | PLA2G7 | darapladib |

TABLE 7-continued

Upregulated gene targets at all timepoints (Days 7, 21, 60, and 180 relative to baseline) of PAH progression with available drugs

| Probe ID | Name | Fold Change D7/ Base | Fold Change D21/ Base | Fold Change D60/ Base | Fold Change D180/ Base | Gene Symbol | Drugs |
|---|---|---|---|---|---|---|---|
| Ssc.16823.1.S1_at | P2Y purinoceptor 12 (P2Y12) | 1.38 | 1.19 | 1.41 | 1.11 | P2RY12 | prasugrel, AZD 6140 (Ticagrelor), clopidogrel |
| Ssc.19700.1.S1_at | Serine/threonine protein phosphatase 2B catalytic subunit, beta isoform | 1.11 | 1.13 | 1.34 | 1.09 | PPP3CB | ISAtx-247, tacrolimus, pimecrolimus, cyclosporin A |
| Ssc.14258.1.S1_at | Amyloid beta A4 protein | 1.87 | 3.33 | 1.34 | −1.02 | APP | Bapineuzumab (AAB-001) |
| Ssc.8726.1.A1_at | Amidophosphoribosyltransferase | 1.03 | 1.24 | 4.16 | −1.11 | PPAT | thioguanine, azathioprine, 6-mercaptopurine, |

TABLE 8

Upregulated gene targets at Days 21 and 60 (relative to baseline) of PAH progression with available drugs

| Probe ID | Name | Fold Change D7/Base | Fold Change D21/Base | Fold Change D60/Base | Fold Change D180/Base |
|---|---|---|---|---|---|
| Ssc.21108.1.S1_at | Complement C5 | −17.35 | 3.21 | 618.80 | 9.28 |
| Ssc.9272.1.S1_at | Tumor-associated calcium signal transducer 1 | 1.81 | 3.94 | 176.50 | 2.07 |
| Ssc.23793.1.S1_at | T-cell surface antigen CD2 | −3.27 | 79.25 | 93.34 | 5.20 |
| Ssc.17245.1.S1_at | Interleukin-13 receptor alpha-1 chain | −1.99 | 23.04 | 21.92 | 7.16 |
| Ssc.15999.1.A1_at | Vascular endothelial growth factor receptor 2 | 1.24 | 1.24 | 18.52 | −11.02 |
| Ssc.2714.1.S1_a_at | Proto-oncogene tyrosine-protein kinase FYN | −4.26 | 9.56 | 12.54 | 3.93 |
| SscAffx.20.1.S1_at | T-cell surface glycoprotein CD3 gamma chain | −2.19 | 14.07 | 10.96 | 3.62 |
| Ssc.7176.1.A1_at | C—X—C chemokine receptor type 4 (CXC-R4) (CXCR-4) ( | 3.74 | 10.91 | 8.15 | 1.68 |
| Ssc.7297.1.S1_at | Amine oxidase [flavin-containing] B (EC 1.4.3.4) (Monoamine oxidase) (MAO-B). | 1.16 | 6.42 | 7.02 | −1.13 |
| Ssc.20438.1.S1_at | Prostaglandin F2-alpha receptor (PGF2 alpha receptor) | −3.20 | 2.13 | 5.28 | −38.97 |
| Ssc.3040.1.S1_at | Histone deacetylase 2 (HD2). | −3.24 | 2.79 | 4.94 | 4.72 |
| Ssc.12845.1.S1_at | Cell division protein kinase 6 (E | −6.56 | 5.40 | 4.77 | 5.13 |
| Ssc.13186.1.S1_at | Cell division protein kinase 7 | −1.08 | 2.38 | 4.34 | 1.24 |
| Ssc.8726.1.A1_at | Amidophosphoribosyltransferase | 1.03 | 1.24 | 4.16 | −1.11 |
| Ssc.15878.1.S1_at | Serine/threonine protein phosphatase 2B catalytic subunit, alpha isoform | 1.85 | 3.22 | 3.62 | −1.49 |

TABLE 8-continued

Upregulated gene targets at Days 21 and 60 (relative to baseline) of PAH progression with available drugs

| | | | | | |
|---|---|---|---|---|---|
| Ssc.26351.1.S1_at | cAMP-specific 3',5'-cyclic phosphodiesterase 4D (EC 3.1.4.17) (DPDE3) (PDE43). [Source: Uniprot/SWISSPROT; Acc: Q08499] | 4.67 | 4.99 | 3.61 | −1.15 |
| Ssc.15801.1.A1_at | Protein kinase C, beta type (EC 2.7.1.37) (PKC-beta) (PKC-B). [Source: Uniprot/SWISSPROT; Acc: P05771] | 3.36 | 6.36 | 3.53 | −4.98 |
| Ssc.24966.1.S1_at | Purine nucleoside phosphorylase | −3.34 | 3.12 | 3.46 | −1.14 |
| Ssc.18051.1.S1_at | cGMP-inhibited 3',5'-cyclic phosphodiesterase B | −3.16 | 1.96 | 3.41 | 2.32 |
| Ssc.26328.1.S1_at | C-C chemokine receptor type 5 (C-C CKR-5) (CC-CKR-5) (CCR-5) (CCR5) (HIV-1 fusion coreceptor) (CHEMR13) (CD195 antigen). [Source: Uniprot/SWISSPROT; Acc: P51681] | −2.53 | 5.61 | 3.25 | 1.29 |
| Ssc.17224.1.S1_at | Toll-like receptor 8 precursor. [Source: Uniprot/SWISSPROT; Acc: Q9NR97] | 1.17 | 6.49 | 3.13 | −1.52 |
| Ssc.21011.1.S1_at | Collagen alpha 2(I) chain precursor. [Source: Uniprot/SWISSPROT; Acc: P08123] | −2.70 | 1.24 | 3.12 | −1.01 |
| Ssc.10360.1.S1_at | B-Raf proto-oncogene serine/threonine-protein kinase (v-Raf murine sarcoma viral oncogene homolog B1). | −2.15 | 1.26 | 3.09 | 1.36 |
| Ssc.19532.1.S1_at | Guanylate cyclase soluble, beta-1 | −4.28 | 12.74 | 3.04 | 2.13 |
| Ssc.19691.1.S1_at | Platelet-activating factor acetylhydrolase | 1.59 | 1.16 | 3.01 | 1.47 |
| Ssc.17155.1.A1_at | heparanase; heparanase-1 | 4.81 | 5.38 | 2.98 | −1.83 |
| Ssc.15932.1.S1_at | Integrin alpha-V | −6.15 | 5.79 | 2.94 | 3.14 |
| Ssc.11381.1.S1_at | Interferon-alpha/beta receptor alpha chain precursor (IFN-alpha-REC). [Source: Uniprot/SWISSPROT; Acc: P17181] | 10.45 | 8.08 | 2.61 | −1.30 |
| Ssc.20685.1.S1_at | Apoptosis regulator Bcl-2. [Source: Uniprot/SWISSPROT; Acc: P10415] | −2.22 | 2.77 | 2.58 | 3.25 |
| Ssc.12937.1.S1_at | Presenilin 1 (PS-1) (S182 protein). | −14.09 | 6.21 | 2.48 | 3.79 |
| Ssc.6801.1.S1_at | Proto-oncogene tyrosine-protein kinase YES | −1.06 | 1.69 | 2.36 | −1.82 |
| Ssc.24528.1.S1_at | Angiotensin-converting enzyme | −1.61 | 5.01 | 2.33 | 4.76 |
| Ssc.15886.1.S1_at | Apopain (Caspase-3) (CASP-3 | −3.02 | 3.64 | 2.31 | 2.29 |
| Ssc.10256.1.A1_at | cAMP-specific 3',5'-cyclic phosphodiesterase 4B | −1.89 | 6.74 | 2.20 | 2.44 |
| Ssc.5045.1.S1_at | 3-beta-hydroxysteroid-delta(8),delta(7)-isomerase | −1.55 | 1.24 | 2.19 | 2.08 |

TABLE 8-continued

Upregulated gene targets at Days 21 and 60 (relative to baseline) of PAH progression with available drugs

| | | | | | |
|---|---|---|---|---|---|
| Ssc.16145.1.A1_at | 5-hydroxytryptamine 2B receptor (5-HT-2B) (Serotonin receptor 2B). | 1.08 | 2.10 | 2.15 | 5.45 |
| Ssc.16186.1.S1_at | T-cell surface glycoprotein CD3 epsilon chain | 9.00 | 3.12 | 2.12 | −5.66 |
| Ssc.11302.1.S1_at | Collagen alpha 1(III) chain precursor. | −1.80 | 2.02 | 2.06 | 1.26 |
| Ssc.19673.1.S1_at | T-cell surface glycoprotein CD3 delta chain precursor (T-cell receptor T3 delta chain). | 6.40 | 2.70 | 2.03 | −11.77 |
| Ssc.6710.1.A1_at | Ribonucleoside-diphosphate reductase M1 chain (Ribonucleotide reductase large chain | −1.90 | 1.44 | 2.01 | −1.01 |
| Ssc.11147.1.S1_at | Aldehyde dehydrogenase, mitochondrial precursor (ALDH class 2) (ALDHI) (ALDH-E2). | 3.18 | 1.13 | 2.00 | −1.68 |
| Ssc.15739.1.S1_at | Cytokine receptor common gamma chain (Interleukin-2 receptor gamma chain) (IL-2R gamma chain) (CD132 antigen). | −1.12 | 9.42 | 1.90 | −1.28 |
| Ssc.15822.1.S1_at | Coagulation factor V precursor (Activated protein C cofactor). | 1.92 | 3.76 | 1.89 | −1.75 |
| Ssc.4756.1.A1_at | Adenosine A3 receptor. | 2.15 | 2.10 | 1.88 | −1.81 |
| Ssc.12791.1.A1_at | 3-hydroxy-3-methylglutaryl-coenzyme A reductase | 3.27 | 2.77 | 1.77 | −2.56 |
| Ssc.818.1.S1_at | RAF proto-oncogene serine/threonine-protein kinase | −1.40 | 2.56 | 1.58 | 1.98 |
| Ssc.16823.1.S1_at | P2Y purinoceptor 12 (P2Y12) (P2Y12 platelet ADP receptor) | 1.38 | 1.19 | 1.41 | 1.11 |
| Ssc.9565.1.S1_at | Interferon-gamma receptor alpha chain (CD119 antigen) | 2.92 | 1.63 | 1.41 | −1.23 |
| Ssc.1498.1.S1_at | Proteasome subunit beta type 5 | −1.81 | 1.19 | 1.38 | 5.94 |
| Ssc.7111.1.A1_at | Ribonucleoside-diphosphate reductase M2 chain | −13.13 | 4.08 | 1.37 | 1.67 |
| Ssc.19700.1.S1_at | Serine/threonine protein phosphatase 2B catalytic subunit, beta | 1.11 | 1.13 | 1.34 | 1.09 |
| Ssc.14258.1.S1_at | Amyloid beta A4 protein | 1.87 | 3.33 | 1.34 | −1.02 |
| Ssc.6418.1.S1_at | Farnesyl-diphosphate farnesyltransferase | −1.25 | 2.31 | 1.33 | 1.08 |
| Ssc.5569.1.S1_at | Thyroid hormone receptor alpha (C-erbA-alpha) (c-erbA-1) | −10.22 | 1.26 | 1.26 | 6.49 |
| Ssc.23234.1.S1_at | collagen, type XXIV, alpha 1 | −1.43 | 1.66 | 1.16 | 1.76 |
| Ssc.10142.1.A1_at | Dihydropyrimidine dehydrogenase [NADP+] | 2.06 | 2.17 | 1.13 | −2.68 |

TABLE 8-continued

Upregulated gene targets at Days 21 and 60 (relative to baseline) of PAH progression with available drugs

| | | | | | |
|---|---|---|---|---|---|
| Ssc.3607.1.S1_at | Interferon-alpha/beta receptor beta chain | 2.28 | 4.65 | 1.11 | −1.56 |
| Ssc.23505.1.S1_at | Amine oxidase [flavin-containing] A | −1.86 | 2.17 | 1.08 | 1.20 |
| Ssc.28329.1.S1_at | DNA polymerase | 1.14 | 1.19 | 1.07 | 5.25 |
| Ssc.25040.1.S1_at | Serine/threonine-protein kinase Chk1 | −3.75 | 1.11 | 1.06 | −2.45 |
| Ssc.26379.1.S1_at | Glutamate [NMDA] receptor subunit epsilon 3 | −1.32 | 1.37 | 1.03 | −2.59 |
| Ssc.14488.1.S1_at | Glutamate carboxypeptidase II | −1.04 | 1.10 | 1.02 | 1.69 |

| Probe ID | Gene Symbol | Drugs |
|---|---|---|
| Ssc.21108.1.S1_at | C5 | eculizumab |
| Ssc.9272.1.S1_at | TACSTD1 | tucctuzumab celmoleukin |
| Ssc.23793.1.S1_at | CD2 | alefacept, siplizumab |
| Ssc.17245.1.S1_at | IL13RA1 | cintredekin besudotox |
| Ssc.15999.1.A1_at | KDR | AEE 788, sunitinib, AZD 2171, pazopanib, XL647, CEP 7055, BMS-582664, KRN-951, vatalanib, sorafenib, vandetanib, pegaptanib |
| Ssc.2714.1.S1_a_at | FYN | dasatinib |
| SscAffx.20.1.S1_at | CD3G | visilizumab, MT103 |
| Ssc.7176.1.A1_at | CXCR4 | JM 3100 |
| Ssc.7297.1.S1_at | MAOB | safinamide, ladostigil, rasagiline, selegiline, dextroamphetamine, procainamide, tranylcypromine, phenelzine, isocarboxazid, benzphetamine |
| Ssc.20438.1.S1_at | PTGFR | tafluprost, travoprost, isopropyl unoprostone, bimatoprost, latanoprost |
| Ssc.3040.1.S1_at | HDAC2 | tributyrin, PXD101, pyroxamide, vorinostat, FR 901228 |
| Ssc.12845.1.S1_at | CDK6 | PD-0332991, flavopiridol |
| Ssc.13186.1.S1_at | CDK7 | BMS-387032, flavopiridol |
| Ssc.8726.1.A1_at | PPAT | 6-mercaptopurine, thioguanine, azathioprine |
| Ssc.15878.1.S1_at | PPP3CA | ISAtx-247, tacrolimus, pimecrolimus, cyclosporin A |
| Ssc.26351.1.S1_at | PDE4D | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.15801.1.A1_at | PRKCB1 | enzastaurin, ruboxistaurin |
| Ssc.24966.1.S1_at | NP | forodesine, 9-deaza-9-(3-thienylmethyl)guanine |
| Ssc.18051.1.S1_at | PDE3B | dyphylline, nitroglycerin, medorinone, aminophylline, cilostazol, dipyridamole, amrinone, tolbutamide, theophylline, pentoxifylline |
| Ssc.26328.1.S1_at | CCR5 | maraviroc, vicriviroc, SCH 351125 |
| Ssc.17224.1.S1_at | TLR8 | resiquimod |
| Ssc.21011.1.S1_at | COL1A2 | collagenase |
| Ssc.10360.1.S1_at | BRAF | sorafenib |
| Ssc.19532.1.S1_at | GUCY1B3 | nitroglycerin, isosorbide-5-mononitrate, isosorbide dinitrate, nitroprusside, isosorbide dinitrate/hydralazine |
| Ssc.19691.1.S1_at | PLA2G7 | darapladib |
| Ssc.17155.1.A1_at | HPSE | heparanase inhibitor PI-88 |
| Ssc.15932.1.S1_at | ITGAV | abciximab, CNTO 95, EMD121974 (Cilengitide) |
| Ssc.11381.1.S1_at | IFNAR1 | interferon beta-1a, interferon alfa-2b, interferon alfacon-1, PEG-interferon alfa-2a, interferon alfa-2a/ribavirin, pegintron, interferon beta-1b, IFNA2A |
| Ssc.20685.1.S1_at | BCL2 | Oblimersen (Augmerosen), |
| Ssc.12937.1.S1_at | PSEN1 | (R)-flurbiprofen (Tarenflurbil) |
| Ssc.6801.1.S1_at | YES1 | dasatinib |
| Ssc.24528.1.S1_at | ACE | pentopril, perindoprilat, amlodipine/benazepril, lisinopril/hydrochlorothiazide, benazepril, enalapril, perindopril, |

TABLE 8-continued

Upregulated gene targets at Days 21 and 60 (relative to baseline) of PAH progression with available drugs

| | | |
|---|---|---|
| | | captopril, enalapril/felodipine, hydrochlorothiazide/moexipril, benazepril/hydrochlorothiazide, hydrochlorothiazide/quinapril, fosinopril/hydrochlorothiazide, captopril/hydrochlorothiazide, enalapril/hydrochlorothiazide, ramipril, moexipril, quinapril, lisinopril, enalaprilat, trandolapril, trandolapril/verapamil, diltiazem/enalapril, fosinopril |
| Ssc.15886.1.S1_at | CASP3 | IDN-6556 |
| Ssc.10256.1.A1_at | PDE4B | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.5045.1.S1_at | EBP | SR 31747 |
| Ssc.16145.1.A1_at | HTR2B | risperidone, buspirone, blonanserin, asenapine, eletriptan, epinastine, fenfluramine, quetiapine, nefazodone, mirtazapine, dihydroergotamine, apomorphine, ergotamine |
| Ssc.16186.1.S1_at | CD3E | visilizumab, MT103, muromonab-CD3 |
| Ssc.11302.1.S1_at | COL3A1 | collagenase |
| Ssc.19673.1.S1_at | CD3D | visilizumab, MT103 |
| Ssc.6710.1.A1_at | RRM1 | gemcitabine, clofarabine, fludarabine phosphate |
| Ssc.11147.1.S1_at | ALDH2 | disulfiram, chlorpropamide |
| Ssc.15739.1.S1_at | IL2RG | aldesleukin, denileukin diftitox |
| Ssc.15822.1.S1_at | F5 | drotrecogin alfa |
| Ssc.4756.1.A1_at | ADORA3 | adenosine, dyphylline, aminophylline, clofarabine, theophylline, caffeine |
| Ssc.12791.1.A1_at | HMGCR | aspirin/pravastatin, lovastatin/niacin, ezetimibe/simvastatin, amlodipine/atorvastatin, fluvastatin, cerivastatin, atorvastatin, pravastatin, simvastatin, lovastatin, rosuvastatin |
| Ssc.818.1.S1_at | RAF1 | sorafenib |
| Ssc.16823.1.S1_at | P2RY12 | prasugrel, AZD 6140 (Ticagrelor), clopidogrel |
| Ssc.9565.1.S1_at | IFNGR1 | interferon gamma-1b |
| Ssc.1498.1.S1_at | PSMB5 | bortezomib |
| Ssc.7111.1.A1_at | RRM2 | gemcitabine, triapine, hydroxyurea, fludarabine phosphate |
| Ssc.19700.1.S1_at | PPP3CB | ISAtx-247, tacrolimus, pimecrolimus, cyclosporin A |
| Ssc.14258.1.S1_at | APP | AAB-001 (Bapineuzumab) |
| Ssc.6418.1.S1_at | FDFT1 | TAK-475, zoledronic acid |
| Ssc.5569.1.S1_at | THRA | 3,5-diiodothyropropionic acid, amiodarone, thyroxine, L-triiodothyronine |
| Ssc.23234.1.S1_at | COL24A1 | collagenase |
| Ssc.10142.1.A1_at | DPYD | eniluracil |
| Ssc.3607.1.S1_at | IFNAR2 | interferon beta-1a, interferon alfa-2b, interferon alfacon-1, PEG-interferon alfa-2a, interferon alfa-2a/ribavirin, pegintron, interferon beta-1b, IFNA2A |
| Ssc.23505.1.S1_at | MAOA | ladostigil, 1-ethylphenoxathiin 10,10-dioxide, dextroamphetamine, procainamide, tranylcypromine, phenelzine, isocarboxazid, benzphetamine, N-(2-indanyl)glycinamide |
| Ssc.28329.1.S1_at | POLB | nelarabine, clofarabine, stavudine, trifluridine, vidarabine, zalcitabine, entecavir |
| Ssc.25040.1.S1_at | CHEK1 | UCN-01 (7-hydroxystaurosporine) |
| Ssc.26379.1.S1_at | GRIN2C | dextromethorphan/guaifenesin, morphine/dextromethorphan, neramexane, SPM 927, bicifadine, delucemine, CR 2249, besonprodil, UK-240455, ketamine, felbamate, memantine, orphenadrine, cycloserine, N-(2-indanyl)glycinamide, dextromethorphan, brompheniramine/dextromethorphan/pseudoephedrine, chlorpheniramine/dextromethorphan/phenylephrine, |

TABLE 8-continued

Upregulated gene targets at Days 21 and 60 (relative to baseline) of PAH progression with available drugs

| | | |
|---|---|---|
| Ssc.14488.1.S1_at | FOLH1 | carbinoxamine/dextromethorphan/pseudoephedrine, dextromethorphan/promethazine, 1-aminocyclopropane-1-carboxylic acid capromab pendetide |

TABLE 9

Upregulated gene targets at Days 21, 60 and 180 (relative to baseline) of PAH progression with available drugs

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.23793.1.S1_at | T-cell surface antigen CD2 | −3.27 | 79.25 | 93.34 | 5.20 | CD2 | alefacept, siplizumab |
| SscAffx.20.1.S1_at | T-cell surface glycoprotein CD3 gamma chain | −2.19 | 14.07 | 10.96 | 3.62 | CD3G | visilizumab, MT103 |
| Ssc.19532.1.S1_at | Guanylate cyclase soluble, beta-1 chain | −4.28 | 12.74 | 3.04 | 2.13 | GUCY1B3 | nitroglycerin, isosorbide-5-mononitrate, isosorbide dinitrate, nitroprusside, isosorbide dinitrate/hydralazine |
| Ssc.7176.1.A1_at | C—X—C chemokine receptor type 4 (CXC-R4) (CXCR-4) | 3.74 | 10.91 | 8.15 | 1.68 | CXCR4 | JM 3100 (1,1'-(1,4-phenylenebis(methylene))bis(1,4,8,11-tetraazacyclotetradecane)octahydrochloride dihydrate) |
| Ssc.2714.1.S1_a_at | Proto-oncogene tyrosine-protein kinase FYN | −4.26 | 9.56 | 12.54 | 3.93 | FYN | dasatinib |
| Ssc.10256.1.A1_at | cAMP-specific 3',5'-cyclic phosphodiesterase 4B | −1.89 | 6.74 | 2.20 | 2.44 | PDE4B | dyphylline, nitroglycerin, arofylline, tetomilast, L 869298, aminophylline, anagrelide, cilomilast, milrinone, rolipram, dipyridamole, L-826,141, roflumilast, tolbutamide, theophylline, pentoxifylline, caffeine |
| Ssc.12937.1.S1_at | Presenilin 1 (PS-1) (S182 protein). | −14.09 | 6.21 | 2.48 | 3.79 | PSEN1 | (R)-flurbiprofen |
| Ssc.15932.1.S1_at | Integrin alpha-V | −6.15 | 5.79 | 2.94 | 3.14 | ITGAV | abciximab, CNTO 95, EMD121974 (Cilengitide) |
| Ssc.26328.1.S1_at | C-C chemokine receptor type 5 (CCR5) | −2.53 | 5.61 | 3.25 | 1.29 | CCR5 | maraviroc, vicriviroc, SCH 351125 |
| Ssc.12845.1.S1_at | Cell division protein kinase 6 | −6.56 | 5.40 | 4.77 | 5.13 | CDK6 | PD-0332991, flavopiridol |
| Ssc.24528.1.S1_at | Angiotensin-converting enzyme | −1.61 | 5.01 | 2.33 | 4.76 | ACE | pentopril, perindoprilat, amlodipine/benazepril, lisinopril/hydrochlorothiazide, benazepril, enalapril, perindopril, captopril, enalapril/felodipine, hydrochlorothiazide/moexipril, benazepril/hydrochlorothiazide, hydrochlorothiazide/quinapril, fosinopril/hydrochlorothiazide, captopril/hydrochlorothiazide, enalapril/hydrochlorothiazide, ramipril, moexipril, quinapril, lisinopril, enalaprilat, trandolapril, trandolapril/verapamil, diltiazem/enalapril, fosinopril |
| Ssc.7130.1.S1_at | Phenylalanine-4-hydroxylase | 4.70 | 4.71 | 11.30 | 1.48 | PAH | (6R)-tetrahydrobiopterin |
| Ssc.7111.1.A1_at | Ribonucleoside-diphosphate reductase M2 chain (Ribonucleotide reductase small chain). | −13.13 | 4.08 | 1.37 | 1.67 | RRM2 | gemcitabine, triapine, hydroxyurea, fludarabine phosphate |
| Ssc.9272.1.S1_at | Tumor-associated calcium signal transducer 1 (EPCAM antigen) | 1.81 | 3.94 | 176.50 | 2.07 | TACSTD1 | tucotuzumab celmoleukin |
| Ssc.15886.1.S1_at | Apopain (Caspase-3) (CASP-3) | −3.02 | 3.64 | 2.31 | 2.29 | CASP3 | IDN-6556 |
| Ssc.21108.1.S1_at | Complement C5 | −17.35 | 3.21 | 618.80 | 9.28 | C5 | eculizumab |

TABLE 9-continued

Upregulated gene targets at Days 21, 60 and 180 (relative to baseline) of PAH progression with available drugs

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.3040.1.S1_at | Histone deacetylase 2 (HD2). | −3.24 | 2.79 | 4.94 | 4.72 | HDAC2 | tributyrin, PXD101, pyroxamide, vorinostat, FR 901228 |
| Ssc.20685.1.S1_at | Apoptosis regulator Bcl-2 | −2.22 | 2.77 | 2.58 | 3.25 | BCL2 | oblimersen, (−)-gossypol |
| Ssc.818.1.S1_at | RAF proto-oncogene serine/threonine-protein kinase | −1.40 | 2.56 | 1.58 | 1.98 | RAF1 | sorafenib |
| Ssc.13186.1.S1_at | Cell division protein kinase 7 | −1.08 | 2.38 | 4.34 | 1.24 | CDK7 | BMS-387032, flavopiridol |
| Ssc.6418.1.S1_at | Farnesyl-diphaosphate farnesyltransferase | −1.25 | 2.31 | 1.33 | 1.08 | FDFT1 | TAK-475, zoledronic acid |
| Ssc.23505.1.S1_at | Amine oxidase (flavin-containing) A (Monoamine oxidase) (MAO-A). | −1.86 | 2.17 | 1.08 | 1.20 | MAOA | ladostigil, 1-ethylphenoxathiin 10,10-dioxide, dextroamphetamine, procainamide, tranylcypromine, phenelzine, isocarboxazid, benzphetamine, N-(2-indanyl)glycinamide |
| Ssc.11302.1.S1_at | Collagen alpha 1(III) chain precursor. | −1.80 | 2.02 | 2.06 | 1.26 | COL3A1 | collagenase |
| Ssc.18051.1.S1_at | cGMP-inhibited 3',5'-cyclic phosphodiesterase B | −3.16 | 1.96 | 3.41 | 2.32 | PDE3B | dyphylline, nitroglycerin, medorinone, aminophylline, cilostazol, dipyridamole, amrinone, tolbutamide, theophylline, pentoxifylline |
| Ssc.23234.1.S1_at | collagen, type XXIV, alpha 1 | −1.43 | 1.66 | 1.16 | 1.76 | COL24A1 | collagenase |
| Ssc.5569.1.S1_at | Thyroid hormone receptor alpha | −10.22 | 1.26 | 1.26 | 6.49 | THRA | 3,5-diiodothyropropionic acid, amiodarone, thyroxine, L-triiodothyronine |
| Ssc.10360.1.S1_at | B-Raf proto-oncogene serine/threonine-protein kinase | −2.15 | 1.26 | 3.09 | 1.36 | BRAF | sorafenib |
| Ssc.5045.1.S1_at | 3-beta-hydroxysteroid-delta(8),delta(7)-isomerase | −1.55 | 1.24 | 2.19 | 2.08 | EBP | SR 31747 |
| Ssc.1498.1.S1_at | Proteasome subunit beta type 5 | −1.81 | 1.19 | 1.38 | 5.94 | PSMB5 | bortezomib |
| Ssc.28329.1.S1_at | DNA polymerase beta | 1.14 | 1.19 | 1.07 | 5.25 | POLB | nelarabine, clofarabine, stavudine, trifluridine, vidarabine, zalcitabine, entecavir |
| Ssc.16823.1.S1_at | P2Y purinoceptor 12 (P2Y12) (P2Y12 platelet ADP receptor) (P2Y(ADP)) | 1.38 | 1.19 | 1.41 | 1.11 | P2RY12 | prasugrel, AZD 6140, clopidogrel |
| Ssc.19691.1.S1_at | Platelet-activating factor acetylhydrolase | 1.59 | 1.16 | 3.01 | 1.47 | PLA2G7 | darapladib |
| Ssc.19700.1.S1_at | Serine/threonine protein phosphatase 2B catalytic subunit, beta | 1.11 | 1.13 | 1.34 | 1.09 | PPP3CB | ISAtx-247, tacrolimus, pimecrolimus, cyclosporin A |
| Ssc.14488.1.S1_at | Glutamate carboxypeptidase II | −1.04 | 1.10 | 1.02 | 1.69 | FOLH1 | capromab pendetide |

TABLE 10

Upregulated gene targets at both Days 7 and 21 (relative to baseline) of PAH progression with available drugs

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.11381.1.S1_at | Interferon-alpha/beta receptor alpha chain | 10.45 | 8.08 | 2.61 | −1.30 | IFNAR1 | interferon beta-1a, interferon alfa-2b, interferon alfacon-1, PEG-interferon alfa-2a, |

TABLE 10-continued

Upregulated gene targets at both Days 7 and 21 (relative to baseline) of PAH progression with available drugs

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.16186.1.S1_at | T-cell surface glycoprotein CD3 epsilon chain | 9.00 | 3.12 | 2.12 | −5.66 | CD3E | interferon alfa-2a/ribavirin, pegintron, interferon beta-1b, IFNA2A visilizumab, MT103, muromonab-CD3 |
| Ssc.19673.1.S1_at | T-cell surface glycoprotein CD3 delta chain | 6.40 | 2.70 | 2.03 | −11.77 | CD3D | visilizumab, MT103 |
| Ssc.17155.1.A1_at | heparanase; heparanase-1 | 4.81 | 5.38 | 2.98 | −1.83 | HPSE | heparanase inhibitor PI-88 |
| Ssc.7130.1.S1_at | Phenylalanine-4-hydroxylase | 4.70 | 4.71 | 11.30 | 1.48 | PAH | (6R)-tetrahydrobiopterin |
| Ssc.26351.1.S1_at | cAMP-specific 3',5'-cyclic phosphodiesterase 4D | 4.67 | 4.99 | 3.61 | −1.15 | PDE4D | dyphylline, nitroglycerin, arofylline, tetomilast, L869298, aminophylline, anagrelide, cilomilast, milrinone, rolipram, dipyridamole, L-826,141, roflumilast, tolbutamide, theophylline, pentoxifylline, caffeine |
| Ssc.7176.1.A1_at | C—X—C chemokine receptor type 4 (CXC-R4) (CXCR-4) | 3.74 | 10.91 | 8.15 | 1.68 | CXCR4 | JM 3100 |
| Ssc.15801.1.A1_at | Protein kinase C, beta | 3.36 | 6.36 | 3.53 | −4.98 | PRKCB1 | enzastaurin, ruboxistaurin |
| Ssc.12791.1.A1_at | 3-hydroxy-3-methylglutaryl-coenzyme A reductase | 3.27 | 2.77 | 1.77 | −2.56 | HMGCR | aspirin/pravastatin, lovastatin/niacin, ezetimibe/simvastatin, amlodipine/atorvastatin, fluvastatin, cerivastatin, atorvastatin, pravastatin, simvastatin, lovastatin, rosuvastatin |
| Ssc.11147.1.S1_at | Aldehyde dehydrogenase, mitochondrial | 3.18 | 1.13 | 2.00 | −1.68 | ALDH2 | disulfiram, chlorpropamide |
| Ssc.9565.1.S1_at | Interferon-gamma receptor alpha chain | 2.92 | 1.63 | 1.41 | −1.23 | IFNGR1 | interferon gamma-1b |
| Ssc.3607.1.S1_at | Interferon-alpha/beta receptor beta | 2.28 | 4.65 | 1.11 | −1.56 | IFNAR2 | interferon beta-1a, interferon alfa-2b, interferon alfacon-1, PEG-interferon alfa-2a, interferon alfa-2a/ribavirin, pegintron, interferon beta-1b, IFNA2A |
| Ssc.4756.1.A1_at | Adenosine A3 receptor. | 2.15 | 2.10 | 1.88 | −1.81 | ADORA3 | adenosine, dyphylline, aminophylline, clofarabine, theophylline, caffeine |
| Ssc.10142.1.A1_at | Dihydropyrimidine dehydrogenase [NADP+] | 2.06 | 2.17 | 1.13 | −2.68 | DPYD | eniluracil |
| Ssc.15822.1.S1_at | Coagulation factor V | 1.92 | 3.76 | 1.89 | −1.75 | F5 | drotrecogin alfa |
| Ssc.14258.1.S1_at | Amyloid beta A4 protein precursor (APP) (ABPP) | 1.87 | 3.33 | 1.34 | −1.02 | APP | AAB-001 |
| Ssc.15878.1.S1_at | Serine/threonine protein phosphatase 2B catalytic subunit, alpha | 1.85 | 3.22 | 3.62 | −1.49 | PPP3CA | ISAtx-247, tacrolimus, pimecrolimus, cyclosporin A |
| Ssc.9272.1.S1_at | Tumor-associated calcium signal transducer 1 (EPCAM antigen) | 1.81 | 3.94 | 176.50 | 2.07 | TACSTD1 | tucotuzumab celmoleukin |
| Ssc.19691.1.S1_at | Platelet-activating factor acetylhydrolase | 1.59 | 1.16 | 3.01 | 1.47 | PLA2G7 | darapladib |
| Ssc.30147.1.A1_at | Fibroblast growth factor receptor 2 | 1.56 | 1.13 | −1.05 | −1.18 | FGFR2 | palifermin |
| Ssc.16823.1.S1_at | P2Y purinoceptor 12 (P2Y12) (P2Y12 platelet ADP receptor) | 1.38 | 1.19 | 1.41 | 1.11 | P2RY12 | prasugrel, AZD 6140, clopidogrel |
| Ssc.15999.1.A1_at | Vascular endothelial growth factor receptor 2 | 1.24 | 1.24 | 18.52 | −11.02 | KDR | AEE 788, sunitinib, AZD 2171, pazopanib, XL647, CEP 7055, BMS-582664, KRN-951, vatalanib, sorafenib, vandetanib, pegaptanib |
| Ssc.17224.1.S1_at | Toll-like receptor 8 | 1.17 | 6.49 | 3.13 | −1.52 | TLR6 | resiquimod |
| Ssc.7297.1.S1_at | Amine oxidase | 1.16 | 6.42 | 7.02 | −1.13 | MAOB | safinamide, ladostigil, rasagiline, selegiline, dextroamphetamine, procainamide, tranylcypromine, phenelzine, isocarboxazid, benzphetamine |

TABLE 10-continued

Upregulated gene targets at both Days 7 and 21 (relative to baseline) of PAH progression with available drugs

| Probe ID | Name | Fold Change D7/Base | Fold Change D21/Base | Fold Change D60/Base | Fold Change D180/Base | Gene Symbol | Drugs |
|---|---|---|---|---|---|---|---|
| Ssc.28329.1.S1_at | DNA polymerase beta | 1.14 | 1.19 | 1.07 | 5.25 | POLB | nelarabine, clofarabine, stavudine, trifluridine, vidarabine, zalcitabine, entecavir |
| Ssc.19700.1.S1_at | Serine/threonine protein phosphatase 2B catalytic subunit, beta | 1.11 | 1.13 | 1.34 | 1.09 | PPP3CB | ISAtx-247, tacrolimus, pimecrolimus, cyclosporin A |
| Ssc.8726.1.A1_at | Amidophoshoribosyltransferase precursor | 1.03 | 1.24 | 4.16 | −1.11 | PPAT | 6-mercaptopurine, thioguanine, azathioprine |

TABLE 11

Animal number, days after post-shunt PAH creation surgery, and pulmonary arterial pressure (PAP).

| Animal | Day | PAP | PAP mean |
|---|---|---|---|
| Pig 19 Timecourse | | | |
| P19 | Day 0 | 28/1 | 26 |
| P19 | Day 10 | 22/17 | 19 |
| P19 | Day 24 | 76/29 | 47 |
| P19 | Day 59 | 89/50 | 58 |
| P19 | Day 94 | 70/18 | 54 |
| Pig 20 Timecourse | | | |
| P20 | Day 0 | 20/11 | 16 |
| P20 | Day 6 | 19/15 | 16 |
| P20 | Day 21 | 20/15 | 17 |
| P20 | Day 55 | 23/15 | 19 |
| P20 | Day 83 | 62/17 | 45 |
| P20 | Day 104 | 116/72 | 104 |
| P20 | Day 140 | 92/40 | 81 |
| Normal (Normal Pressure & Flow) | | | |
| P19 | Day 0 | 28/1 | 26 |
| P20 | Day 0 | 20/11 | 16 |
| HFLP (High Flow Low Pressure) | | | |
| P19 | Day 10 | 22/17 | 19 |
| P20 | Day 6 | 19/15 | 16 |
| P20 | Day 21 | 20/15 | 17 |
| P20 | Day 55 | 23/15 | 19 |
| HFHP (High Flow High Pressure) | | | |
| P19 | Day 24 | 76/29 | 47 |
| P19 | Day 59 | 89/50 | 58 |
| P19 | Day 94 | 70/18 | 54 |
| P20 | Day 83 | 62/17 | 45 |
| P20 | Day 104 | 116/72 | 104 |
| P20 | Day 140 | 92/40 | 81 |

TABLE 12

Significantly differently expressed downregulated microRNAs HFHP (High Flow High Pressure) vs. normal.
Downregulated microRNA HFHP vs. Norm (p < .05)

| Illumina ID | Normal | HFHP | HFLP | miRNA Symbol |
|---|---|---|---|---|
| ILMN_3167128 | 32.58 | −2.36 | 2.75 | solexa-603-1846 |
| ILMN_3167515 | 4183.74 | 42.62 | 142.81 | hsa-miR-586 |
| ILMN_3168604 | 31.83 | −2.01 | 0.90 | hsa-miR-1201 |
| ILMN_3167691 | 127.02 | 1.76 | 1358.98 | hsa-miR-33a |
| ILMN_3167249 | 229.25 | 18.22 | 511.84 | HS_56 |
| ILMN_3167753 | 114.97 | 14.32 | 66.23 | hsa-miR-520d:9.1 |
| ILMN_3168215 | 37.30 | 8.98 | 3110.35 | hsa-miR-521 |
| ILMN_3168168 | 32.58 | 1.72 | 28.59 | hsa-miR-519a |
| ILMN_3168054 | 3916.21 | 79.38 | 14.02 | HS_134 |
| ILMN_3168235 | 58.82 | 6.34 | 2.94 | HS_169 |
| ILMN_3168335 | 15.54 | −2.85 | 26.65 | HS_221 |
| ILMN_3167393 | 90.38 | 5.18 | 5.54 | hsa-miR-496 |
| ILMN_3168678 | 837.14 | 14.23 | 777.94 | hsa-miR-935 |
| ILMN_3167175 | 8796.46 | 1274.47 | 88.95 | hsa-miR-542-5p |
| ILMN_3168905 | 92.30 | 5.07 | 33.55 | solexa-5620-151 |
| ILMN_3168648 | 593.72 | 46.29 | 812.05 | hsa-miR-99a |
| ILMN_3167761 | 37.30 | 16.59 | 0.17 | hsa-miR-212 |
| ILMN_3168709 | 1281.24 | 218.10 | 80.10 | hsa-let-7f-2 |
| ILMN_3168446 | 8875.62 | 343.70 | 546.81 | hsa-miR-494 |
| ILMN_3168663 | 31.00 | 3.29 | 18.23 | hsa-miR-1321 |
| ILMN_3168597 | 99.25 | 14.28 | 43.96 | hsa-miR-219-2-3p |
| ILMN_3166971 | 1310.30 | 311.18 | 924.85 | hsa-miR-95 |
| ILMN_3167491 | 3060.68 | 925.46 | 1647.50 | hsa-miR-128b:9.1 |
| ILMN_3168654 | 740.78 | 96.90 | 957.01 | hsa-miR-33a |
| ILMN_3167052 | 370.00 | 45.81 | 234.11 | hsa-miR-495 |
| ILMN_3167337 | 177.30 | 43.83 | 27.93 | hsa-miR-1229 |
| ILMN_3168827 | 569.48 | 117.37 | 51.85 | hsa-miR-1205 |
| ILMN_3167328 | 6444.52 | 2162.76 | 2119.65 | hsa-miR-524-3p |
| ILMN_3167952 | 8724.37 | 2076.18 | 926.06 | HS_150 |
| ILMN_3168798 | 376.77 | 151.44 | 1348.57 | hsa-miR-135a |
| ILMN_3168558 | 211.48 | 68.62 | 28.31 | hsa-miR-483-5p |
| ILMN_3168039 | 9629.83 | 3219.90 | 7248.74 | hsa-miR-124a:9.1 |
| ILMN_3168755 | 233.36 | 82.45 | 332.03 | hsa-miR-29b-1 |
| ILMN_3168540 | 493.90 | 161.33 | 304.45 | hsa-miR-548c-5p |
| ILMN_3168265 | 11306.19 | 5572.32 | 6108.39 | hsa-miR-551a |
| ILMN_3168481 | 8687.78 | 4563.60 | 5504.04 | hsa-miR-377 |
| ILMN_3168882 | 12023.57 | 6677.06 | 8627.69 | hsa-miR-1304 |

TABLE 13

Significantly differently expressed upregulated microRNAs HFHP (High Flow High Pressure) vs. normal.
Upregulated microRNA HFHP vs. Norm (p < .05)

| Illumina ID | Normal | HFHP | HFLP | miRNA Symbol |
|---|---|---|---|---|
| ILMN_3168350 | −6.40 | 2772.39 | 12.69 | hsa-miR-520g |
| ILMN_3168706 | −3.62 | 1700.55 | 8.11 | hsa-miR-331-5p |
| ILMN_3167244 | −4.11 | 1534.57 | −4.19 | hsa-miR-410 |
| ILMN_3168710 | −3.08 | 1499.40 | 2147.63 | hsa-let-7d |
| ILMN_3168167 | −4.14 | 1144.02 | 558.78 | hsa-miR-187 |
| ILMN_3168672 | −4.20 | 941.07 | 162.41 | hsa-miR-16-2 |

TABLE 13-continued

Significantly differently expressed upregulated microRNAs HFHP (High Flow High Pressure) vs. normal.
Upregulated microRNA HFHP vs. Norm (p < .05)

| Illumina ID | Normal | HFHP | HFLP | miRNA Symbol |
|---|---|---|---|---|
| ILMN_3168870 | −8.25 | 912.52 | 8.99 | hsa-miR-130a |
| ILMN_3168639 | −4.96 | 728.32 | −3.51 | hsa-miR-548n |
| ILMN_3168719 | −1.17 | 380.69 | −2.12 | hsa-miR-127-5p |
| ILMN_3168890 | −4.11 | 343.04 | 530.05 | solexa-2580-353 |
| ILMN_3168217 | −5.60 | 304.34 | −1.25 | HS_206 |
| ILMN_3167088 | −5.06 | 303.57 | −0.34 | hsa-miR-663 |
| ILMN_3168911 | −1.32 | 235.62 | 61.24 | solexa-7534-111 |
| ILMN_3168732 | −0.63 | 216.74 | 12.96 | hsa-let-7g |
| ILMN_3167993 | −6.45 | 192.76 | 237.96 | HS_157 |
| ILMN_3167193 | −7.25 | 151.36 | 2130.07 | hsa-miR-610 |
| ILMN_3167879 | −4.09 | 111.71 | 11.99 | HS_251.1 |
| ILMN_3168031 | −4.54 | 52.02 | 15.76 | hsa-miR-519e |
| ILMN_3168818 | −4.09 | 20.75 | −0.83 | hsa-miR-1237 |
| ILMN_3168241 | −2.10 | 18.57 | 649.52 | hsa-miR-1185 |
| ILMN_3167470 | −4.18 | 12.39 | 7.90 | HS_151.1 |
| ILMN_3167512 | −1.69 | 11.79 | 9.99 | HS_135 |
| ILMN_3168895 | −2.86 | 7.81 | 0.75 | solexa-3126-285 |
| ILMN_3167158 | −0.63 | 3.36 | 739.08 | hsa-miR-30a |
| ILMN_3168722 | 1.26 | 529.41 | 430.69 | hsa-miR-192 |
| ILMN_3167039 | 17.25 | 1036.96 | 883.92 | hsa-miR-568 |
| ILMN_3168680 | 2.62 | 148.59 | 54.43 | hsa-miR-1203 |
| ILMN_3167223 | 381.67 | 5756.85 | 4105.59 | hsa-miR-28-5p |
| ILMN_3167361 | 21.39 | 259.94 | 255.04 | HS_262.1 |
| ILMN_3167684 | 11.78 | 80.14 | 21.38 | HS_170 |
| ILMN_3168760 | 11.78 | 80.09 | 26.17 | hsa-miR-1273 |
| ILMN_3167275 | 39.19 | 146.84 | 1900.87 | hsa-miR-602 |
| ILMN_3168240 | 1613.60 | 5725.95 | 4943.62 | hsa-miR-374a |
| ILMN_3168589 | 597.66 | 1739.42 | 928.77 | hsa-miR-29a |

TABLE 14

Significantly differently expressed downregulated microRNAs HFLP (High Flow Low Pressure) vs. normal.
Downregulated microRNA HFLP vs. Norm (p < .05)

| Illumina ID | Normal | HFLP | HFHP | Gene Symbol |
|---|---|---|---|---|
| ILMN_3167209 | 27.46 | −3.19 | 1350.01 | HS_104 |
| ILMN_3168537 | 38.77 | −0.76 | 57.24 | hsa-miR-548a-5p |
| ILMN_3167655 | 351.30 | 0.20 | 74.35 | hsa-miR-556-5p |
| ILMN_3168235 | 58.82 | 2.94 | 6.34 | HS_169 |
| ILMN_3167800 | 13.08 | −2.83 | 1036.31 | HS_140 |
| ILMN_3167175 | 8796.46 | 88.95 | 1274.47 | hsa-miR-542-5p |
| ILMN_3168054 | 3916.21 | 14.02 | 79.38 | HS_134 |
| ILMN_3167761 | 37.30 | 0.17 | 16.59 | hsa-miR-212 |
| ILMN_3167509 | 17.25 | −1.53 | 17.72 | hsa-miR-363 |
| ILMN_3167707 | 130.17 | 1.49 | 42.39 | HS_59 |
| ILMN_3167515 | 4183.74 | 142.81 | 42.62 | hsa-miR-586 |
| ILMN_3168446 | 8875.62 | 546.81 | 343.70 | hsa-miR-494 |
| ILMN_3168827 | 569.48 | 51.85 | 117.37 | hsa-miR-1205 |
| ILMN_3168709 | 1281.24 | 80.10 | 218.10 | hsa-let-7f-2 |
| ILMN_3168558 | 211.48 | 28.31 | 68.62 | hsa-miR-483-5p |
| ILMN_3167952 | 8724.37 | 926.06 | 2076.18 | HS_150 |
| ILMN_3167337 | 177.30 | 27.93 | 43.83 | hsa-miR-1229 |
| ILMN_3168305 | 31.00 | 5.36 | 34.52 | HS_156 |
| ILMN_3168490 | 67.94 | 18.69 | 106.29 | hsa-miR-619 |
| ILMN_3168573 | 776.09 | 190.47 | 805.44 | hsa-miR-10b |
| ILMN_3168586 | 887.48 | 304.35 | 617.25 | hsa-miR-371-5p |

TABLE 15

Significantly differently expressed upregulated microRNAs HFLP (High Flow Low Pressure) vs. normal.
Upregulated microRNA HFLP vs. Norm (p < .05)

| Illumina ID | Normal | HFLP | HFHP | miRNA Symbol |
|---|---|---|---|---|
| ILMN_3168010 | −9.81 | 2363.55 | 689.66 | HS_70 |
| ILMN_3168710 | −3.08 | 2147.63 | 1499.40 | hsa-let-7d |
| ILMN_3168167 | −4.14 | 558.78 | 1144.02 | hsa-miR-187 |
| ILMN_3168890 | −4.11 | 530.05 | 343.04 | solexa-2580-353 |
| ILMN_3167993 | −6.45 | 237.96 | 192.76 | HS_157 |
| ILMN_3168911 | −1.32 | 61.24 | 235.62 | solexa-7534-111 |
| ILMN_3168870 | −8.25 | 8.99 | 912.52 | hsa-miR-130a |
| ILMN_3167512 | −1.69 | 9.99 | 11.79 | HS_135 |
| ILMN_3168722 | 1.26 | 430.69 | 529.41 | hsa-miR-192 |
| ILMN_3167720 | 2.62 | 145.01 | 147.62 | hsa-miR-154 |
| ILMN_3167062 | 78.98 | 2184.01 | 1423.21 | hsa-miR-151:9.1 |
| ILMN_3168680 | 2.62 | 54.43 | 148.59 | hsa-miR-1203 |
| ILMN_3167778 | 24.39 | 206.06 | 81.33 | hsa-miR-525-3p |
| ILMN_3167749 | 37.30 | 226.26 | 272.25 | HS_199 |

TABLE 16

Significantly differently expressed upregulated microRNAs HFHP vs. HFLP.
Upregulated microRNA HFHP vs. HFLP (p < .05)

| Illumina ID | Normal | HFHP | HFLP | miRNA Symbol |
|---|---|---|---|---|
| ILMN_3167244 | −4.11 | 1534.57 | −4.19 | has-miR-410 |
| ILMN_3168639 | −4.96 | 728.32 | −3.51 | has-miR-548n |
| ILMN_3168537 | 38.77 | 57.24 | −0.76 | has-miR-548a-5p |
| ILMN_3168613 | 4.53 | 18.13 | −0.99 | has-miR-185 |
| ILMN_3168047 | 34.59 | 10.25 | −4.94 | HS_3 |
| ILMN_3167440 | 71.49 | −0.51 | −4.89 | HS_67 |
| ILMN_3168585 | 45.00 | 97.09 | 2.43 | has-miR-1250 |
| ILMN_3168543 | 140.56 | 2778.92 | 47.17 | has-miR-5481 |
| ILMN_3168221 | 52.52 | 216.12 | 13.76 | has-miR-548c-3p |
| ILMN_3167831 | 31.83 | 186.98 | 12.94 | has-miR-520d-5p |
| ILMN_3167105 | 292.19 | 174.71 | 25.34 | has-miR-208b |
| ILMN_3167313 | 475.92 | 793.85 | 135.08 | HS_200 |
| ILMN_3168634 | 892.54 | 1830.74 | 479.17 | has-miR-218-1 |
| ILMN_3168247 | 390.00 | 300.41 | 111.54 | has-miR-643 |

TABLE 17

Significantly differently expressed downregulated microRNAs HFHP vs. HFLP.
Downregulated microRNA HFHP vs. HFLP (p < .05)

| Illumina ID | Normal | HFHP | HFLP | miRNA Symbol |
|---|---|---|---|---|
| ILMN_3167778 | 24.39 | 81.33 | 206.06 | hsa-miR-525-3p |
| ILMN_3167052 | 370.00 | 45.81 | 234.11 | hsa-miR-495 |
| ILMN_3168052 | 176.33 | 116.43 | 480.71 | HS_250 |
| ILMN_3168863 | 9.59 | 1.11 | 46.30 | hsa-miR-933 |
| ILMN_3168848 | 13.53 | 8.90 | 475.98 | hsa-miR-1287 |
| ILMN_3168750 | 784.33 | 2850.15 | 8118.48 | hsa-miR-1308 |
| ILMN_3168348 | 10.81 | 9.66 | 553.87 | hsa-miR-133b |
| ILMN_3166995 | 1.97 | 1.33 | 254.82 | HS_215 |
| ILMN_3167545 | 42.85 | 10.92 | 23.89 | HS_115 |
| ILMN_3168819 | 756.53 | 1345.27 | 5334.48 | hsa-miR-151-5p |
| ILMN_3167249 | 229.25 | 18.22 | 511.84 | HS_56 |
| ILMN_3168010 | −9.81 | 689.66 | 2363.55 | HS_70 |
| ILMN_3168215 | 37.30 | 8.98 | 3110.35 | hsa-miR-521 |

I claim:

1. A method of treating an individual suffering from the vascular-related disease pulmonary arterial hypertension comprising the steps of:
   a) obtaining a biopsy sample from the individual's pulmonary artery;
   b) analyzing gene expression levels of the biopsy sample from the pulmonary artery of the individual and the non-diseased control, wherein the analyzing of gene expression levels are for genes unassociated with the vascular-related disease, and further wherein the gene for which expression is analyzed is chosen from the group consisting of HSPE, YES1, CFTR, MAOA, MAOB, and CACNA2D1;

c) comparing the gene expression levels between the biopsy sample from the pulmonary artery of the individual and the non-diseased control;

d) identifying at least one gene from step c) that is upregulated or downregulated in the biopsy sample based on the non-diseased control;

e) obtaining gene products from the genes identified in step c); and f) selecting pharmaceutical agents which are known inhibitors of the gene products from the at least one upregulated gene or known promoters of the gene products from the at least one downregulated gene, wherein the pharmaceutical agents selected are administered to the individual suffering from the vascular-related disease.

2. The method of claim 1, wherein the biopsy sample is extracted using an endoarterial catheter.

3. The method of claim 1, wherein the gene expression levels are analyzed by extracting RNA from the biopsy sample.

4. The method of claim 3, wherein the RNA is converted to cDNA and the cDNA is compared in step c).

5. The method of claim 1, wherein step b) is accomplished using a microarray.

6. The method of claim 1, wherein the individual suffering from the vascular-related disease is in the early stage progression of the vascular-related disease.

7. The method of claim 6, wherein the pharmaceutical agents to treat the early stage progression of the vascular-related disease is at least one member selected from the group consisting of the drugs listed in Table 3.

8. The method of claim 1, wherein the individual suffering from the vascular-related disease is in the mid stage progression of the vascular-related disease.

9. The method of claim 1, wherein the individual suffering from the vascular-related disease is in the late stage progression of the vascular-related disease.

10. The method of claim 8, wherein the pharmaceutical agents to treat the mid stage progression of the vascular-related disease is at least one member selected from the group consisting of the drugs listed in Tables 4 and 5.

11. The method of claim 9, wherein the pharmaceutical agents to treat the late stage progression of the vascular-related disease is at least one member selected from the group consisting of the drugs listed in Table 6.

* * * * *

UNITED STATES PATENT AND TRADEMARK OFFICE
CERTIFICATE OF CORRECTION

| | | |
|---|---|---|
| PATENT NO. | : 8,741,861 B2 | Page 1 of 2 |
| APPLICATION NO. | : 12/934950 | |
| DATED | : June 3, 2014 | |
| INVENTOR(S) | : Mann | |

It is certified that error appears in the above-identified patent and that said Letters Patent is hereby corrected as shown below:

On the title page item (57), line 8, Abstract, the word "disorder" should read "disorders";

In the Specification

Col. 1, line 32: insert the word --rate-- before the word "from";

Col. 2, line 52-53: the word "angiopoetin-1" should read "angiopoieten-1";

Col. 2, line 60: insert the word --or-- before the word "K+";

Col. 5, line 19: the word "PAN" in step (a) should read "PAH";

Col. 7, line 6: insert the word --was-- before the word "immediately";

Col. 7, line 24: the word "halpthane" should read "halothane";

Col. 7, line 27: insert -- - -- between the words "end" and "hole";

Col. 7, line 29: insert -- - -- between the words "end" and "hole";

Col. 7, line 67: the word "will" should read "were";

Col. 8, line 2: insert --/-- between the words "and" and "or";

Col. 9, line 14: the word "R-Eioconductor" should read "R-Bioconductor";

Col. 10, line 34: insert -- - -- between the words "Endothelin" and "1";

Signed and Sealed this
Twelfth Day of August, 2014

Michelle K. Lee
*Deputy Director of the United States Patent and Trademark Office*

CERTIFICATE OF CORRECTION (continued)
U.S. Pat. No. 8,741,861 B2

Col. 11, line 15: the word "illumine's" should read "illumina's";

Col. 11, line 25: insert a --.-- after the word "arrays";

Col. 11, line 49: the word "in" should read "into";

Col. 12, line 21: the word "diseases" should read "disease's".